(12) United States Patent
Horiuchi et al.

(10) Patent No.: US 7,615,640 B2
(45) Date of Patent: Nov. 10, 2009

(54) ORGANIC DYE, PHOTOELECTRIC CONVERSION MATERIAL, SEMICONDUCTOR ELECTRODE AND PHOTOELECTRIC CONVERSION DEVICE

(75) Inventors: Tamotsu Horiuchi, Tokyo (JP); Hidetoshi Miura, Tokyo (JP)

(73) Assignee: Mitsubishi PaperMillsLtd., Tokyo (JP)

( * ) Notice: Subject to any disclaimer, the term of this patent is extended or adjusted under 35 U.S.C. 154(b) by 155 days.

(21) Appl. No.: 11/984,199

(22) Filed: Nov. 14, 2007

(65) Prior Publication Data

US 2008/0149175 A1    Jun. 26, 2008

Related U.S. Application Data

(62) Division of application No. 10/488,047, filed as application No. PCT/JP03/09408 on Jul. 24, 2003.

(30) Foreign Application Priority Data

| Jul. 29, 2002 | (JP) | ............................. 2002-220145 |
| Sep. 26, 2002 | (JP) | ............................. 2002-280105 |
| Oct. 15, 2002 | (JP) | ............................. 2002-300782 |
| Dec. 19, 2002 | (JP) | ............................. 2002-368719 |
| Jan. 31, 2003 | (JP) | ............................. 2003-023205 |

(51) Int. Cl.
*C07D 215/38* (2006.01)
*C07D 251/18* (2006.01)
*C07D 241/36* (2006.01)
*C07D 209/82* (2006.01)
*C07D 209/04* (2006.01)
*H01L 25/00* (2006.01)
*H01L 31/00* (2006.01)
*H01M 6/30* (2006.01)

(52) U.S. Cl. ...................... 546/159; 544/105; 544/353; 544/354; 548/439; 548/469; 136/243; 136/263; 429/111

(58) Field of Classification Search ....................... None
See application file for complete search history.

(56) References Cited

U.S. PATENT DOCUMENTS

4,927,721 A   5/1990   Gratzel et al. ............... 429/111

(Continued)

FOREIGN PATENT DOCUMENTS

EP   1 311 001   5/2003

(Continued)

OTHER PUBLICATIONS

International Search Report for International (PCT) Application PCT/JP03/09408.

(Continued)

*Primary Examiner*—Alexa D Neckel
*Assistant Examiner*—Shannon Gardner
(74) *Attorney, Agent, or Firm*—Wenderoth, Lind & Ponack, L.L.P.

(57) ABSTRACT

Disclosed are an organic dye having a specific structure, a photoelectric conversion material containing the dye, a semiconductor electrode formed of a substrate having an electrically conductive surface, a semiconductor layer coated on the electrically conductive surface and the above dye adsorbed on the surface, and a photoelectric conversion device to which the above dye is applied.

The present invention uses the above dye and can therefore provide a photoelectric conversion device excellent in photoelectric conversion efficiency, and the photoelectric conversion device is suitable for use in a solar cell or the like.

7 Claims, 14 Drawing Sheets

U.S. PATENT DOCUMENTS

2003/0152827 A1* 8/2003 Ikeda et al. ............ 429/111

FOREIGN PATENT DOCUMENTS

| JP | 11-238905 | 8/1999 |
| JP | 2001-52766 | 2/2001 |
| JP | 2001-76773 | 3/2001 |
| JP | 03/005481 | 1/2003 |
| WO | 02/11213 | 2/2002 |
| WO | 03/005481 | 1/2003 |

OTHER PUBLICATIONS

Supplementary European Search Report dated Apr. 13, 2006 for European application No. 03771315.

Patent Abstracts of Japan, vol. 2000, No. 19, Jun. 5, 2001 & JP 2001 042524, Feb. 16, 2001.

* cited by examiner

ORGANIC DYE, PHOTOELECTRIC CONVERSION MATERIAL, SEMICONDUCTOR ELECTRODE AND PHOTOELECTRIC CONVERSION DEVICE

This application is a divisional of U.S. application Ser. No. 10/488,047, filed Mar. 18, 2004, which is a national stage application of International application No. PCT/JP03/09408 filed Jul. 24, 2003.

TECHNICAL FIELD

The present invention relates to a novel organic dye, a photoelectric conversion material, a semiconductor electrode and a photoelectric conversion device. More specifically, the present invention relates to a novel organic dye having an excellent photoelectric conversion property useful for use in a semiconductor electrode in a solar cell or the like, a photoelectric conversion material containing the above dye, a semiconductor electrode containing the above material and a photoelectric conversion device having the above semiconductor electrode and being excellent in photoelectric conversion efficiency.

TECHNICAL BACKGROUND

It has come to be recognized that global warming caused by an increase in $CO_2$ concentration driven by the use of a large amount of fossil fuels and an increase in energy demands driven by population growth have posed problems of annihilation of the human species. In recent years, therefore, studies are being energetically made for the utilization of sunlight that is infinite and free from the occurrence of harmful substances. For utilizing the above sunlight that is a clean energy source, there are practically used inorganic solar cells for residential buildings, such as a solar cell of single crystal silicon, polycrystal silicon, amorphous silicon, cadmium telluride and indium copper selenide.

However, silicon for use in the above solar cell is required to have very high purity, and the purification step thereof is complicated and requires a large number of processes. The solar cell requires a high production cost. The solar energy generation based on the above inorganic materials is disadvantageous in view of a cost and a long period of redemption for users, which have been problems that hinder the spread thereof.

On the other hand, many types of solar cells using organic materials have been also proposed. The organic solar cells include a Schottky type photoelectric conversion device having a junction formed by a p-type organic semiconductor and a metal having a small work function and a hetero-junction type photoelectric conversion device having a junction formed by a p-type organic semiconductor and an n-type inorganic semiconductor or a junction formed by a p-type organic semiconductor and an electron-accepting organic compound. The organic semiconductor used contains a material selected from synthetic dyes or pigments such as chlorophyll or perylene, electrically conductive polymer materials such as polyacetylene or composite materials of these. A thin film is formed from any one of these materials by a vacuum vapor deposition method, a casting method, a dipping method, or the like to constitute a cell material. While the organic materials have advantages that they are less expensive and permit the easy formation of a large area, they have problems that many of them exhibit a conversion of 1% or less and that they are poor in durability.

Under the circumstances, "Photoelectric conversion device using dye-sensitized semiconductor fine particles and solar cells" reported in Nature (Vol. 353, page 737, 1991) and U.S. Pat. No. 4,927,721 was remarkable. The above documents also disclose materials and a production technique, which are necessary for producing the cell. The proposed cells are called "Graeztel" type, and they are wet solar cells using, as a work electrode, a porous thin film of titanium oxide spectrally sensitized with a ruthenium complex. The above method has the following advantages; It is not required to purify a semiconductor of a less expensive oxide such as titanium oxide until it has a high purity, so that the cells are less expensive, and light that can be utilized covers up to a broad visible light region, so that sunlight containing a large quantity of visible light components can be effectively converted to electricity.

On the other hand, the above cells use a very expensive ruthenium complex and require an improvement in view of a cost. This problem can be overcome if the expensive ruthenium complex can be replaced with a less expensive organic dye such as cyanine or the like. A cyanine dye and a merocyanine dye have been developed as a dye for the above cells (JP-A-11-238905, JP-A-2001-52766 and JP-A-2001-76773). However, these dyes have low adsorption to titanium oxide or cannot yet produce an high sensitization effect, and they also have a problem with regard to stability with the passage of time (durability).

Under the circumstances, it is a first object of the present invention to provide a novel organic dye that has excellent stability with the passage of time and an excellent photoelectric conversion property and which is suitable for use in a semiconductor electrode, or the like, and a photoelectric conversion material containing the dye. It is also a second object of the present invention to provide a semiconductor electrode to which the above organic dye is applied and a photoelectric conversion device excellent in photoelectric conversion efficiency.

DISCLOSURE OF THE INVENTION

For achieving the above objects, the present inventors have made diligent studies, and as a result, it has been found that the objects can be achieved by an organic dye having a specific structure. On the basis of this finding, the present invention has been completed.

That is, the present invention provides:

(1) an organic dye (to be referred to as "dye I" hereinafter) having a structure represented by the general formula (I),

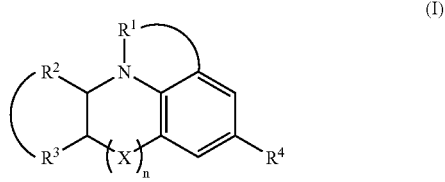

wherein $R^1$ is an alkyl group, an aralkyl group, an alkenyl group, an aryl group or a heterocyclic moiety and may have a substituent, or $R^1$ may form a cyclic structure with a benzene ring; each of $R^2$ and $R^3$ is a hydrogen atom, an alkyl group, an alkoxy group, an alkylthio group, a mono-substituted amino group, a di-substituted amino group, an aralkyl group, an alkenyl group, and aryl group or a heterocyclic moiety and may have a substituent, or $R^2$ and $R^3$ may form a cyclic structure directly or through a binding group; $R^4$ is a substituent having an acidic group; X is methylene, an oxygen atom, a sulfur atom, an amino group or a substituted amino group; and n is an integer of 0 or 1, (2) a photoelectric conversion material containing the organic dye recited in the above (1), (3) a semiconductor electrode formed of a substrate having an electrically conductive surface, a semiconductor layer coated on the electrically conductive surface and a dye adsorbed on the surface of the semiconductor layer, wherein said dye contains the organic dye recited in the above (1), (4) a photoelectric conversion device using the organic dye recited in the above (1), (5) a merocyanine dye (to be referred to as "dye II" hereinafter) having a structure represented by the general formula (II),

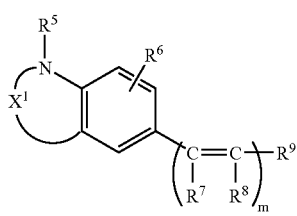

(II)

wherein $R^5$ is an alkyl group, an aralkyl group, an alkenyl group, an aryl group or a heterocyclic moiety and may have a substituent; $R^6$ is an alkyl group, an alkoxy group or a halogen atom and may have a substituent; each of $R^7$ and $R^8$ is a hydrogen atom, an alkyl group, an alkoxy group, an alkylthio group, an aryl group, an aryloxy group, an arylthio group or a heterocyclic moiety and may have a substituent; $R^9$ is a substituent having an acidic group; $X^1$ is a binding group that forms a cyclic structure together with an amino group; m is 0 or 1, and a carbon-carbon double bond may be any one of E form and Z form, (6) a photoelectric conversion material containing the merocyanine dye recited in the above (5), (7) a semiconductor electrode formed of a substrate having an electrically conductive surface, a semiconductor layer coated on the electrically conductive surface and a dye adsorbed on the surface of the semiconductor layer, wherein said dye contains the merocyanine dye recited in the above (5), (8) a photoelectric conversion device to which the merocyanine dye recited in the above (5) is applied, (9) a merocyanine dye (to be referred to as "dye III" hereinafter) having a structure represented by the general formula (IV),

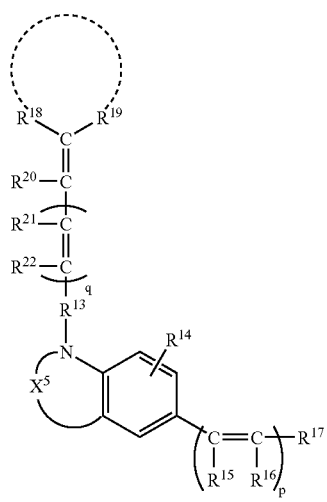

(IV)

wherein $R^{13}$ is an arylene group or a heterocyclic moiety and may have a substituent; $R^{14}$ is a hydrogen atom, an alkyl group, an alkoxy group or a halogen atom; each of $R^{15}$ and $R^{16}$ is a hydrogen atom, an alkyl group, an alkoxy group, an alkylthio group, a mono-substituted amino group, a di-substituted amino group, an aralkyl group, an alkenyl group, an aryl group or a heterocyclic moiety and may have a substituent; $R^{17}$ is a substituent having an acidic group; each of $R^{18}$ and $R^{19}$ is a hydrogen atom, an alkyl group, an aryl group or a heterocyclic moiety and may have a substituent, and $R^{18}$ and $R^{19}$ may bond directly or through a binding group; each of $R^{20}$, $R^{21}$ and $R^{22}$ is a hydrogen atom, an alkyl group, an alkoxy group, an aryl group or a heterocyclic moiety; $X^5$ is a binding group that forms a cyclic structure together with an amino group; p is an integer of 0 to 2; q is an integer of 0 to 2; and a carbon-carbon double bond may be any one of E form and Z form,

(10) a photoelectric conversion material containing the merocyanine dye recited in the above (9),

(11) a semiconductor electrode formed of a substrate having an electrically conductive surface, a semiconductor layer coated on the electrically conductive surface and a dye adsorbed on the surface of the semiconductor layer, wherein said dye contains the merocyanine dye recited in the above (9),

(12) a photoelectric conversion device to which the merocyanine dye recited in the above (9) is applied,

(13) a merocyanine dye (to be referred to as "dye IV" hereinafter) having a structure represented by the general formula (V),

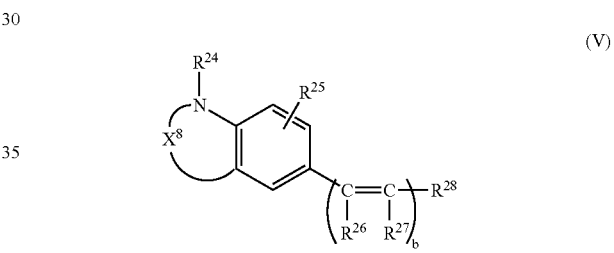

(V)

wherein $R^{24}$ is an alkyl group, an aralkyl group, an alkenyl group, an aryl group or a heterocyclic moiety and may have a substituent; $R^{25}$ is an alkyl group, an alkoxy group or a halogen atom and may have a substituent; each of $R^{26}$ and $R^{27}$ is a hydrogen atom, an alkyl group, an alkoxy group, an alkylthio group, an aryl group, an aryloxy group, an arylthio group or a heterocyclic moiety and may have a substituent; $R^{28}$ is a quaternary ammonium salt of an acidic group, a metal salt of an acidic group, an amido group or a substituent having an ester group; $X^8$ is a binding group that forms a cyclic structure together with an amino group, b is 0 or 1; and a carbon-carbon double bond may be any one of E form and Z form,

(14) a photoelectric conversion material containing the merocyanine dye recited in the above (13),

(15) a semiconductor electrode formed of a substrate having an electrically conductive surface, a semiconductor layer coated on the electrically conductive surface and a dye adsorbed on the surface of the semiconductor layer, wherein said dye contains the merocyanine dye recited in the above (13), and

(16) a photoelectric conversion device to which the merocyanine dye recited in the above (13) is applied.

PREFERRED EMBODIMENTS OF THE INVENTION

Figure 1:
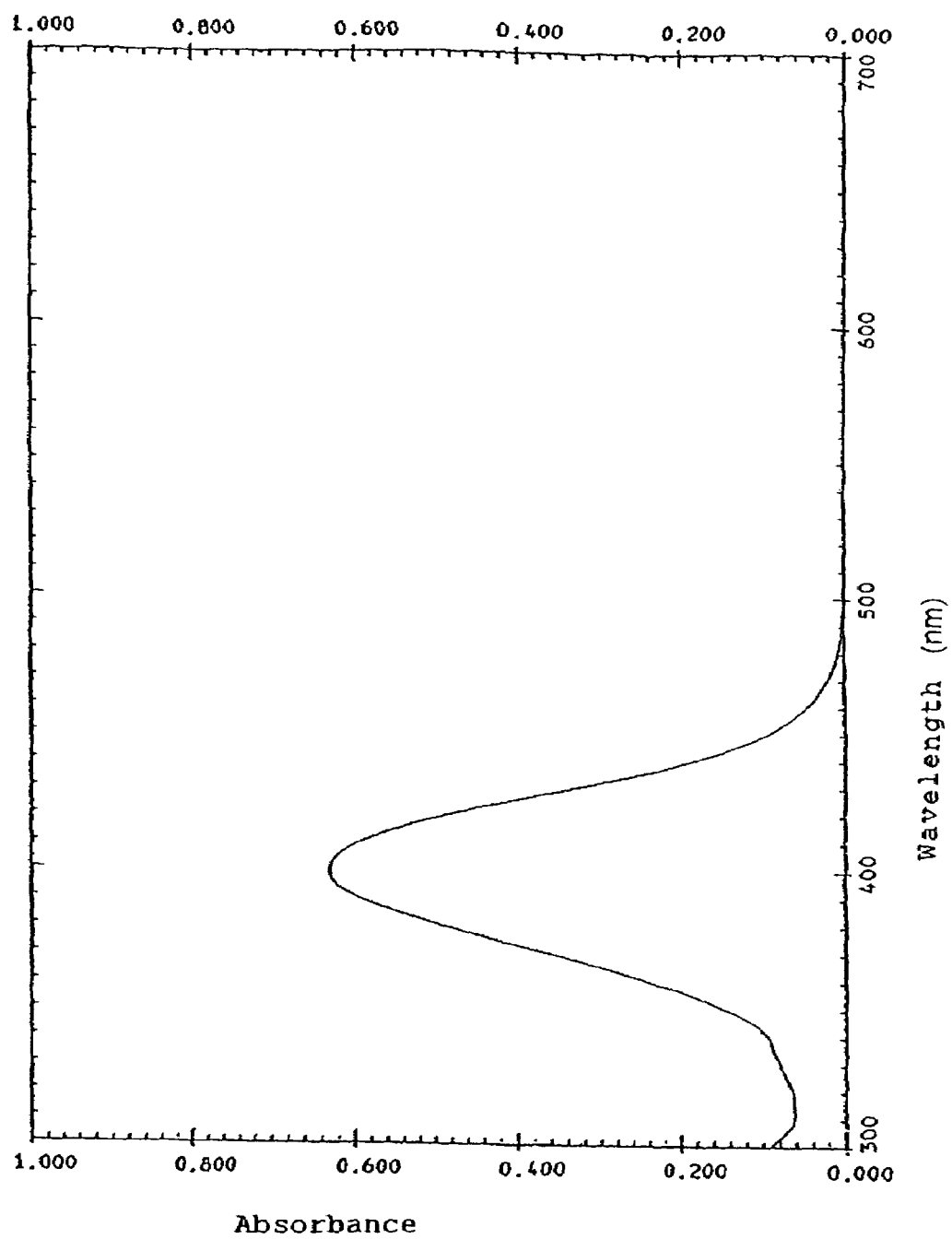
FIGS. 1 to 13 are UV absorption spectrum charts of dyes obtained in Examples W-1 to W-13.

The dye of the present invention includes embodiments of the dye I, dye II, dye III and dye IV, and each dye will be explained.

The dye I of the present invention is an organic dye having a structure represented by the general formula (I).

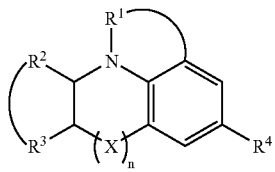

(I)

In the general formula (I), $R^1$ is an alkyl group, an aralkyl group, an alkenyl group, an aryl group or a heterocyclic moiety and may have a substituent, or $R^1$ may form a cyclic structure with a benzene ring; each of $R^2$ and $R^3$ is a hydrogen atom, an alkyl group, an alkoxy group, an alkylthio group, a mono-substituted amino group, a di-substituted amino group, an aralkyl group, an alkenyl group, an aryl or a heterocyclic moiety and may have a substituent, or $R^2$ and $R^3$ may form a cyclic structure directly or through a binding group; $R^4$ is a substituent having an acidic group; X is methylene, an oxygen atom, a sulfur atom, an amino group or a substituted amino group; and n is an integer of 0 or 1.

Specific examples of $R^1$ include alkyl groups such as methyl, ethyl and isopropyl, aralkyl groups such as benzyl and 1-naphthylmethyl, alkenyl groups such as vinyl and cyclohexenyl, aryl groups such as phenyl and naphthyl and heterocyclic moieties such as furyl, thienyl and iondolyl. Further, $R^1$ may have a substituent, and specific examples of the substituent include the above alkyl groups, alkoxy groups such as methoxy, ethoxy and n-hexyloxy, alkylthio groups such as methylthio and n-hexylthio, aryloxy groups such as phenoxy and 1-naphthyloxy, arylthio groups such as phenylthio, halogen atoms such as chlorine and bromine, di-substituted amino groups such as dimethylamino and diphenylamino, the above aryl groups, the above heterocyclic moieties, carboxyalkyl groups such as carboxyl and carboxymethyl, sulfonylalkyl groups such as sulfonylpropyl, acidic groups such as a phosphoric acid group and a hydroxamic acid group and electron-attracting groups such as cyano, nitro and trifluoromethyl. Further, $R^1$ may bond to a benzene ring to form a cyclic structure, and specific examples thereof are as shown in (1) to (9). Specific examples of $R^2$ and $R^3$ include a hydrogen atom, the above alkyl groups, the above alkoxy groups, the above alkylthio groups, mono-substituted amino groups such as methylamino and anilino, the above aralkyl groups, the above alkenyl groups, the above aryl groups and the above heterocyclic moieties. Further, $R^2$ may have a substituent, and specific examples thereof include the above alkyl groups, alkoxy groups such as methoxy, ethoxy and n-hexyloxy, alkylthio groups such as methylthio and n-hexylthio, aryloxy groups such as phenoxy and 1-naphthyloxy, arylthio groups such as phenylthio, halogen atoms such as chlorine and bromine, di-substituted amino groups such as dimethylamino and diphenylamino, the above aryl groups, the above heterocyclic moieties, a carboxyl group, carboxyalkyl groups such as carboxylmethyl, sulfonylalkyl groups such as sulfonylpropyl, acidic groups such as a phosphoric acid group and a hydroxamic acid group, and electron-attracting groups such as cyano, nitro and trifluoromethyl. Further, $R^2$ and $R^3$ may bond to form a cyclic structure, and specific examples thereof are as shown in (10) to (20). Specific examples of $R^4$ are as shown in (21) to (46). However, the specific examples shall not be limited thereto.

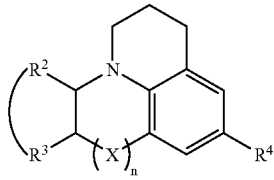

(1)

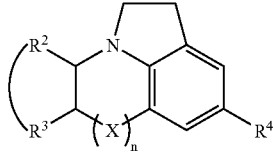

(2)

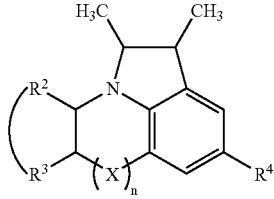

(3)

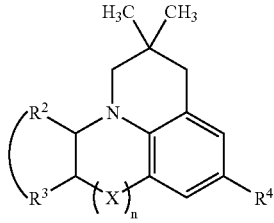

(4)

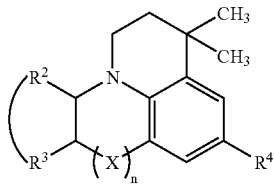

(5)

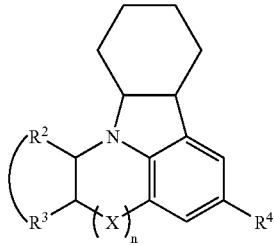

(6)

—COOH  (21)
—SO₂OH  (22)
—PO₃OH  (23)
—CONHOH  (24)

$$-\underset{H}{C}=\underset{H}{C}-COOH \quad (25)$$

$$-\underset{H}{C}=C\underset{COOH}{\overset{COOH}{-}} \quad (26)$$

$$-\underset{H}{C}=C\underset{COOH}{\overset{CN}{-}} \quad (27)$$

$$-\underset{H}{C}=\underset{H}{C}-\underset{H}{C}=\underset{H}{C}-COOH \quad (28)$$

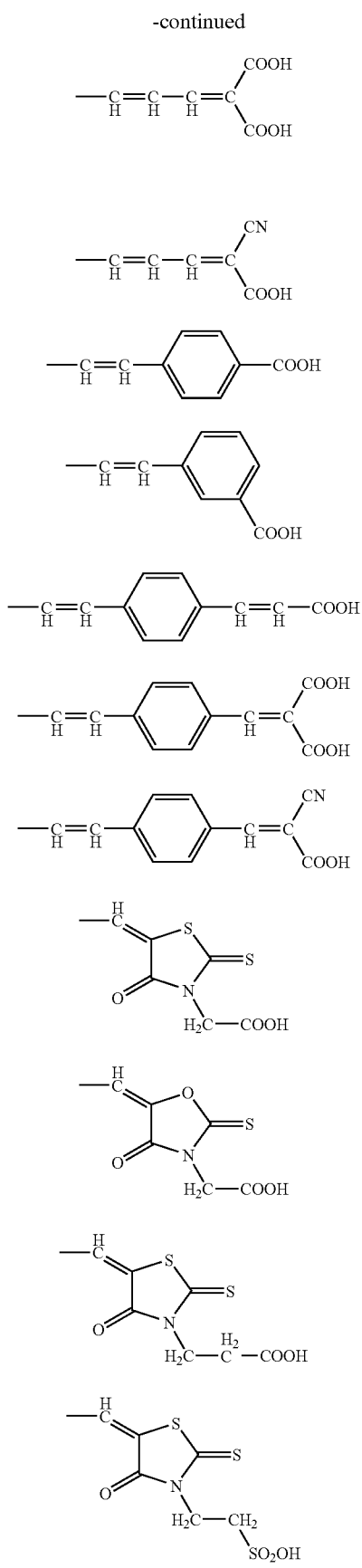
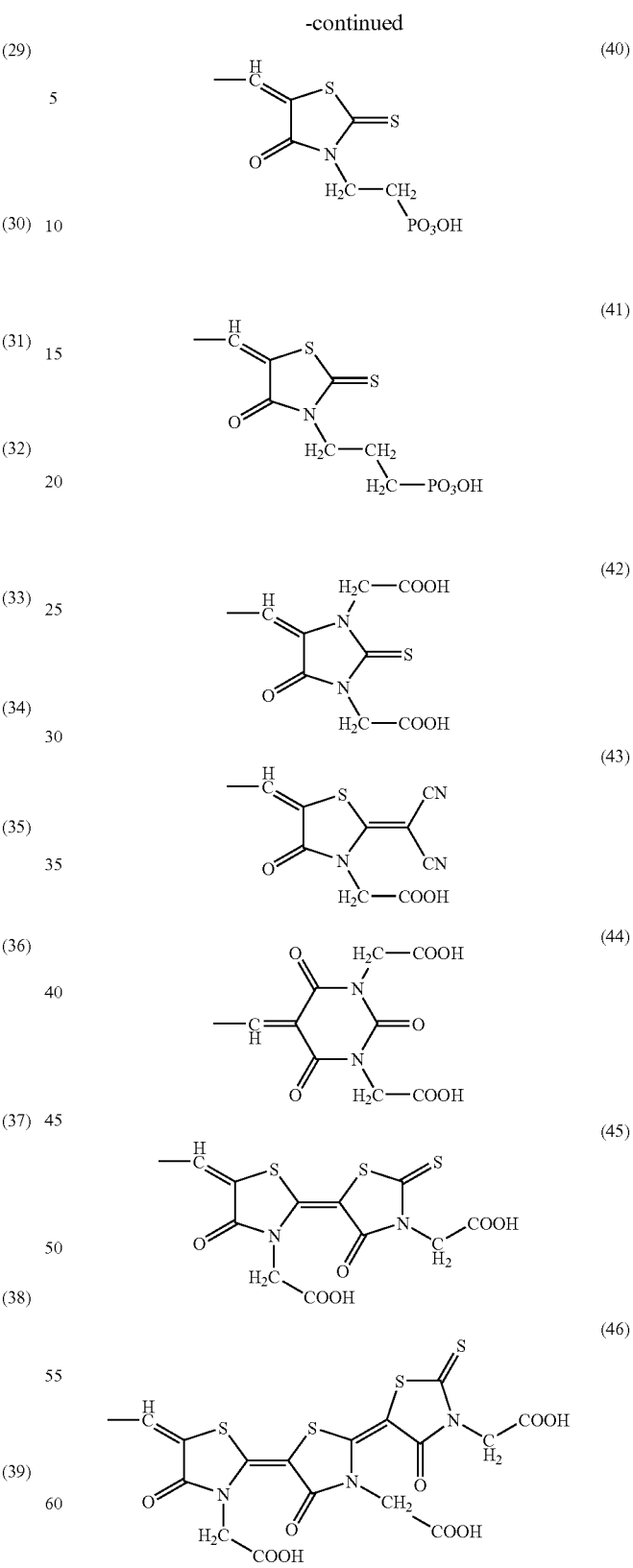
Specific examples of the dye I of the present invention are as shown in A-1 to A-23, while the dye I shall not be limited thereto.

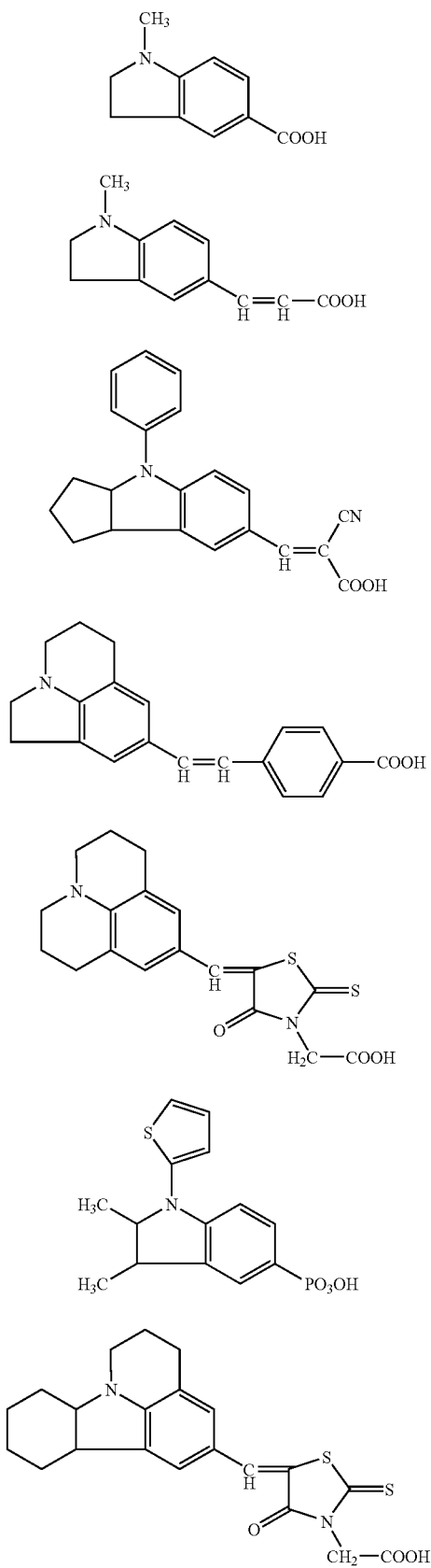
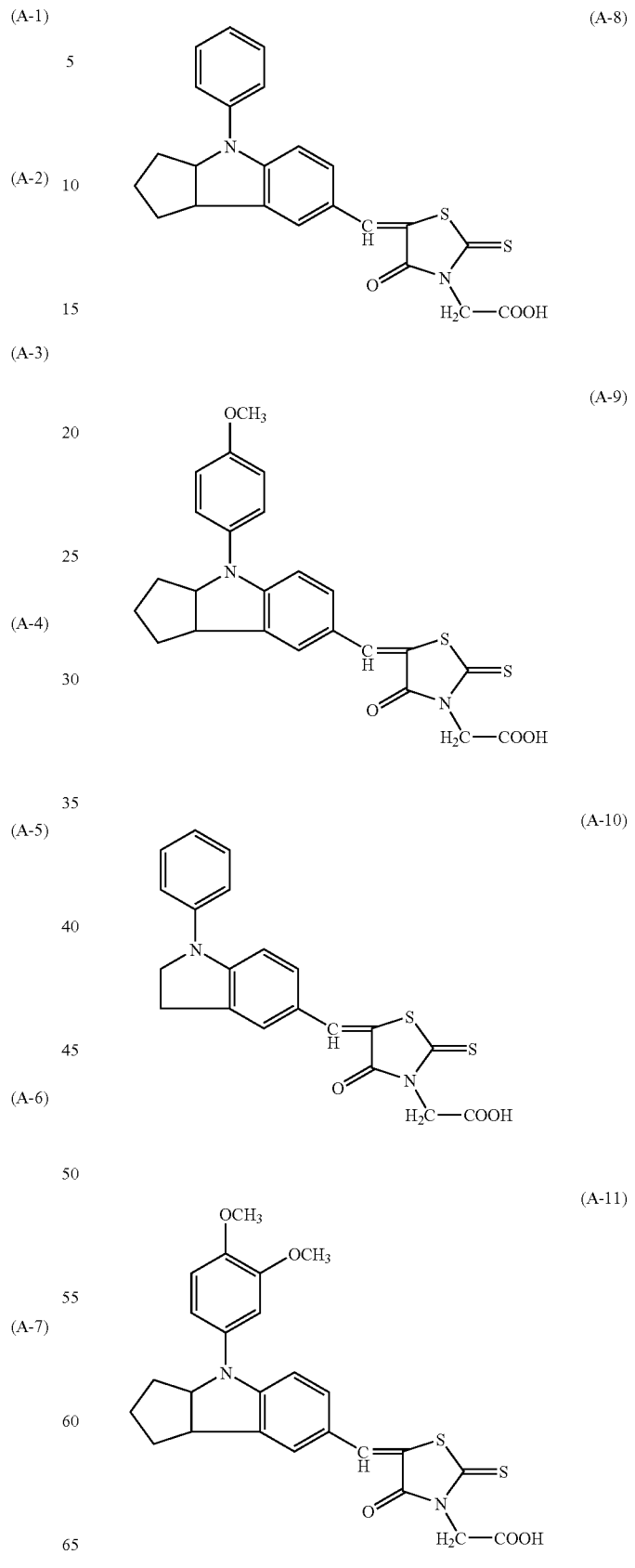

-continued
(A-12) 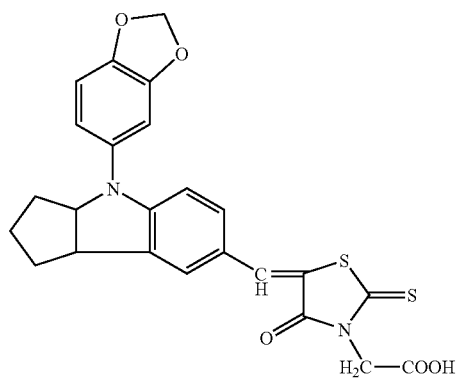
(A-13) 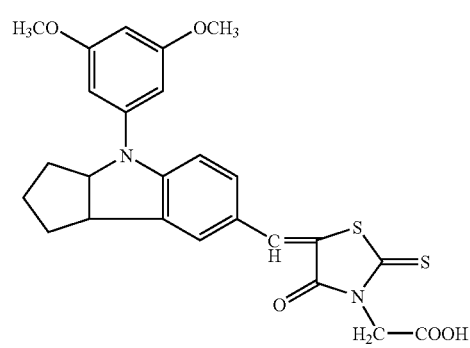
(A-14) 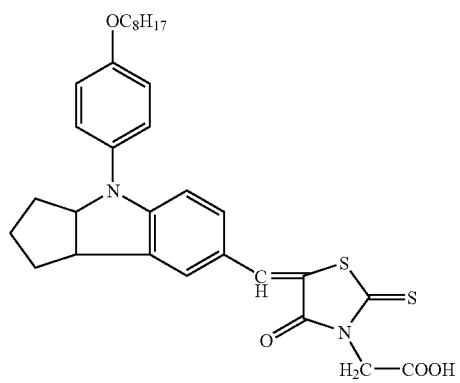
(A-15) 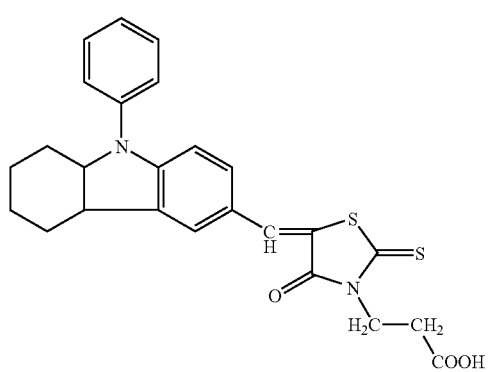
-continued
(A-16) 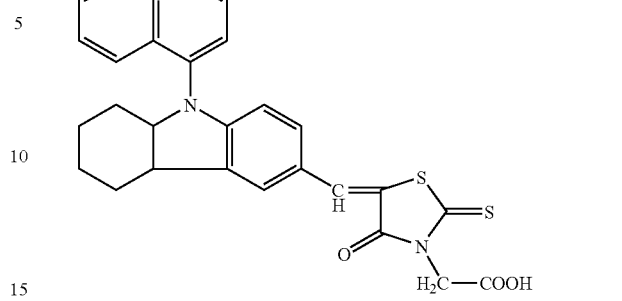
(A-17) 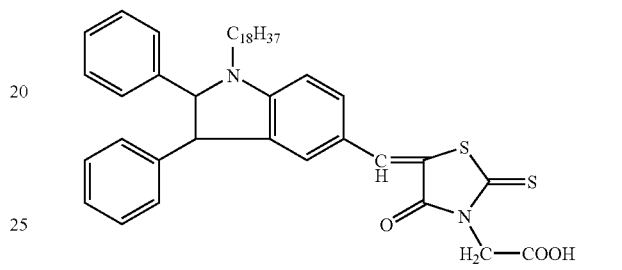
(A-18) 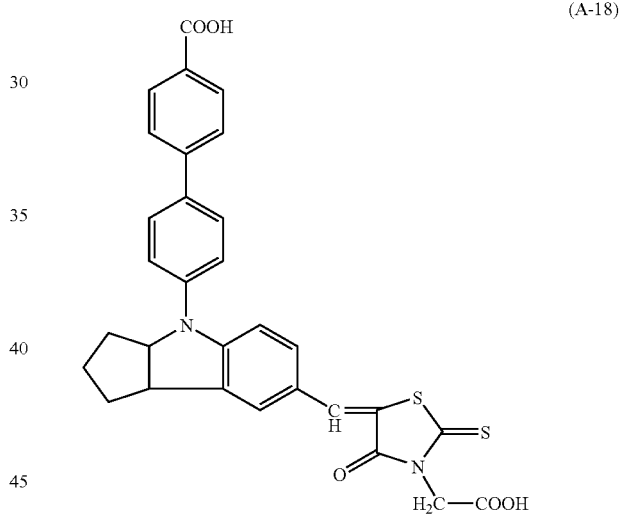
(A-19) 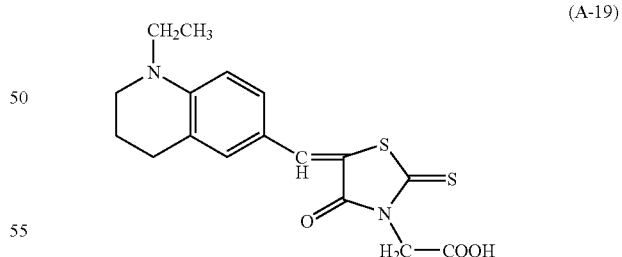
(A-20) 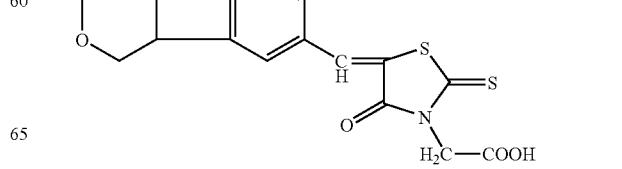

-continued

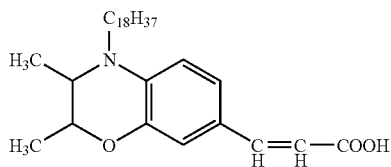
(A-21)

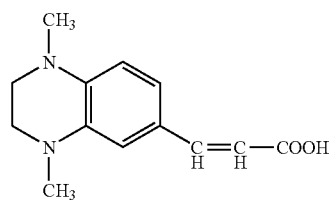
(A-22)

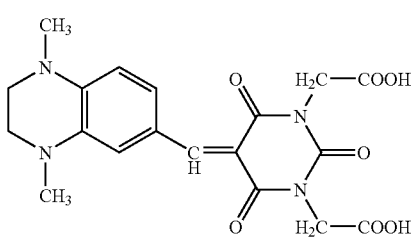
(A-23)

The dye II of the present invention is a merocyanine dye having a structure represented by the general formula (II).

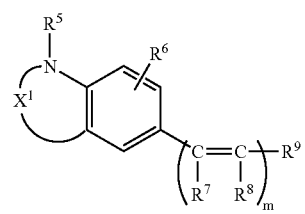
(II)

In the general formula (II), $R^5$ is an alkyl group, an aralkyl group, an alkenyl group, an aryl group or a heterocyclic moiety and may have a substituent. $R^6$ is an alkyl group, an alkoxy group or a halogen atom and may have a substituent. Each of $R^7$ and $R^8$ is a hydrogen atom, an alkyl group, an alkoxy group, an alkylthio group, an aryl group, an aryloxy group, an arylthio group or a heterocyclic moiety, and may have a substituent. $R^9$ is a substituent having an acidic group. $X^1$ is a binding group that forms a cyclic structure together with an amino group. m is 0 or 1, and a carbon-carbon double bond may be any one of E form and Z form, The merocyanine dye of the general formula (II) preferably includes a compound of the general formula (II-1),

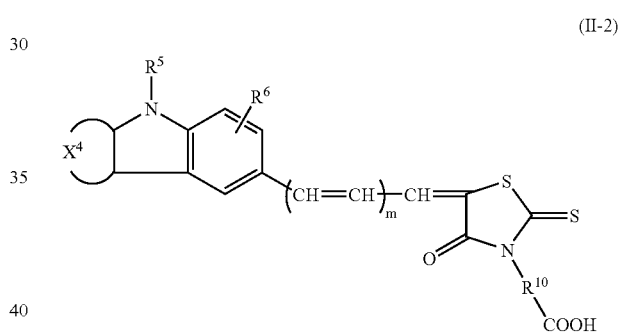
(II-1)

in which $R^5$ is an alkyl group, an aralkyl group, an alkenyl group, an aryl group or a heterocyclic moiety and may have a substituent, $R^6$ is an alkyl group, an alkoxy group or a halogen atom and may have a substituent; $R^{10}$ is a divalent alkylene group or a divalent arylene group and may have a substituent; $X^1$ is a binding group that forms a cyclic structure together with an amino group; $X^2$ is an oxygen atom or a sulfur atom; $X^3$ is an oxygen atom, a sulfur atom or a dicyanomethylene group; m is 0 or 1 and a carbon-carbon double bond may be any one of E form and Z form, and a compound of the general formula (II-2), (II-2)

in which $R^5$ is an alkyl group, an aralkyl group, an alkenyl group, an aryl group or a heterocyclic moiety and may have a substituent; $R^6$ is an alkyl group, an alkoxy group or a halogen atom and may have a substituent; $X^4$ is a divalent alkylene group that forms a 5- to 7-membered ring; $R^{10}$ is a divalent alkylene group or a divalent arylene group and may have a substituent; m is 0 or 1, and a carbon-carbon double bond may be any one of E form or Z form.

In the general formula (II), specific examples of $R^5$ include alkyl groups such as methyl, ethyl and isopropyl, aralkyl groups such as benzyl and 1-naphthylmethyl, alkenyl groups such as vinyl and cyclohexenyl, aryl groups such as phenyl and naphthyl and heterocyclic moieties such as furyl, thienyl and indolyl. Further, $R^5$ may have a substituent, and specific examples thereof include the above alkyl groups, alkoxy groups such as methoxy, ethoxy and n-hexyloxy, alkylthio groups such as methylthio and n-hexylthio, aryloxy groups such as phenoxy and 1-naphthyloxy, arylthio groups such as phenylthio, halogen atoms such as chlorine and bromine, di-substituted amino groups such as dimethylamino and diphenylamino, the above aryl groups, the above heterocyclic moieties, a carboxyl group, carboxyalkyl groups such as carboxymethyl, sulfonylalkyl groups such as sulfonylpropyl, acidic groups such as a phosphoric acid group and a hydroxamic acid group, and electron-attracting groups such as cyano, nitro and trifluoromethyl. Specific examples of $R^6$ include the above alkyl groups, the above alkoxy groups and the above halogen atoms. Further, $R^6$ may have a substituent, and specific examples thereof include the above alkyl groups, the above alkoxy groups, the above halogen atoms and the above aryl groups. Specific examples of $R^7$ and $R^8$ include a hydrogen atom, the above alkyl groups, the above alkoxy groups, the above alkylthio groups, the above aryl groups, the above aryloxy group, the above arylthio groups and the above heterocyclic moieties. Further, $R^7$ and $R^8$ may have a substituent, and specific examples thereof include the above alkyl groups, the above alkoxy group, the above aryl groups and the above heterocyclic groups. Specific examples of $X^1$ are as shown in (47) to (63). Specific examples of $R^9$ are as shown in (64) to (91). The specific examples shall not be limited thereto.

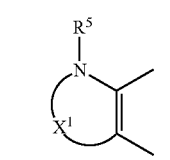

(47)

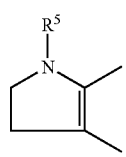

(48)

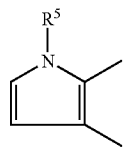

(49)

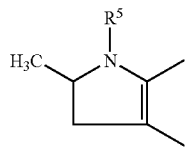

(50)

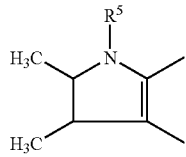

(51)

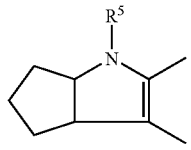

(52)

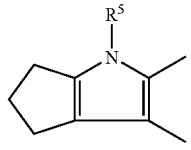

-continued

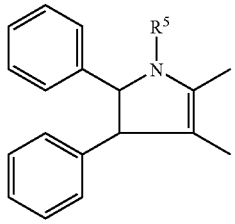

(53)

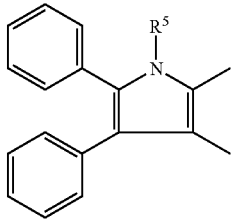

(54)

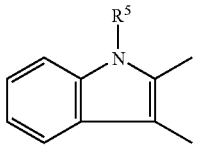

(55)

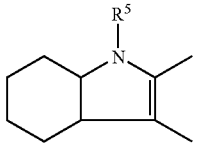

(56)

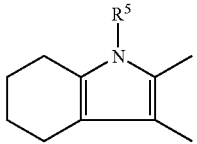

(57)

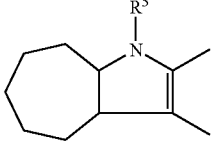

(58)

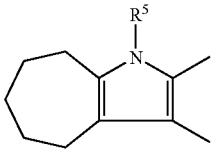

(59)

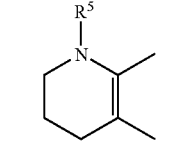

(60)

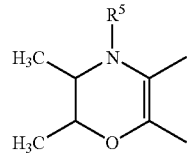

(61)

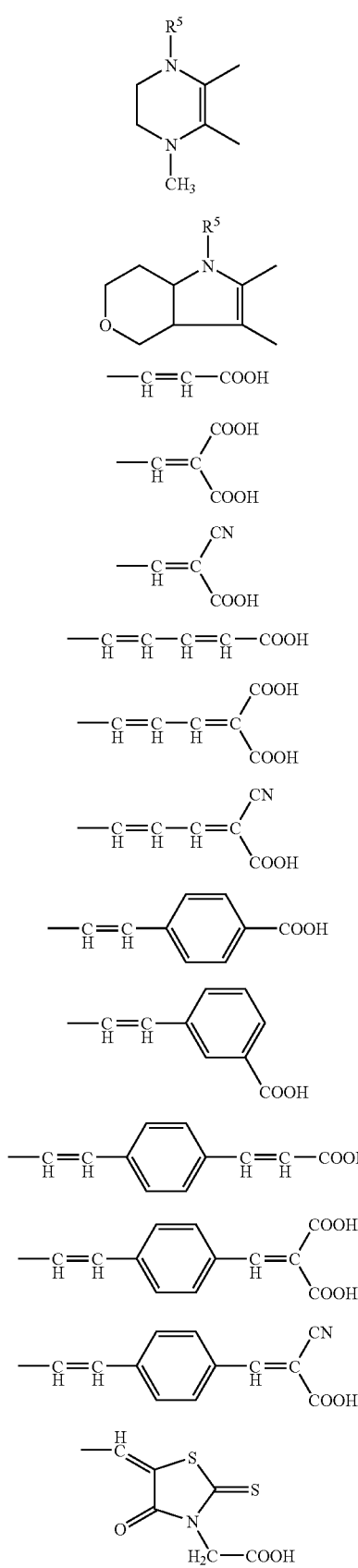
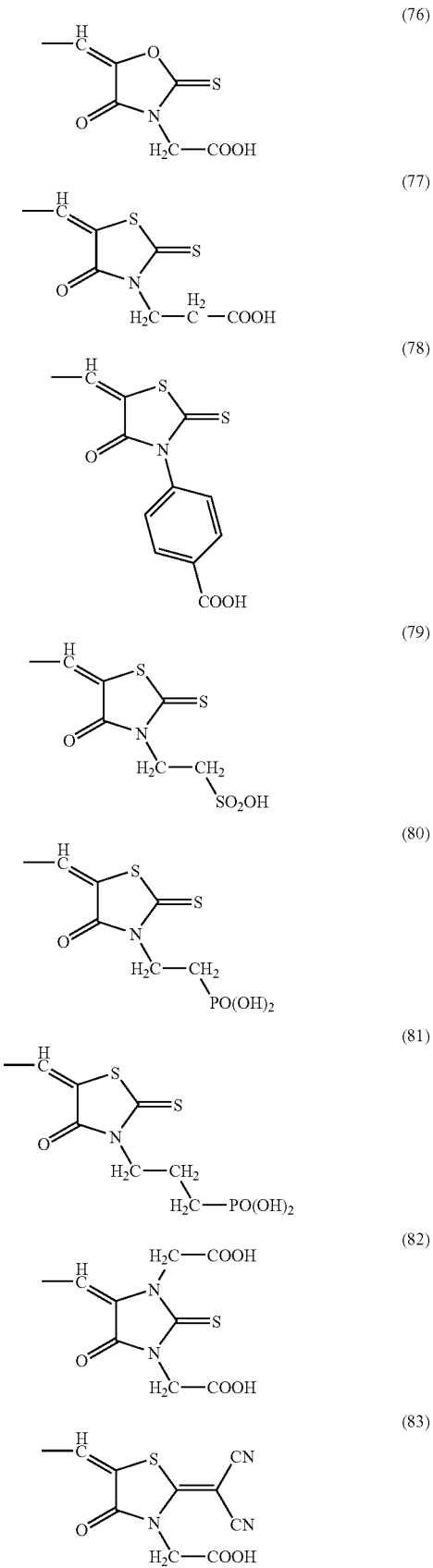

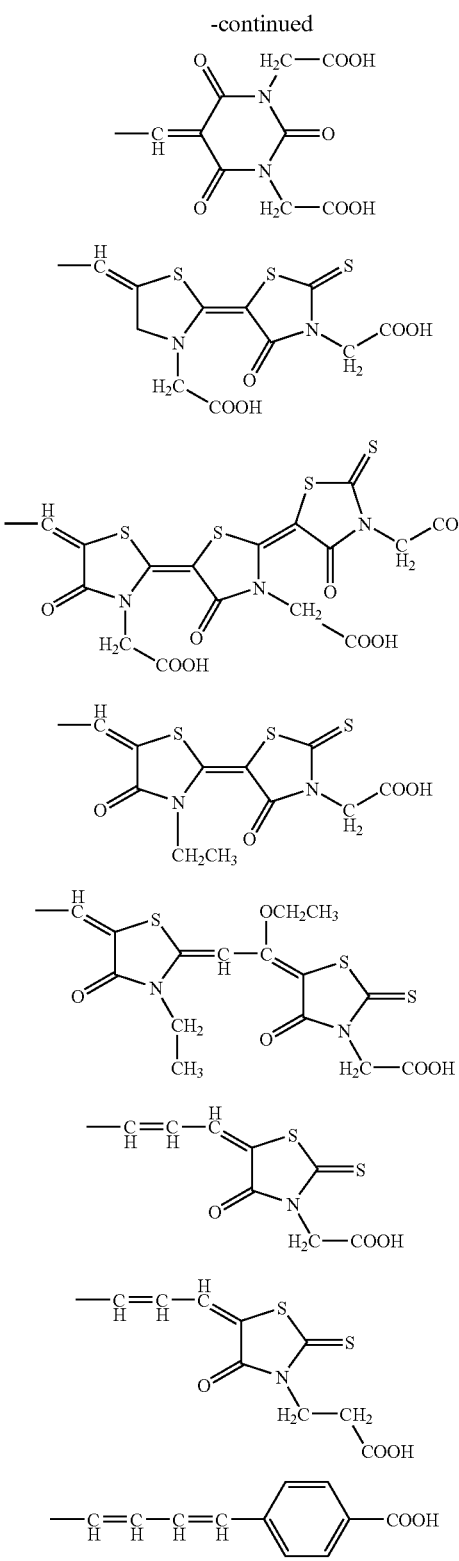

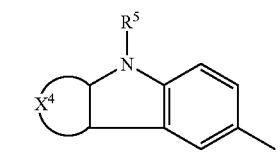

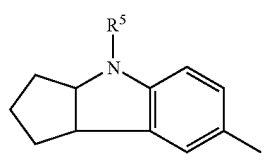

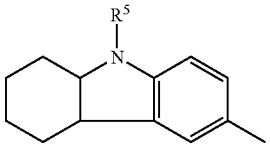

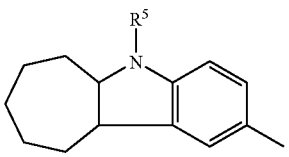

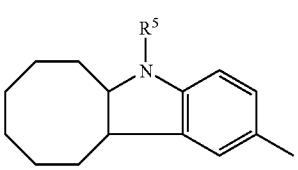

In the general formula (II-1), $R^5$, $R^6$ and $X^1$ are the same as those in the general formula (II). Specific examples of $X^2$ include an oxygen atom and a sulfur atom. Specific examples of $X^3$ include an oxygen atom, a sulfur atom and a dicyanomethylene group. Specific examples of $R^{10}$ include divalent alkylene groups such as a methylene group and an ethylene group and divalent arylene groups such as a 1,4-phenylene group and a 1,5-naphthylene group.

In the general formula (II-2), $R^5$ and $R^6$ are the same as those in the general formula (II). Further, $R^{10}$ is also the same as those in the general formula (II-1). Specific examples of $X^4$ are as shown in the following (92) to (95). Specific examples of $R^{10}$ include the above alkylene groups and the above arylene groups.

Specific examples of the merocyanine dye as the dye II of the present invention include compounds shown in B-1 to B-35, while the merocyanine dye shall not be limited thereto.

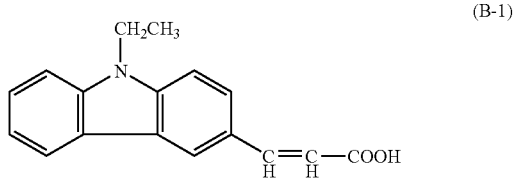

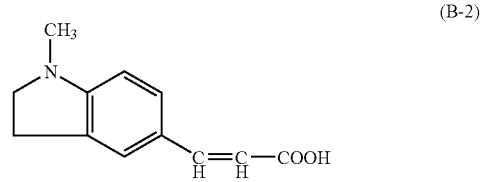

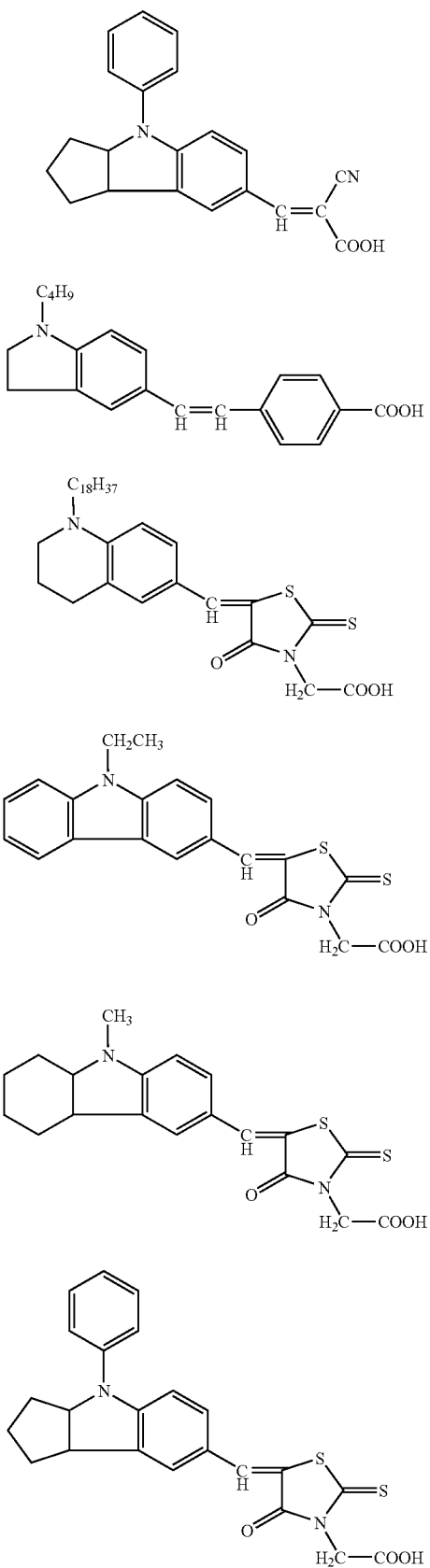
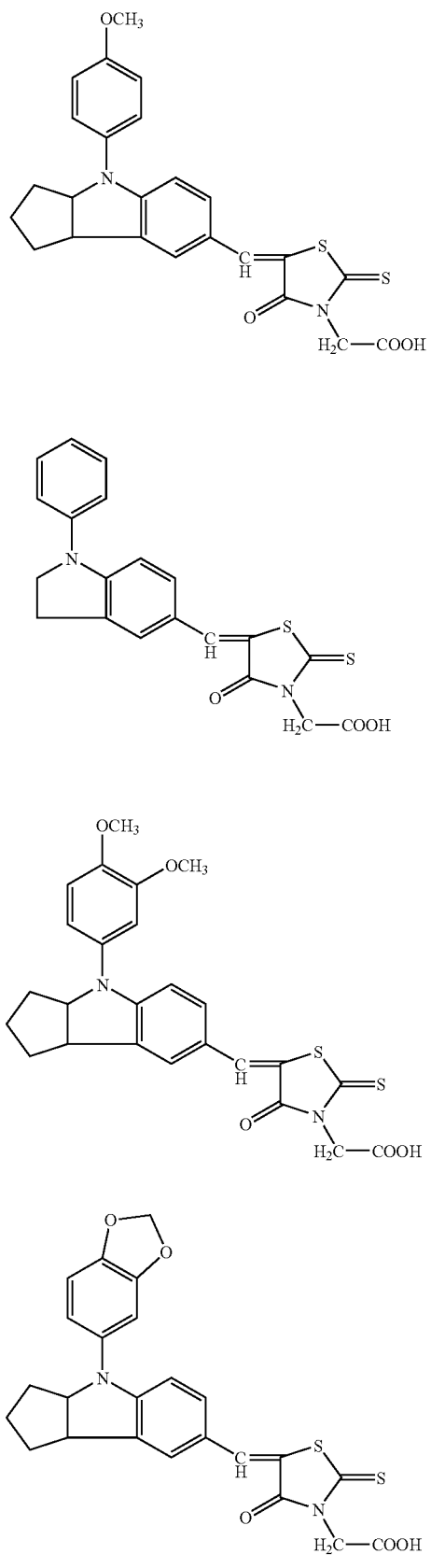

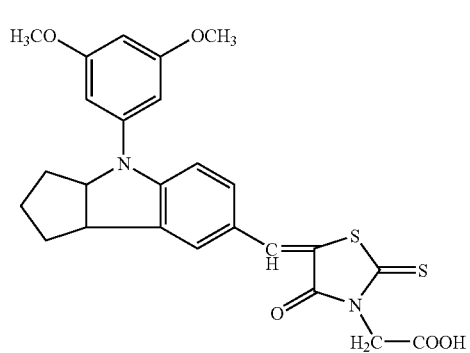
(B-13)
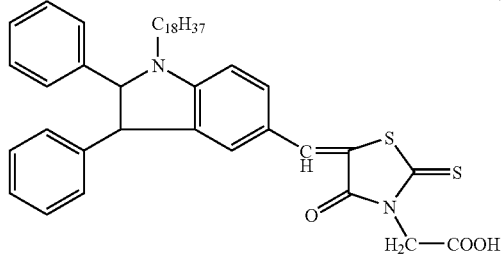
(B-17)
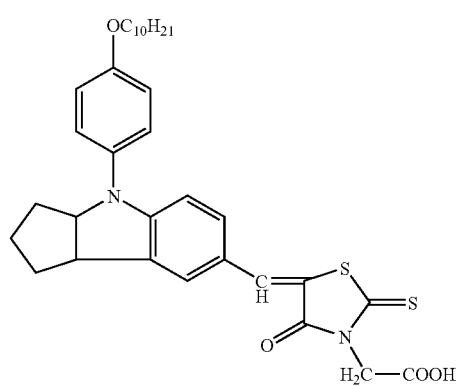
(B-14)
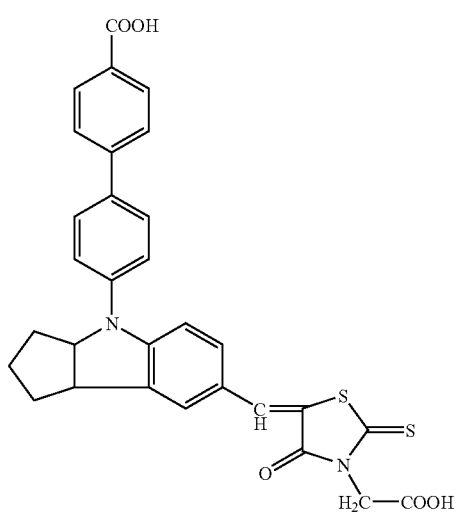
(B-18)
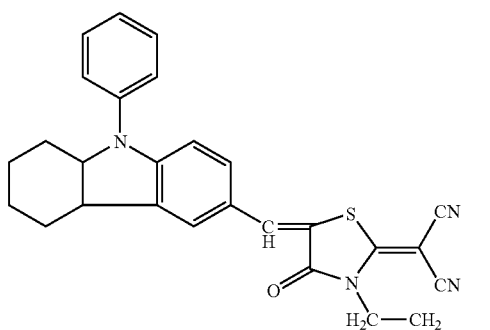
(B-15)
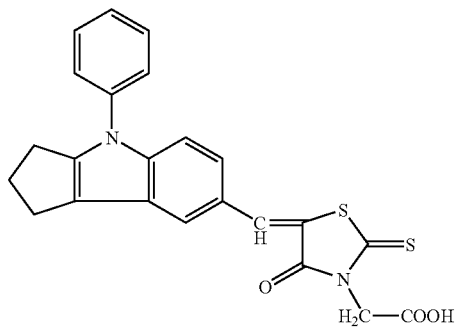
(B-19)
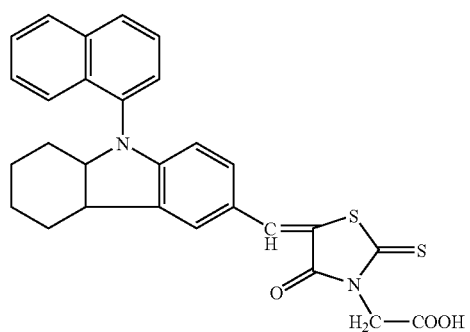
(B-16)
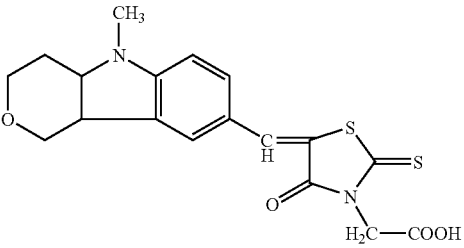
(B-20)
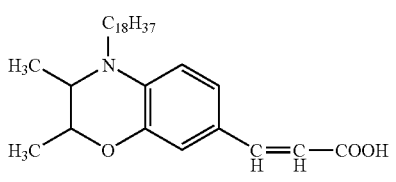
(B-21)

-continued (B-22)

(B-23)

(B-24)

(B-25)

(B-26)

(B-27)

(B-28)

(B-29)

(B-30)

(B-31)

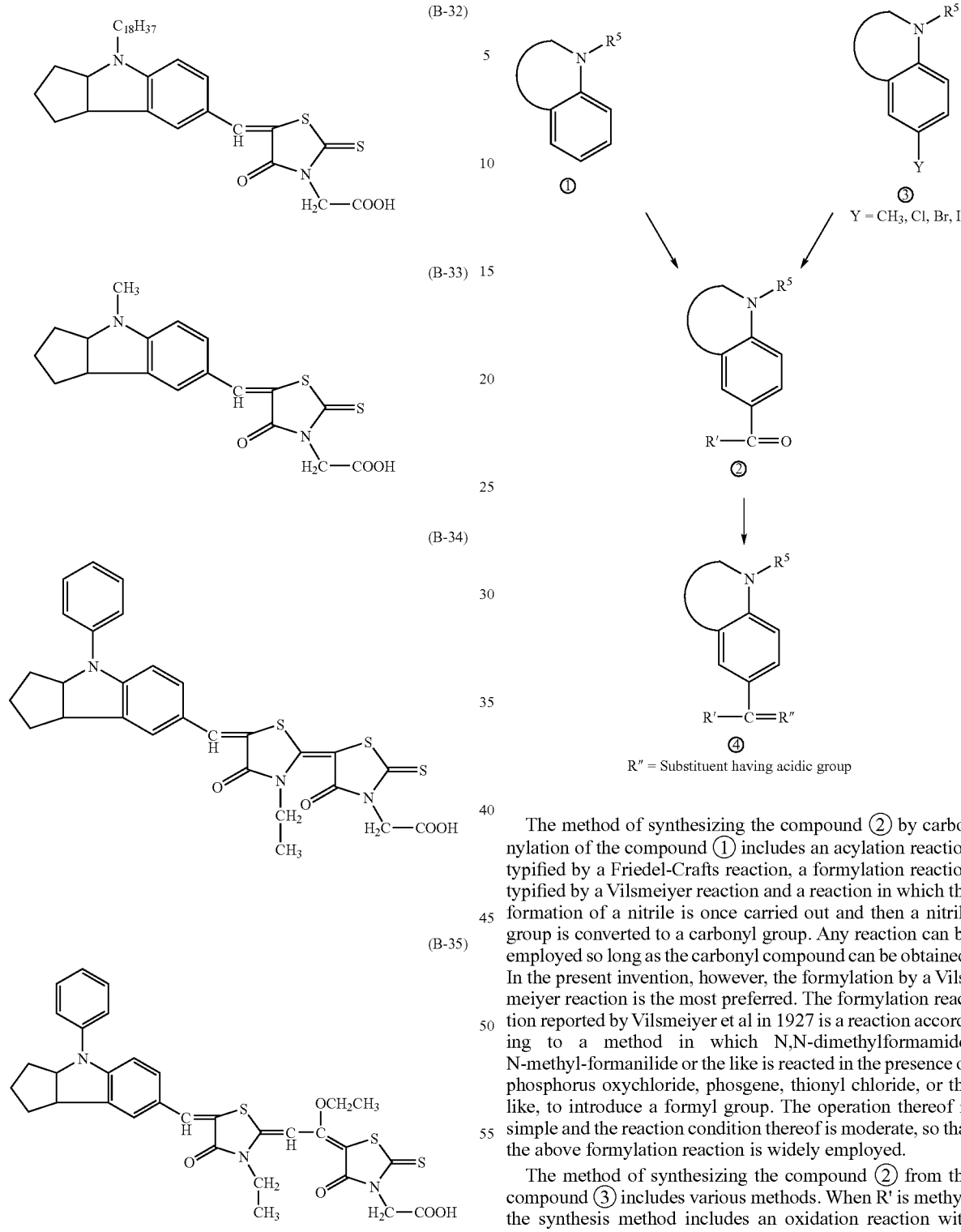

The scheme of synthesis of the merocyanine dye (II) of the present invention is as shown below. A compound ② is synthesized from a compound ① or compound ③, and then is reacted with a compound having an acidic group or an acidic group precursor, whereby an intended product ④ can be obtained.

The method of synthesizing the compound ② by carbonylation of the compound ① includes an acylation reaction typified by a Friedel-Crafts reaction, a formylation reaction typified by a Vilsmeiyer reaction and a reaction in which the formation of a nitrile is once carried out and then a nitrile group is converted to a carbonyl group. Any reaction can be employed so long as the carbonyl compound can be obtained. In the present invention, however, the formylation by a Vilsmeiyer reaction is the most preferred. The formylation reaction reported by Vilsmeiyer et al in 1927 is a reaction according to a method in which N,N-dimethylformamide, N-methyl-formanilide or the like is reacted in the presence of phosphorus oxychloride, phosgene, thionyl chloride, or the like, to introduce a formyl group. The operation thereof is simple and the reaction condition thereof is moderate, so that the above formylation reaction is widely employed.

The method of synthesizing the compound ② from the compound ③ includes various methods. When R' is methyl, the synthesis method includes an oxidation reaction with selenium dioxide, chromic acid, a hypo-halogen acid or the like, an oxidation reaction using dimethylsulfoxide, nitroalkane sodium salt, hexamethylenetetramine, or the like after conversion to halogenated methyl, a reaction using hydrolysis with an alkali or an acid after conversion to dihalogenated methyl. When R' is a halogen atom, the synthesis method includes a method in which a Grignard reagent or an organic lithium halogen atom is converted to Mg or Li, followed by formylation using formic acid ester or formamide as a formylation agent, and a method in which hydrogen and carbon monoxide are reacted in the present of a Pd catalyst.

The method of condensing the compound ② and a compound having an acidic group or acidic group precursor to obtain the intended product ④ includes a method in which the carbonyl compound and active methylene are reacted according to an aldol condensation or Knoevenagel reaction, and an olefin synthesis method based on Wittig reaction. The carbonyl compound and the active methylene are condensed in the presence of a base or an acid as a catalyst. Under some reaction conditions, a hydroxyl compound and an unsaturated compound formed by dehydration thereof are obtained. However, the unsaturated compound can be preferentially obtained by controlling the base or acid used for the reaction and the reaction temperature.

The Wittig reaction is remarkably superior for converting the carbonyl group to an olefin. Under alkaline conditions, generally, the reaction proceeds at a moderate temperature. In the present invention, the intermediate ② having a carbonyl group is reacted with a phosphorous acid diester having an acidic group or acidic group precursor, 2-(diethyoxyphosphenylimino)-1,3-dithiolane or phosphorous ylide, whereby the intended product can be easily obtained.

Further, the dye III of the present invention is a merocyanine dye having a structure represented by the general formula (IV).

(IV)

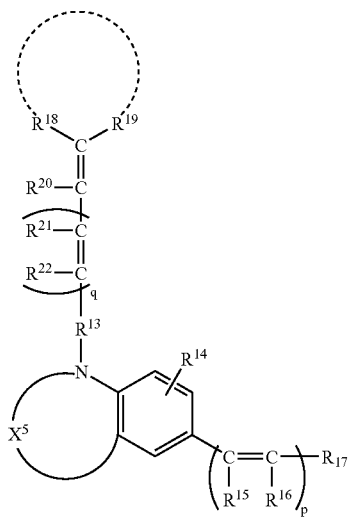

In the general formula (IV), $R^{13}$ is an arylene group or a heterocyclic moiety and may have a substituent; $R^{14}$ is a hydrogen atom, an alkyl group, an alkoxy group or a halogen atom; each of $R^{15}$ and $R^{16}$ is a hydrogen atom, an alkyl group, an alkoxy group, an alkylthio group a mono-substituted amino group, a di-substituted amino group, an aralkyl group, an alkenyl group, an aryl group or a heterocyclic moiety and may have a substituent; $R^{17}$ is a substituent having an acidic group; each of $R^{18}$ and $R^{19}$ is a hydrogen atom, an alkyl group, an aryl group or a heterocyclic moiety and may have a substituent, and $R^{18}$ and $R^{19}$ may bond directly or through a binding group; each of $R^{20}$, $R^{21}$ and $R^{22}$ is a hydrogen atom, an alkyl group, an alkoxy group, an aryl group or a heterocyclic moiety; $X^5$ is a binding group that forms a cyclic structure together with an amino group; p is an integer of 0 to 2; q is an integer of 0 to 2; and a carbon-carbon double bond may be any one of E form and Z form.

The above merocyanine dye represented by the above general formula (IV) is preferably a compound represented by the general formula (IV-1).

(IV-1)

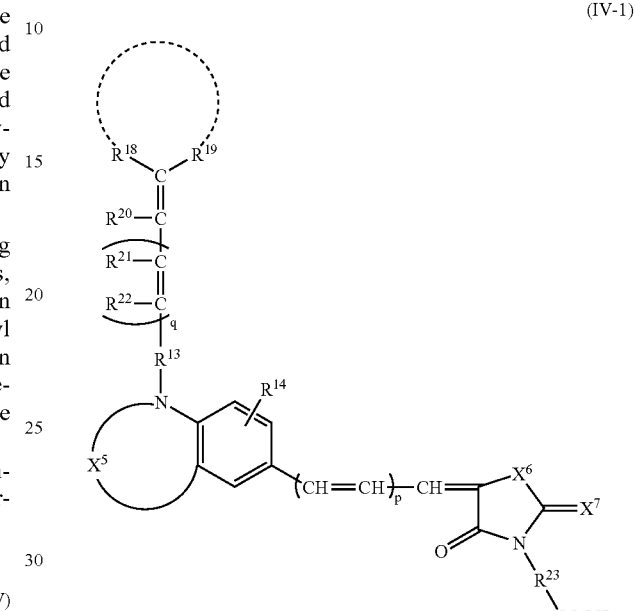

In the general formula (IV-1), $R^{13}$ is an arylene group or a heterocyclic moiety and may have a substituent; $R^{14}$ is a hydrogen atom, an alkyl group, an alkoxy group or a halogen atom; each of $R^{18}$ and $R^{19}$ is a hydrogen atom, an alkyl group, an aryl group or a heterocyclic moiety and may have a substituent and $R^{18}$ and $R^{19}$ may bond directly or through a binding group; each of $R^{20}$, $R^{21}$ and $R^{22}$ is a hydrogen atom, an alkyl group, an alkoxy group, an aryl group or a heterocyclic moiety; $R^{23}$ is an alkylene group or an arylene group; $X^5$ is a binding group that forms a cyclic structure together with an amino group; $X^6$ is an oxygen atom or a sulfur atom, and $X^7$ is an oxygen atom, a sulfur atom or a dicyanomethylene group; p is an integer of 0 to 2; q is an integer of 0 to 2; and a carbon-carbon double bond may be any one of E form and Z form.

Specific examples of $R^{13}$ include arylene groups such as a 1,4-phenylene group and a 2,6-naphthalene group and heterocyclic moieties such as a 2,5-thienylene group. $R^{13}$ may have a substituent, and specific examples thereof include alkyl groups such as methyl, ethyl and n-propyl, alkoxy groups such as methoxy, ethoxy and n-hexyloxy, alkylthio groups such as methylthio and n-hexylthio, aryloxy groups such as phenoxy and 1-naphthyloxy, arylthio groups such as phenylthio, halogen atoms such as chlorine and bromine, di-substituted amino groups such as dimethylamino and diphenyl amino, aryl groups such as phenyl, 4-methylphenyl and 2-naphthyl, heterocyclic moieties such as furyl and thienyl, a carboyl group, carboxyalkyl groups such as carboxymethyl, sulfonylalkyl groups such as sulfonylpropyl, acidic groups such as a phosphoric acid group and a hydroxamic acid group, and electron-attracting groups such as cyano, nitro and trifluoromethyl. Specific examples of $R^{14}$ include a hydrogen atom, the above alkyl groups, the above alkoxy groups and the above halogen atoms. Specific examples of $R^{15}$ and $R^{16}$ include a hydrogen atom, the above alkyl groups, the above alkoxy groups, the above alkylthio groups, mono-substituted amino groups such as methylamino and anilino, the above di-substituted amino groups, aralkyl groups such as benzyl, alkenyl groups such as vinyl, the above aryl groups and the above heterocyclic moieties. Specific examples of $R^{20}$, $R^{21}$ and $R^{22}$ include a hydrogen atom, the above alkyl groups, the above alkoxy groups, the above aryl groups and the above heterocyclic moieties. $X^5$ is a binding group that forms a cyclic structure with an amino group, and specific examples thereof are as shown in (96) to (112). $R^{17}$ is a substituent having an acidic group, and specific examples thereof are as shown in (113) to (140). Each of $R^{18}$ and $R^{19}$ includes a hydrogen atom, the above alkyl groups, the above aryl groups and the above heterocyclic groups, and specific examples thereof are as shown in (141) to (156). However, specific examples thereof shall not be limited thereto.

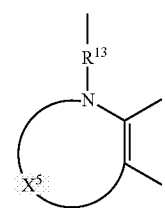

(96)

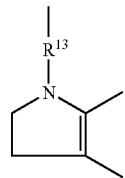

(97)

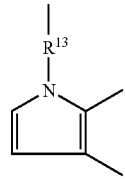

(98)

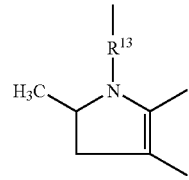

(99)

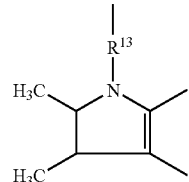

(100)

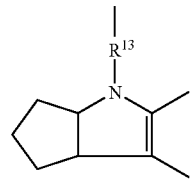

-continued

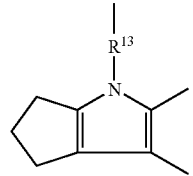

(101)

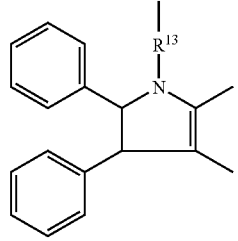

(102)

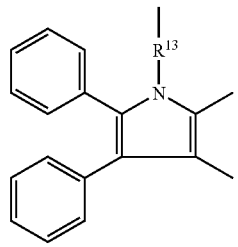

(103)

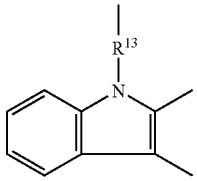

(104)

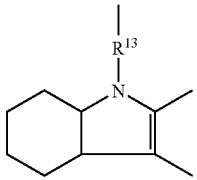

(105)

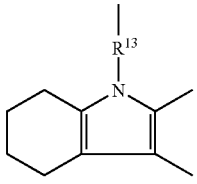

(106)

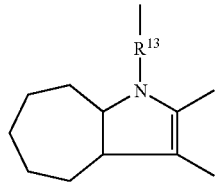

(107)

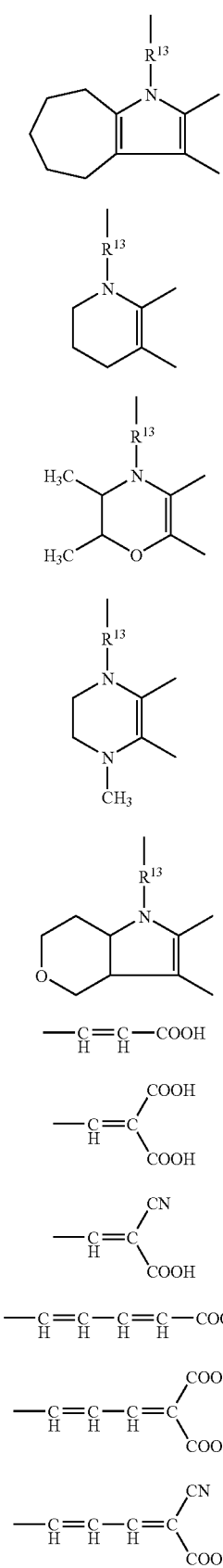
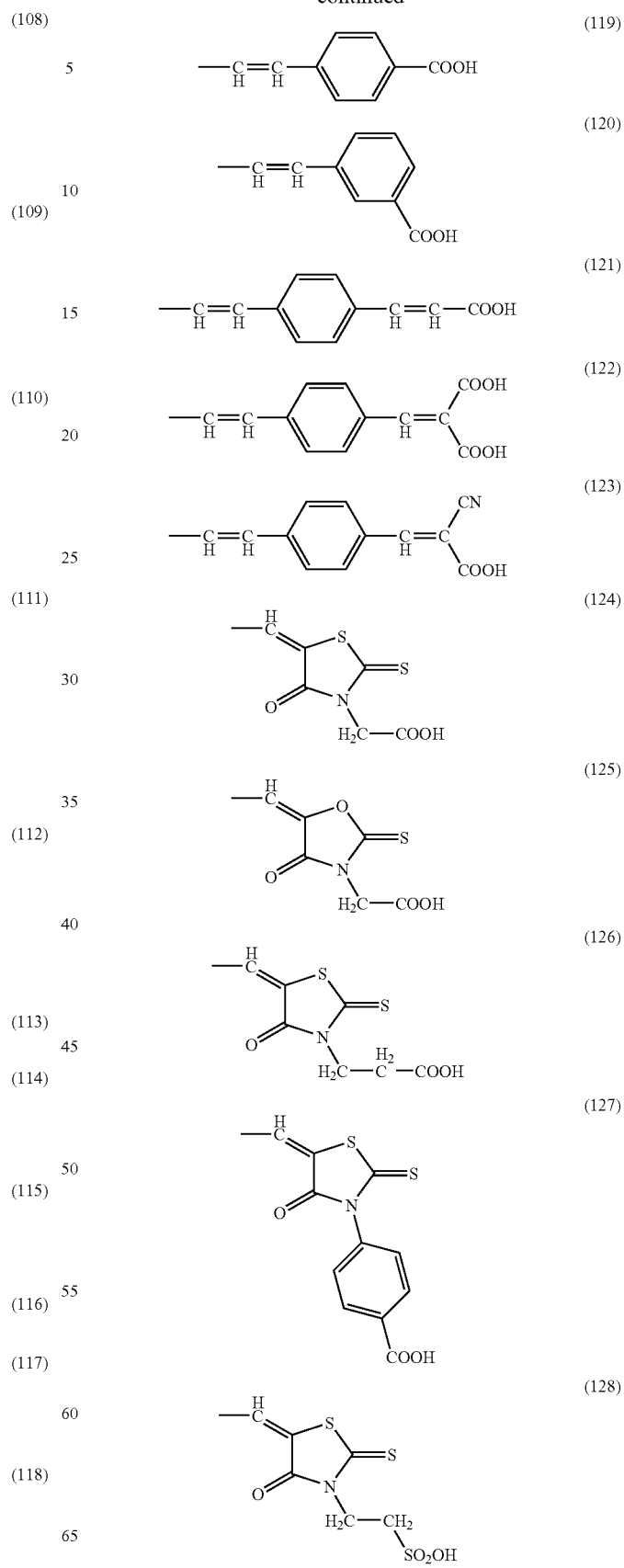

-continued (129) (130) (131) (132) (133) (134) (135) (136) (137) (138) (139) (140) (141) (142) (143) (144) (145) (146)

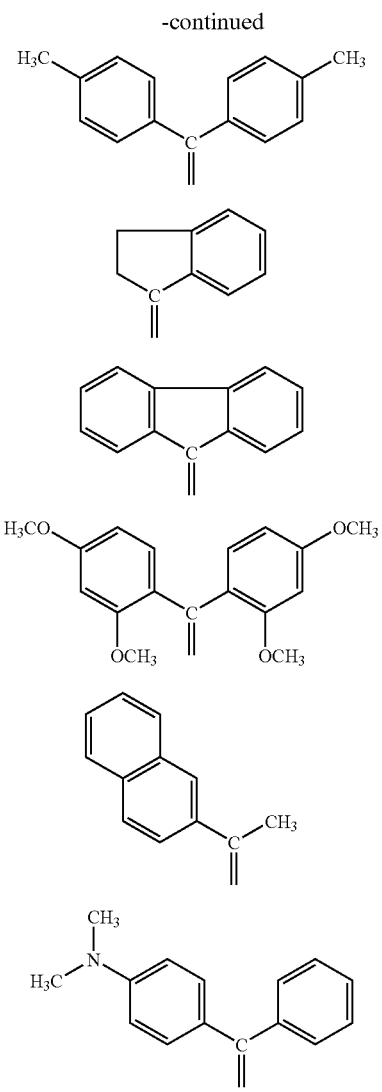
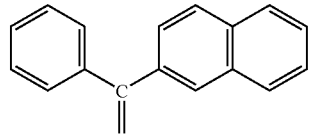
(147)
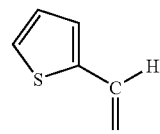
(154)
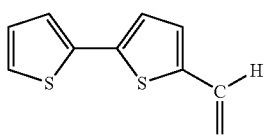
(155)
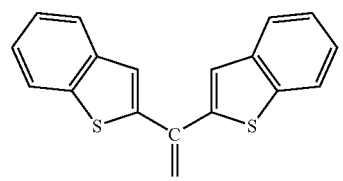
(156)
Specific examples of the merocyanine dye as the dye III of the present invention are as shown in (C-1) to (C-14), while the dye III shall not be limited thereto.
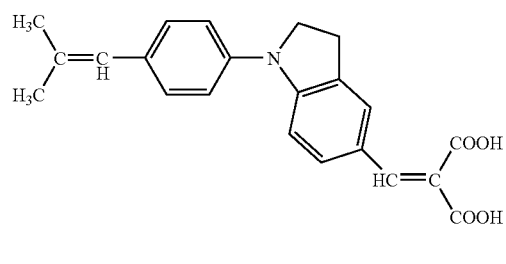

-continued
(C-3)
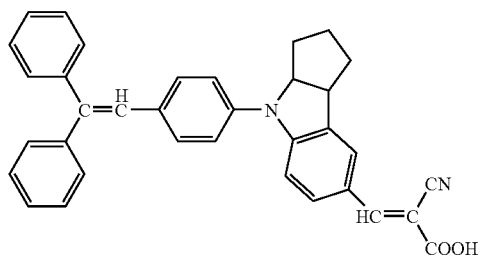
(C-4)
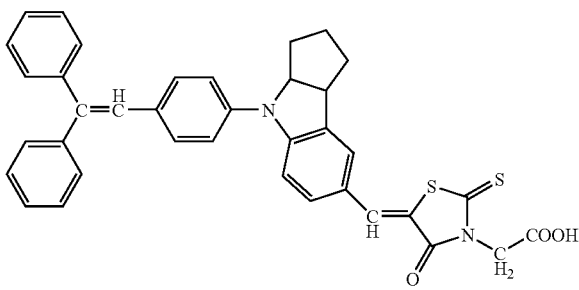
(C-5)
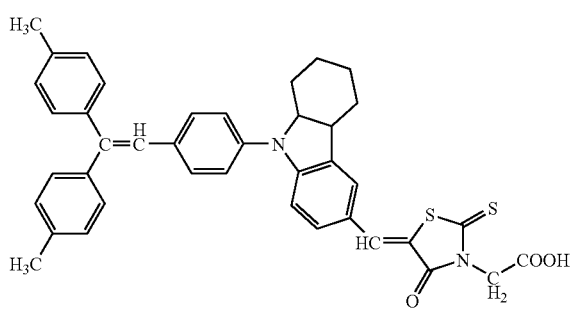
(C-6)
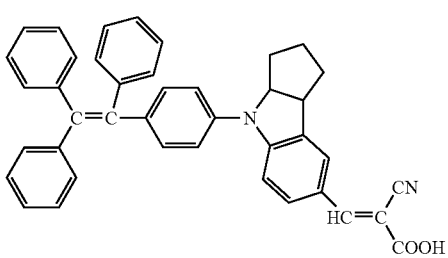
(C-7)
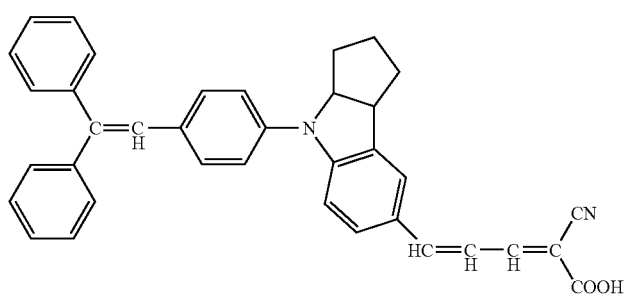
(C-8)
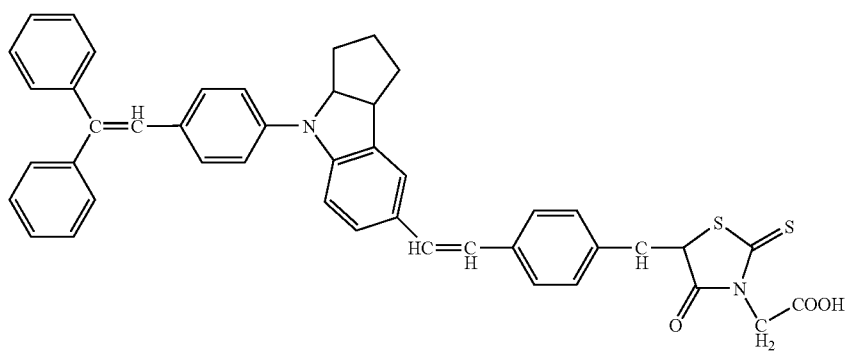
(C-9)
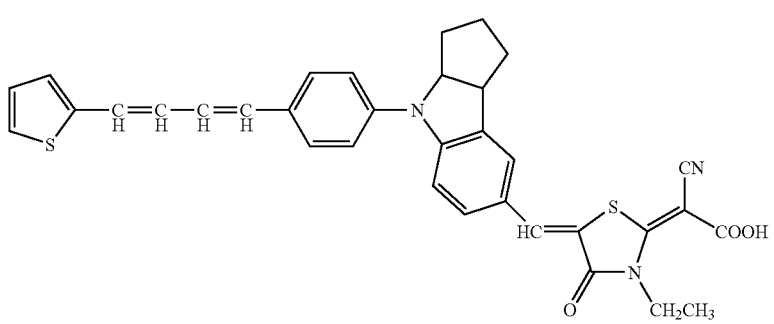

-continued
(C-10)
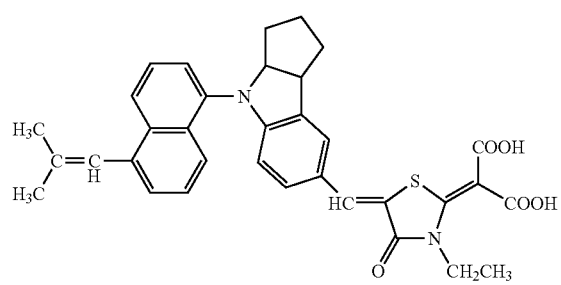
(C-11)
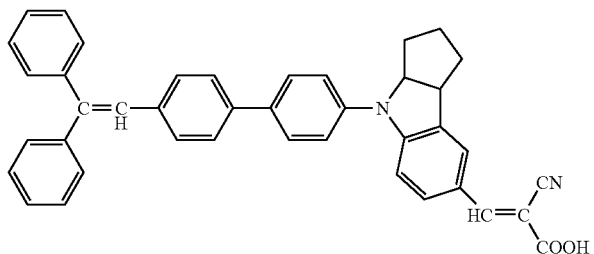
(C-12)
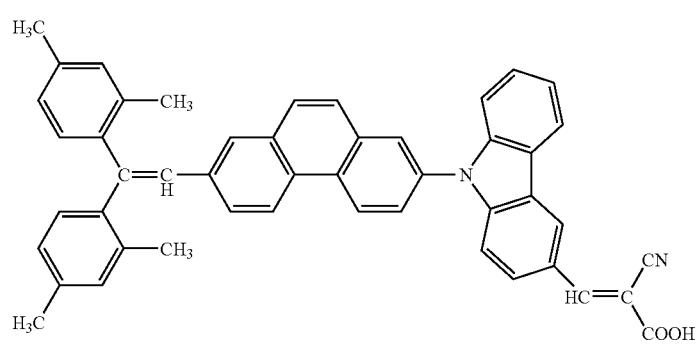
(C-13)
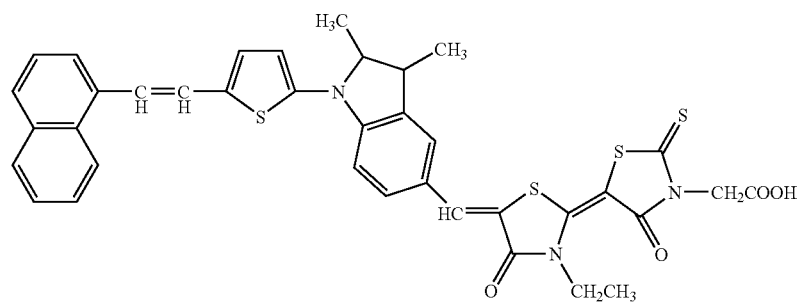
(C-14)
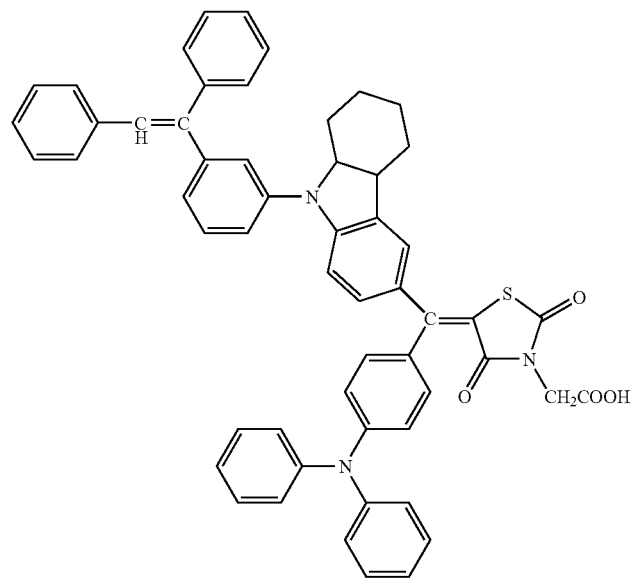

The dye IV of the present invention is a merocyanine dye having a structure represented by the general formula (V).

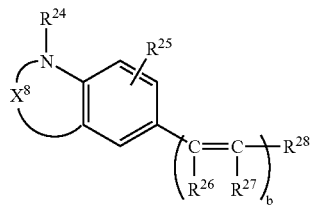
(V)

In the general formula (V), $R^{24}$ is an alkyl group, an aralkyl group, an alkenyl group, an aryl group or a heterocyclic moiety and may have a substituent; $R^{25}$ is an alkyl group, an alkoxy group or a halogen atom and may have a substituent; each of $R^{26}$ and $R^{27}$ is a hydrogen atom, an alkyl group, an alkoxy group, an alkylthio group, an aryl group, an aryloxy group, an arylthio group or a heterocyclic moiety and may have a substituent; $R^{28}$ is a quaternary ammonium salt of an acidic group, a metal salt of an acidic group, an amido group or a substituent having an ester group; $X^8$ is a binding group that forms a cyclic structure together with an amino group, b is 0 or 1; and a carbon-carbon double bond may be any one of E form and Z form.

Specific examples of $R^{24}$ include alkyl groups such as methyl, ethyl and isopropyl, aralkyl groups such as benzyl and 1-naphthylmethyl, alkenyl groups such as vinyl and cyclohexenyl, aryl groups such as phenyl and naphthyl and heterocyclic moieties such as furyl, thienyl and indolyl. Further, $R^{24}$ may have a substituent, and specific examples of the substituent include the above alkyl groups, alkoxy groups such as methoxy, ethoxy and n-hexyloxy, alkylthio groups such as methylthio and n-hexylthio, aryloxy groups such as phenoxy and 1-naphthyloxy, arylthio groups such as phenylthio, halogen atoms such as chlorine and bromine, di-substituted amino groups such as dimethylamino and diphenylamino, the above aryl groups, the above heterocyclic moieties, a carboxyl group, carboxyalkyl groups such as carboxymethyl, sulfonylalkyl groups such as sulfonylpropyl, acidic groups such as a phosphoric acid group and a hydroxamic acid group, and electron-attracting groups such as cyano, nitro and trifluoromethyl. Specific examples of $R^{25}$ include the above alkyl groups, the above alkoxy groups and the above halogen atoms. $R^{25}$ may have a substituent, and specific examples thereof include the above alkyl groups, the above alkoxy groups, the above halogen atoms and the above aryl groups. Specific examples of $R^{26}$ and $R^{27}$ include a hydrogen atom, the above alkyl groups, the above alkoxy groups, the above alkylthio groups, the above aryl groups, the above aryloxy groups, the above arylthio groups and the above heterocyclic moieties. $R^{26}$ and $R^{27}$ may have a substituent, and specific examples of the substituent include the above alkyl groups, the above alkoxy groups, the above aryl groups, the above heterocyclic moieties and the above halogen atoms. Specific examples of $X^8$ are as shown in (157) to (173). Specific examples of $R^{28}$ are as shown in (174) to (201). However, the specific examples shall not be limited thereto.

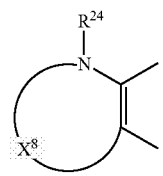
(157)

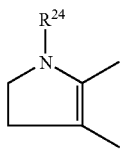
(158)

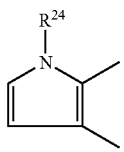
(159)

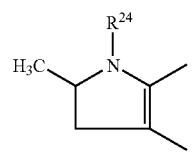
(160)

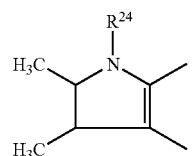
(161)

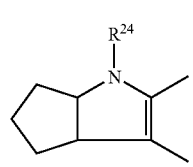
(162)

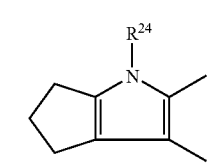
(163)

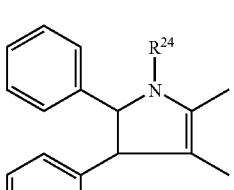
(164)

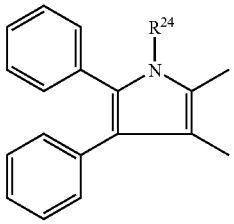

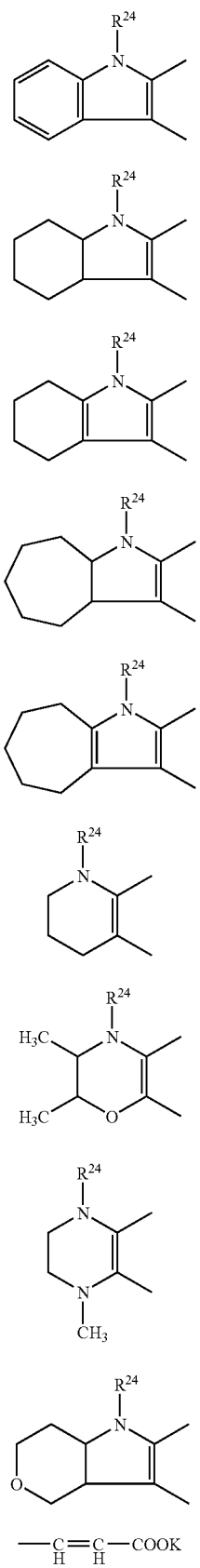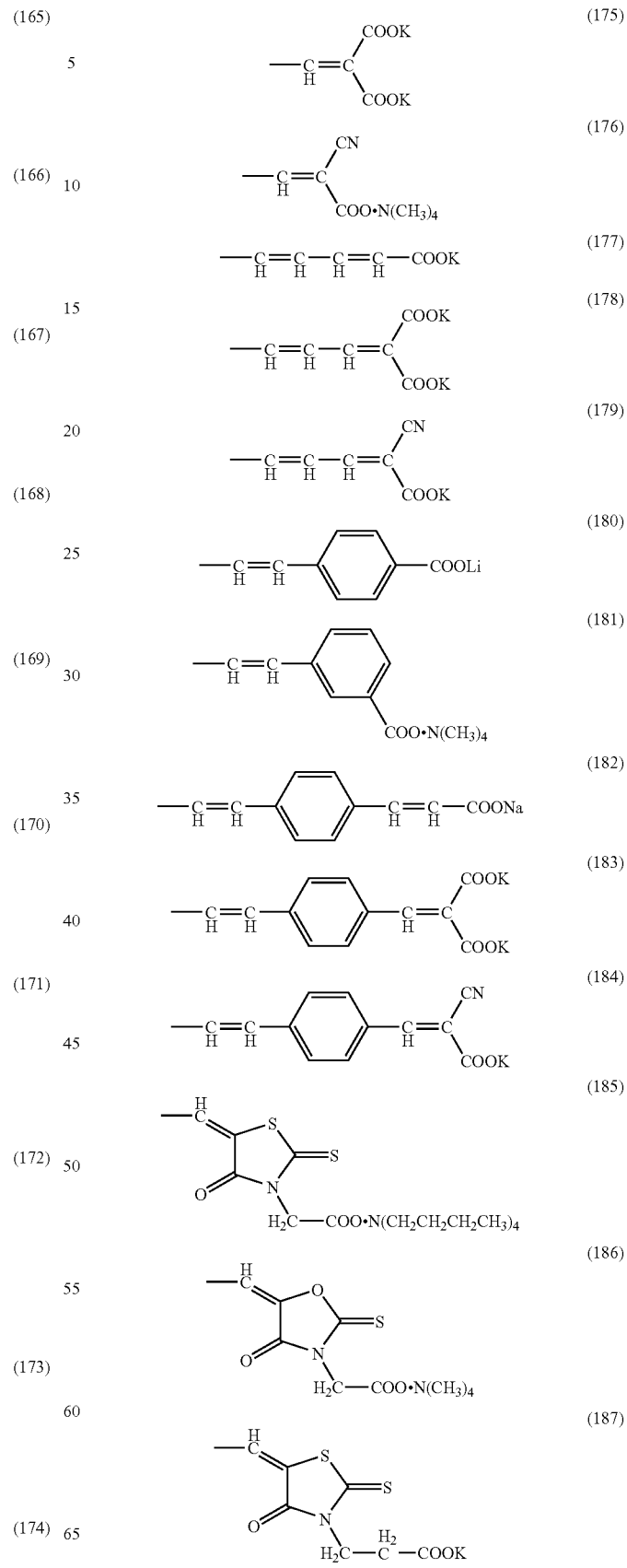

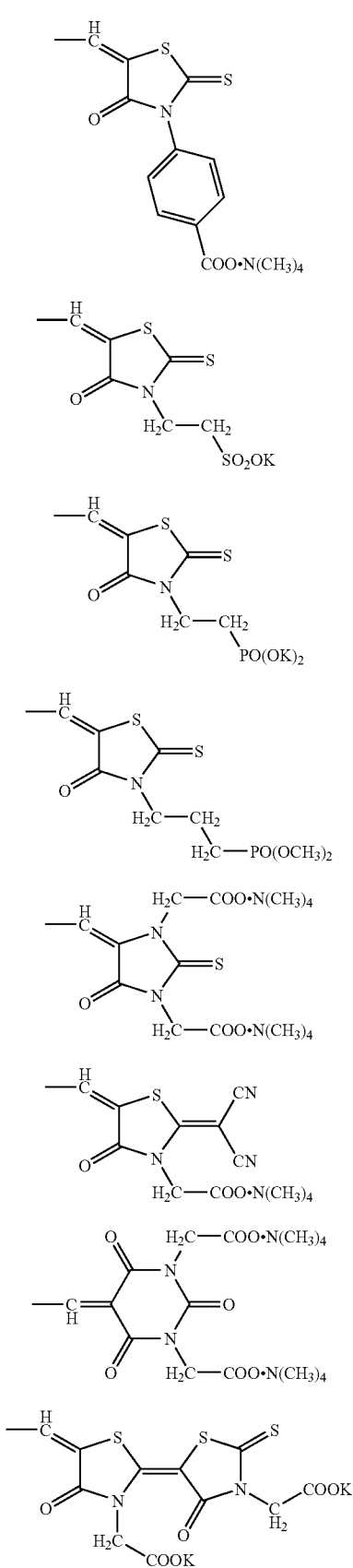
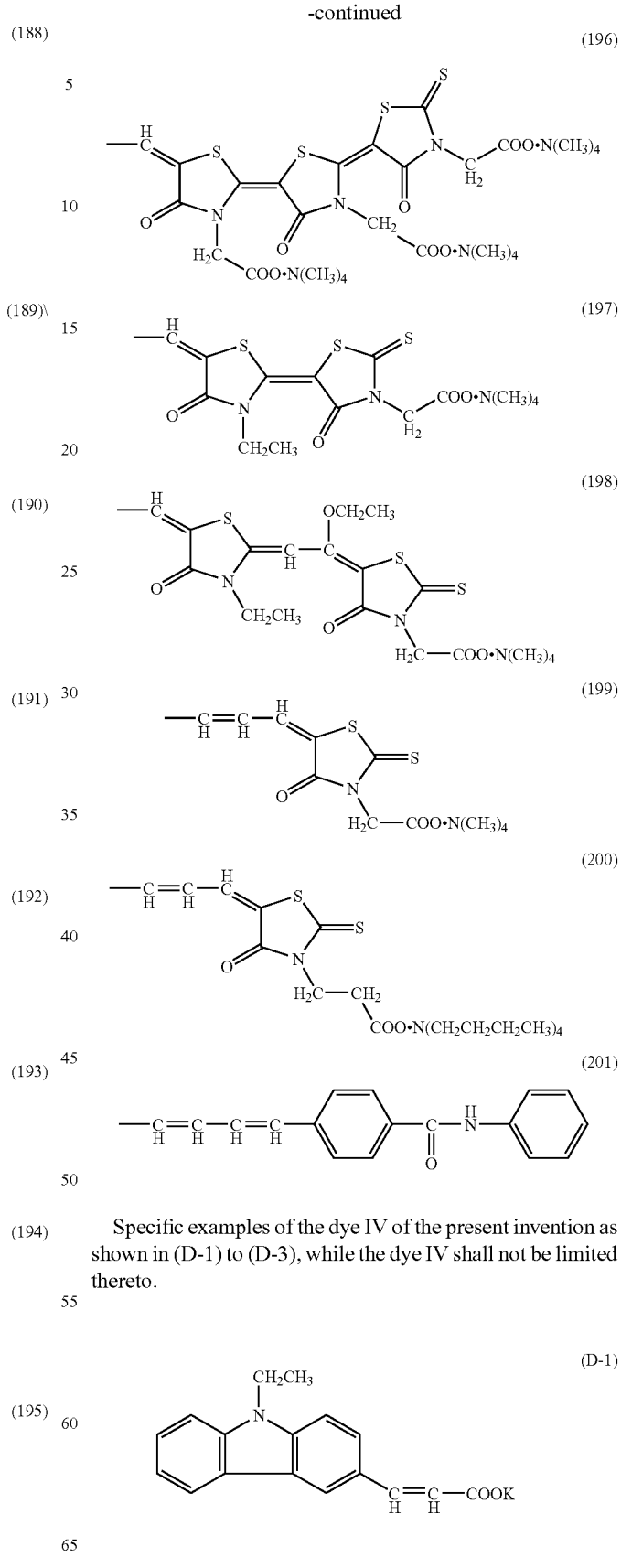
Specific examples of the dye IV of the present invention as shown in (D-1) to (D-3), while the dye IV shall not be limited thereto.

-continued
(D-2)
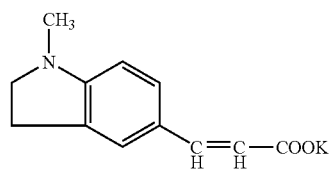
(D-3)
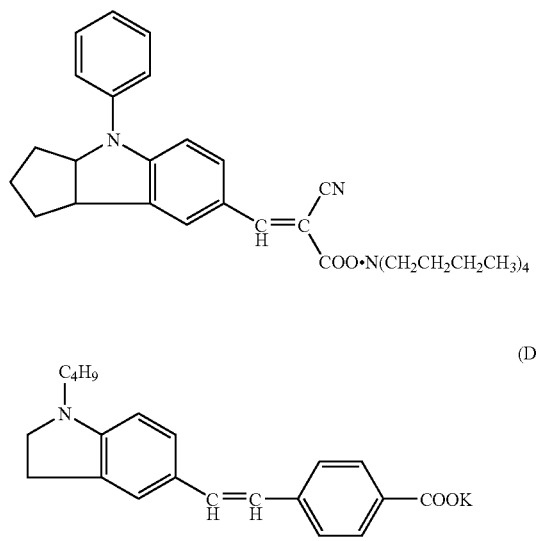
(D-4)
(D-5)
(D-6)
(D-7)
-continued
(D-8)
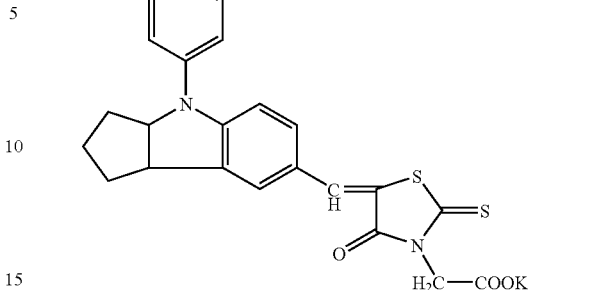
(D-9)
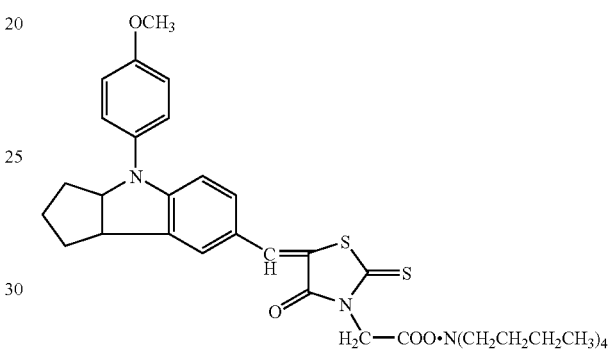
(D-10)
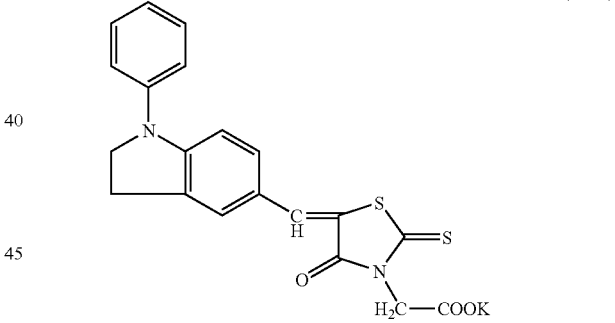
(D-11)
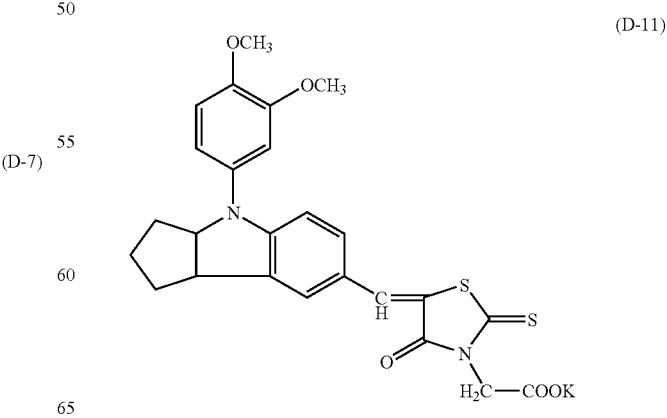

-continued
(D-12)
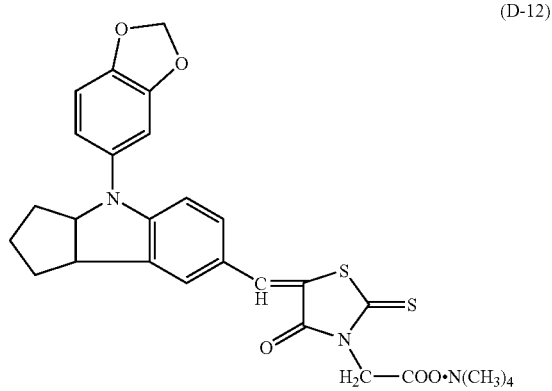
(D-13)
(D-14)
(D-15)
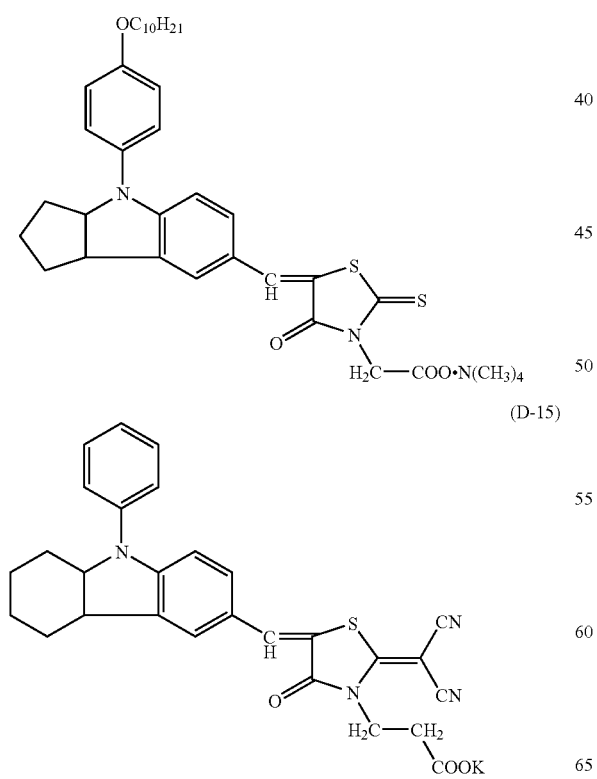
-continued
(D-16)
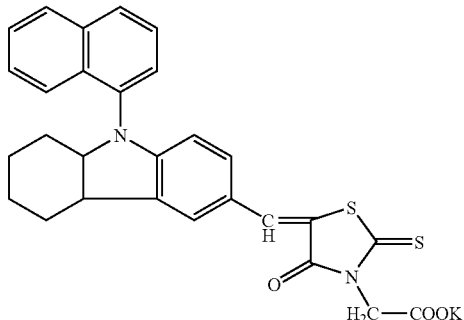
(D-17)
(D-18)
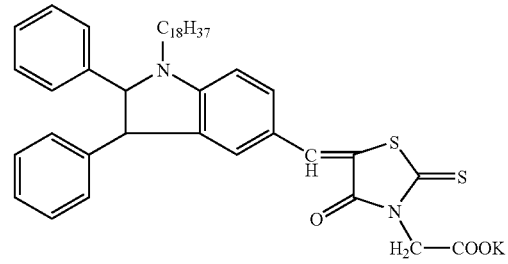
(D-19)
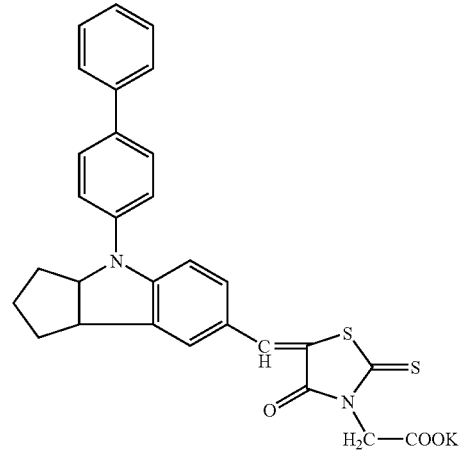

-continued
(D-20)
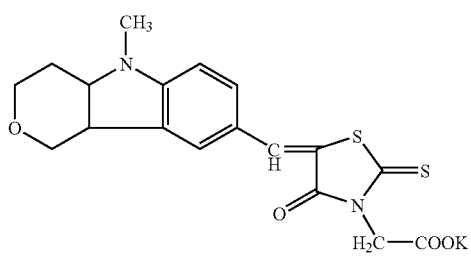
(D-21)
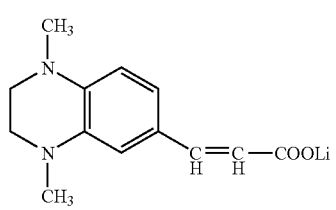
(D-22)
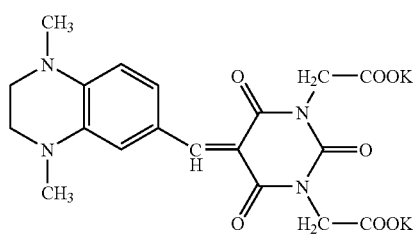
(D-23)
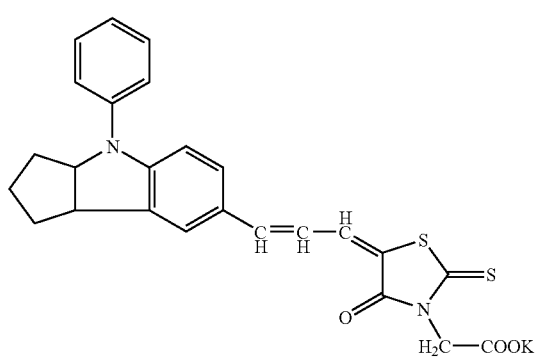
(D-24)
-continued
(D-25)
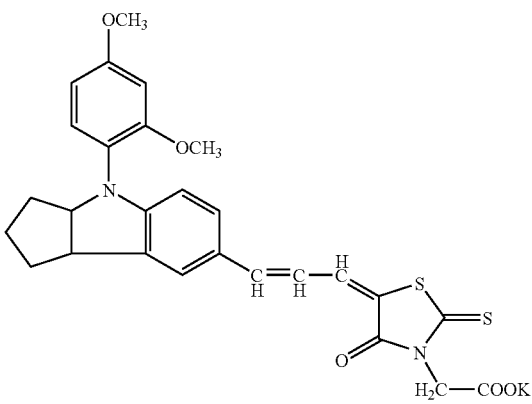
(D-26)
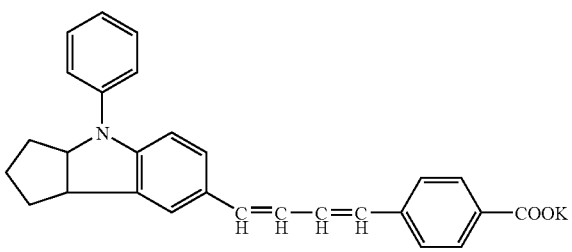
(D-27)
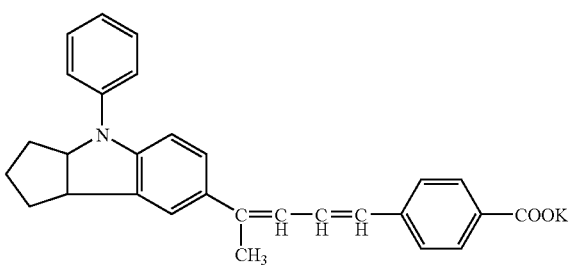
(D-28)
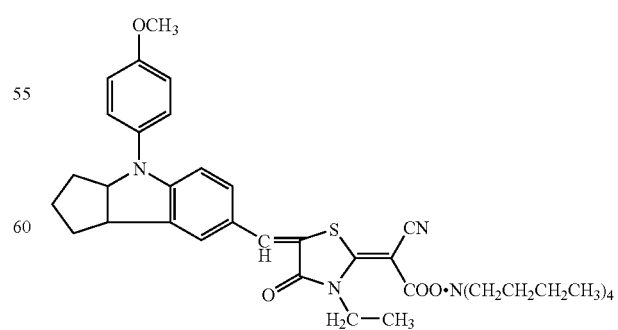

-continued

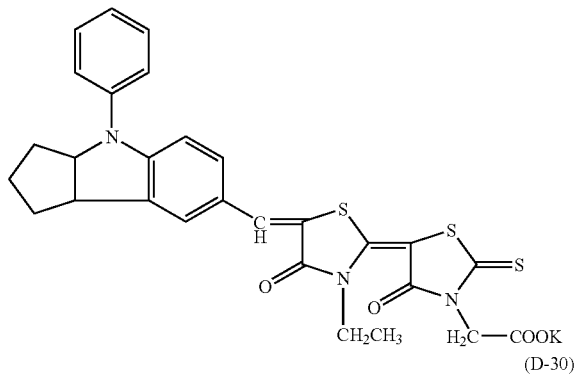

(D-29)

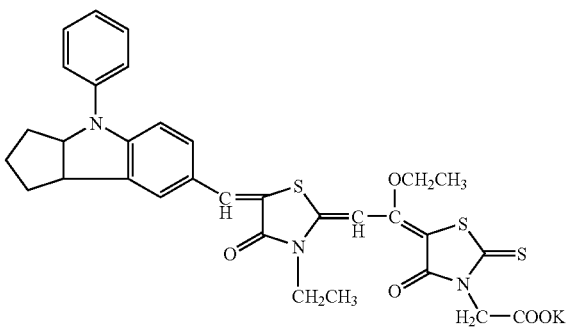

(D-30)

The photoelectric conversion material of the present invention contains one of the organic dye of the general formula (I), the merocyanine dye of the general formula (II), the merocyanine dye of the general formula (IV) and the merocyanine dye of the general formula (V).

The semiconductor electrode of the present invention is formed of a substrate having an electrically conductive surface, a semiconductor layer coated on the electrically conductive surface and a dye adsorbed on the surface of the semiconductor layer, wherein said dye contains a dye selected from the organic dye of the general formula (I), the merocyanine dye of the general formula (II), the merocyanine dye of the general formula (IV) or the merocyanine dye of the general formula (V).

The above substrate having an electrically conductive surface (to be sometimes referred to as "electrically conductive substrate" hereinafter) can be selected from a substrate having electrical conductivity itself such as a metal or a glass or plastic having an electrically conductive surface layer containing an electrically conductive agent. In the latter case, the electrically conductive agent includes metals such as platinum, gold, silver, copper and aluminum, carbon, an indium-tin composite oxide (to be abbreviated as "ITO" hereinafter) and metal oxides such as tin oxide doped with fluorine (to be abbreviated as "FTO" hereinafter). The electrically conductive substrate preferably has transparency so that it transmits at least 10% light, more preferably has transparency so that it transmits at least 50% of light. Above all, an electrically conductive glass formed by depositing an electrically conductive layer made of ITO or FTO on a glass is particularly preferred.

For decreasing the resistance of the transparent electrically conductive substrate, a metal lead wire may be used. The material for the metal lead wire includes metals such as aluminum, copper, silver, gold, platinum and nickel. The metal lead wire is disposed on the transparent substrate by vapor deposition, sputtering or press-bonding, and ITO or FTO is formed thereon. Alternatively, the metal lead wire is provided on the transparent electrically conductive layer.

The semiconductor for constituting the semiconductor layer can be selected from a simple semiconductor such as silicon or germanium, a compound semiconductor typified by chalcogenide of a metal, or a compound having a perovskite structure. The chalcogenide of a metal includes an oxide of titanium, tin, zinc, iron, tungsten, zirconium, hafnium, strontium, indium, cerium, yttrium, lanthanum, vanadium, niobium or tantalum, a sulfide of cadmium, zinc, lead, silver, antimony or bismuth, a selenide of cadmium or lead or a telluride of cadmium. As other compound semiconductors, a phosphonide of zinc, gallium, indium or cadmium, gallium-arsenide, a copper-indium-selenide, a copper-indium-sulfide and the like are preferred. The compound having a perovskite structure preferably includes strontium titanate, calcium titanate, sodium titanate, barium titanate and potassium niobate.

The semiconductor for use in the present invention may be a single crystal or a polycrystal. While a single crystal is preferred in view of conversion efficiency, a polycrystal is preferred in view of a production cost and availability of raw materials. The particle diameter of the semiconductor is preferably 4 nm or more but 1 μm or less.

The method for forming the semiconductor layer on the electrically conductive substrate includes a method in which a dispersion or colloid solution of semiconductor fine particles is applied onto the electrically conductive substrate and a sol-gel method. The method for preparing the above dispersion includes the above sol-gel method, a method in which a material is mechanically pulverized with a mortar or the like, a method in which a material is dispersed while it is milled with a milling machine, and a method in which a semiconductor is precipitated in a solvent in the form of fine particles during the synthesis of the semiconductor and used as it is.

When a dispersion of the semiconductor is prepared by mechanical pulverization or milling with a milling machine, the dispersion is prepared in the form of a dispersion of semiconductor fine particles alone or a mixture of semiconductor fine particles with a resin in water or an organic solvent. The above resin includes a polymer or copolymer of a vinyl compound such as styrene, vinyl acetate, acrylic acid ester or methacrylic acid ester, a silicone resin, a phenoxy resin, a polysulfone resin, a polyvinylbutyral resin, a polyvinylformal resin, a polyester resin, a cellulose ester resin, a cellulose ether resin, a urethane resin, a phenolic resin, an epoxy resin, a polycarbonate resin, a polyallylate resin, a polyamide resin and a polyimide resin.

The solvent for dispersing the semiconductor fine particles includes water, alcohol solvents such as methanol, ethanol and isopropyl alcohol, ketone solvents such as acetone, methyl ethyl ketone and methyl isobutyl ketone, ester solvents such as ethyl formate, ethyl acetate and n-butyl acetate, ether solvents such as diethyl ether, dimethoxyethane, tetrahydrofuran, dioxolane and dioxane, amide solvents such as N,N-dimethylformamide, N,N-dimethylacetamide and N-methyl-2-pyrrolidone, halogenated hydrocarbon solvents such as dichloromethane, chloroform, bromoform, methyl iodide, dichloroethane, trichloroethane, trichloroethylene, chlorobenzene, o-dichlorobenzene, fluorobenzene, bromobenzene, iodobenzene and 1-chloronaphthalene and hydrocarbon solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene and cumene. These may be used solely or in the form of a mixture containing two or more of them.

The method of application of the obtained dispersion includes a roll method, a dipping method, an air knife method, a blade method, a wire bar method, a slide hopper method, an extrusion method, a curtain method, a spin method or a spray method.

The semiconductor layer may be a single layer or a multi-layer. In a multi-layered semiconductor layer, dispersions containing semiconductor fine particles having different particle diameters between (among) layers may be applied to form a multi-layered coating, or a multi-layered coating containing semiconductors different between (among) layers and containing resins and additives having different compositions between (among) the layers may be formed. When the thickness of a layer formed by carrying out the application once is insufficient, the application to form a multi-layered coating is an effective means.

Generally, with an increase in the thickness of the semiconductor layer, the amount of the dye held per unit area of a projection image increases, so that the capture ratio of light increases. Since, however, the diffusion distance of generated electrons increases, the degree of recoupling of charges increases. Therefore, the thickness of the semiconductor layer is preferably 0.1 to 100 µm, more preferably 1 to 30 µm.

After the semiconductor fine particles are applied onto the electrically conductive substrate, they may be heat-treated, or may not be heat-treated. For improving electronic contacts of the particles and the coating strength and improving the adhesion of the layer to the substrate, it is preferred to carry out the heat treatment. The temperature for the heat treatment is preferably 40 to 700° C., more preferably 80 to 600° C. The time period for the heat treatment is preferably 5 minutes to 20 hours, more preferably 10 minutes to 10 hours.

The semiconductor fine particles preferably have a large surface area so that they can adsorb a large amount of the dye. In a state where the semiconductor layer is formed on the substrate, the surface area of the semiconductor fine particles is preferably at least 10 times, more preferably at least 100 times, the area of an projection image.

The method for allowing the semiconductor layer to adsorb the dye can be selected from a method in which a work electrode containing the semiconductor fine particles is immersed in a dye solution or dye dispersion or a method in which a dye solution or dye dispersion is applied to the semiconductor layer to allow the semiconductor layer to adsorb the dye. In the former method, there can be employed an immersion method, a dipping method, a roll method, an air knife method or the like. In the latter method, there can be employed a wire bar method, a slide hopper method, an extrusion method, a curtain method, a spin method, a spray method or the like.

For adsorption of the dye, a condensation agent may be used in combination. The condensation agent may be any one of an agent that has a catalytic function presumably for binding the dye to an inorganic material surface physically or chemically and an agent that stoichiometrically works to shift a chemical equilibrium advantageously. As a condensation aid, further, thiol or a hydroxy compound may be added.

The solvent for dissolving or dispersing the dye includes water, alcohol solvents such as methanol, ethanol and isopropyl alcohol, ketone solvents such as acetone, methyl ethyl ketone and methyl isobutyl ketone, ester solvents such as ethyl formate, ethyl acetate and n-butyl acetate, ether solvents such as diethyl ether, dimethoxyethane, tetrahydrofuran, dioxolane and dioxane, amide solvents such as N,N-dimethylformamide, N,N-dimethylacetamide and N-methyl-2-pyrrolidone, halogenated hydrocarbon solvents such as dichloromethane, chloroform, bromoform, methyl iodide, dichloroethane, trichloroethane, trichloroethylene, chlorobenzene, o-dichlorobenzene, fluorobenzene, bromobenzene, iodobenzene and 1-chloronaphthalene and hydrocarbon solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene and cumene. These may be used solely or in the form of a mixture containing two or more of them.

The temperature for adsorption of the dye is preferably −50° C. or higher but 200° C. or lower. The adsorption may be carried out with stirring. In the stirring method, a stirrer, a ball mill, a paint conditioner, a sand mill, attriter, a disperser, supersonic dispersion or the like is employed, while the stirring method shall not be limited thereto. The time period for the adsorption is preferably at least 5 seconds but 1,000 hours or less, more preferably at least 10 second but 500 hours or less, still more preferably 1 minute to 150 hours.

In the above manner, the semiconductor electrode of the present invention can be obtained.

In the semiconductor electrode of the present invention, when the merocyanine dye of the above general formula (II) is used as a dye, it is preferred to use a steroid compound in combination with the merocyanine dye.

As the above steroid compound, there can be used a compound represented by the general formula (III).

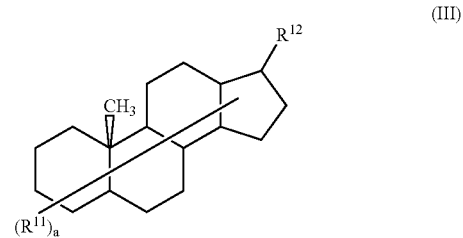

(III)

In the general formula (III), $R^{11}$ is a hydrogen atom, a hydroxyl group, a halogen atom, an alkyl group, an alkoxy group, an aryl group, a heterocyclic moiety, an acyl group, an acyloxy group, an oxycarbonyl group, an oxo group or an acidic group and may have a substituent; $R^{12}$ is an alkyl group containing an acidic group; a is an integer of 0 to 13; and a steroid ring may internally contain a double bond.

In the general formula (III), specific examples of $R^{11}$ include a hydrogen atom, a hydroxyl group, the above halogen atoms, the above alkyl groups, the above alkoxy groups, the above alkyl groups, the above heterocyclic moieties, acyl groups such as acetyl and 4-methylbenzoyl, acyloxy groups such as acetyloxy and 4-methylbenzoyloxy, oxycarbonyl groups such as ethoxycarbonyl and phenyloxycarbonyl, an oxo group and the above acidic groups. $R^{11}$ may have a substituent, and specific examples of the substituent include the above alkyl groups, the above alkoxy groups, the above alkylthio groups, the above aryloxy groups, the above arylthio groups, the above halogen atoms, the above di-substituted amino groups, the above aryl groups, the above heterocyclic moieties, the above acidic groups and the above electron-attracting groups. Specific examples of $R^{12}$ include the above alkyl groups, and may have a substituent. Specific examples of the substituent include the above alkyl groups, the above aryl groups, the above alkoxy groups, the above acyl groups and the above acidic groups.

Specific examples of the steroid compound are as shown in (E-1) to (E-10), while the steroid compound shall not be limited thereto.

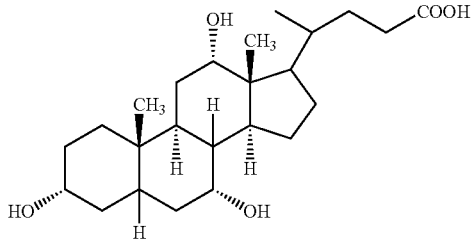
(E-1)

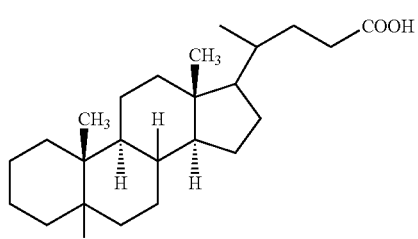
(E-2)

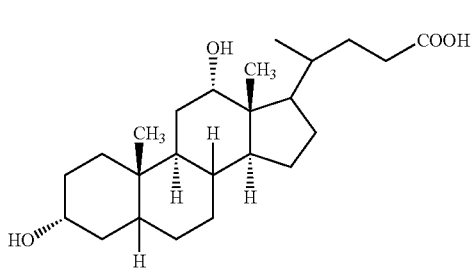
(E-3)

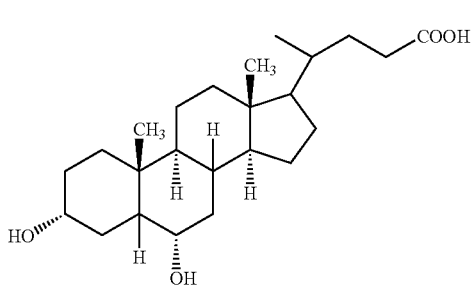
(E-4)

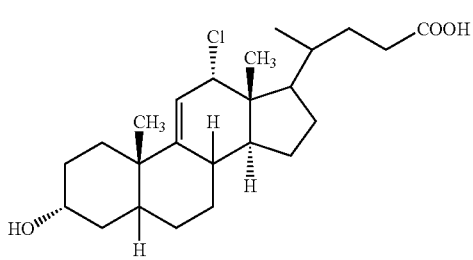
(E-5)

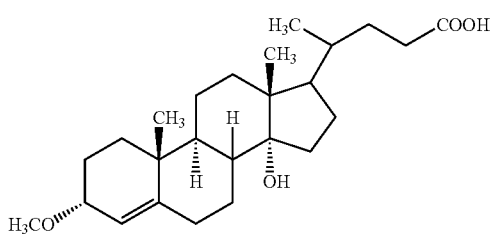
(E-6)

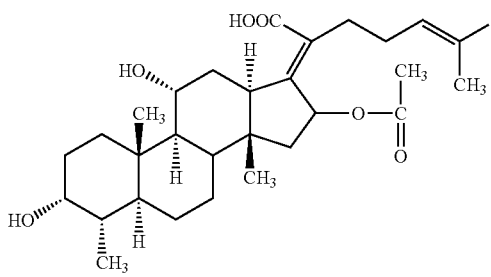
(E-7)

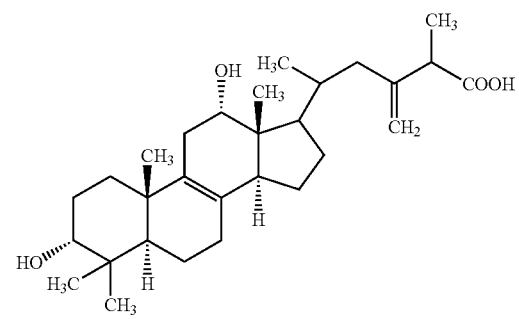
(E-8)

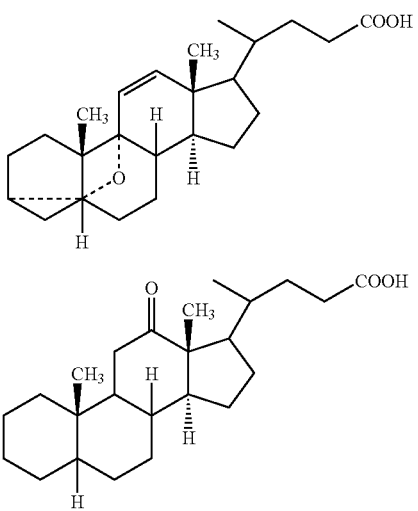
(E-9)

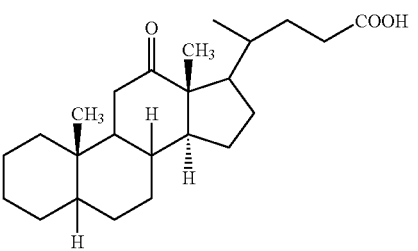
(E-10)

The above steroid compound is used in combination with the merocyanine dye of the above general formula (II) when the merocyanine dye is adsorbed. The amount of the steroid compound per part by mass of the dye is preferably 0.001 to 1,000 parts by mass, more preferably 0.1 to 100 parts by mass.

The photoelectric conversion device of the present invention is a device to which the organic dye of the general formula (I), the merocyanine dye of the general formula (II), the merocyanine dye of the general formula (IV) or the merocyanine dye of the general formula (V) is applied, and specifically, it is a device having a semiconductor electrode containing the above dye as a dye. More specifically, the photoelectric conversion device is constituted of a semiconductor electrode formed of an electrically conductive substrate and a semiconductor layer (photosensitive layer) formed on the electrically conductive substrate and sensitized with the dye, a charge-transporting layer and a counter electrode. The photosensitive layer may have a single-layered constitution or a layers-stacked constitution, and it is designed depending upon an object. Further, in each of boundaries of the device such as a boundary between the electrically conductive layer of the electrically conductive substrate and the photosensitive layer, a boundary between the photosensitive layer and the charge-transporting layer and any other boundary, a component constituting one layer and a component constituting the other may be mutually diffused into, or mixed with, one another.

In the photoelectric conversion device of the present invention, the charge-transporting layer can be selected from an electrolytic solution of a redox pair in an organic solvent, a gel electrolyte prepared by impregnating a polymer matrix with a solution of a redox pair in an organic solvent, a molten salt containing a redox pair, a solid electrolyte, an organic hole-transporting material, or the like.

The electrolytic solution for use in the present invention is preferably constituted of an electrolyte, a solvent and an additive. The electrolyte preferably includes a combination of a metal iodide such as lithium iodide, sodium iodide, potassium iodide, cesium iodide or calcium iodide with iodine, a combination of a quaternary ammonium iodide such as tetraalkylammonium iodide, pyridium iodide or imidazolium iodide with iodine, a combination of a metal bromide such as lithium bromide, sodium bromide, potassium bromide, cesium bromide or calcium bromide with bromine, a combination of a quaternary ammonium bromide such as tetraalkylammonium bromide or pyridinium bromide with bromine, metal complexes such as ferrocyanic acid salt-ferricyanic acid salt or ferrocene-ferricynium ion, sulfur compounds such as sodium polysulfide and alkylthiol-alkyldisulfide, a viologen dye and hydroquinone-quinone. The above electrolytes may be used solely or in the form of a mixture. As an electrolyte, there may be used a molten salt that is in a molten state at room temperature. When such a molten salt is used, particularly, it is not necessary to use a solvent.

The electrolyte concentration in the electrolytic solution is preferably 0.05 to 20 M, more preferably 0.1 to 15M. The solvent for the electrolytic solution preferably includes carbonate solvents such as ethylene carbonate and propylene carbonate, heterocyclic compounds such as 3-methyl-2-oxazolidinone, ether solvents such as dioxane, diethyl ether and ethylene glycol dialkyl ether, alcohol solvents such as methanol, ethanol and polypropylene glycol monoalkyl ether, nitrile solvents such as acetonitrile and benzonitrile, and aprotic solvents such as dimethylsulfoxide and sulfolane. Further, a basic compound such as tert-butylpyridine, 2-picoline or 2,6-lutidine may be used in combination.

In the present invention, the electrolyte can be gelled by adding a polymer, adding an oil gelatinizing agent, polymerizing it with a polyfunctional monomer or a carrying out a crosslinking reaction of a polymer. The polymer preferred for the gelatinization can be selected from polyacrylonitrile, polyvinylidene fluoride or the like. The gelatinizing agent preferred for the gelatinization by adding an oil gelatinizing agent can be selected from dibenzylidene-D-sorbitol, a cholesterol derivative, an amino acid derivative, an alkylamide derivative of trans-(1R,2R)-1,2-cyclohexanediamine, an alkylurea derivative, N-octyl-D-gluconamidebenzoate, a twin head type amino acid derivative or a quaternary ammonium derivative.

The monomer preferred for the polymerization with a polyfunctional monomer can be selected from divinylbenzene, ethylene glycol dimethacrylate, ethylene glycol diacrylate, diethylene glycol dimethacrylate, triethylene glycol dimethacrylate, pentaerythritol triacrylate or trimethylolpropane triacrylate. Further, the monomer may contain a monofunctional monomer selected from esters or amides derived from acrylic acid or α-alkylacrylic acid, such as acrylamide or methyl acrylate, esters derived from maleic acid or fumaric acid, such as dimethyl maleate or diethyl fumarate, dienes such as butadiene and cyclopentadiene, aromatic vinyl compounds such as styrene, p-chlorostyrene and sodium styrenesulfonate, vinyl esters, acrylonitrile, methacrylonitrile, a vinyl compound having a nitrogen-containing heterocyclic ring, a vinyl compound having a quaternary ammonium salt, N-vinylsulfoneamide, vinylsulfonic acid, vinylidene fluoride, vinyl alkyl ethers or N-phenylmaleimide. The amount of the polyfunctional monomer based on the entire monomer amount is preferably 0.5 to 70 mass %, more preferably 1.0 to 50 mass %.

The above monomer can be polymerized by radical polymerization. The monomer for a gel electrolyte, which can be used in the present invention, can be radical-polymerized by heating, by applying light or electron beams, or electrochemically. The polymerization initiator for use in the formation of a crosslinked polymer by heating is preferably selected from azo initiators such as 2,2'-azobisisobutyronitrile, 2,2'-azobis (2,4-dimethylvaleronitrile) and dimethyl-2,2'-azobis(2-methylpropionate) or peroxide initiators such as benzoyl peroxide. The amount of the above polymerization initiator based on the entire monomer amount is preferably 0.01 to 20 mass %, more preferably 0.1 to 10 mass %.

When the electrolyte is gelatinized by a crosslinking reaction of a polymer, desirably, a polymer having a reactive group necessary for a crosslinking reaction and a crosslinking agent are used in combination. Examples of the reactive group for the crosslinking reaction preferably include nitrogen-containing heterocyclic rings such as pyridine, imidazole, thiazole, oxazole, triazole, morpholine, piperidine and piperazine. Examples of the crosslinking agent preferably include difunctional or higher reagents that can react with a nitrogen atom in an electrophilic reaction, such as a halogenated alkyl, a halogenated aralkyl, sulfonic acid ester, an acid anhydride, acid chloride and isocyanate.

When an inorganic solid compound is used in place of the electrolyte, copper iodide, copper thiocyanide or the like can be incorporated into an electrode by a casting method, an application method, a spin coating method, an immersion method, an electric plating method or some other means.

In the present invention, further, an organic charge-transporting material can be used in place of the electrolyte. The charge-transporting material includes a hole-transporting material and an electron-transporting material. Examples of the former include oxadiazoles disclosed in JP-B-34-5466, triphenylmethanes disclosed in JP-B-45-555, pyrazolines disclosed in JP-B-52-4188, hydrazones disclosed in JP-B-55-42380, oxadiazoles disclosed in JP-A-56-123544, tetraarylbenzidines disclosed in JP-A-54-58445 and stilbenes disclosed in JP-A-58-66440 or JP-A-60-98437. Of these, hydrazones disclosed in JP-A-60-24553, JP-A-2-96767, JP-A-2-183260 and JP-A-2-226160 and stilbenes disclosed in JP-A-2-51162 and JP-A-3-75660 are particularly preferred as a charge-transporting material for use in the present invention. These materials may be used solely or in the form of a mixture containing at least two compounds of these.

Examples of the electron-transporting material include chloranil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 1,3,7-tetranitrodibenzothiophene and 1,3,7-trinitrodibenzothiophene-5,5-dioxide. These electron-transporting materials may be used solely or in the form of a mixture containing at least two compounds of these.

As a sensitizer for increasing a sensitization effect, further, an electron-attracting compound of some type can be added. Examples of the above electron-attracting compound include quinones such as 2,3-dichloro-1,4-naphthoquinone, 1-nitroanthraquinone, 1-chloro-5-nitroanthraquinone, 2-chloroanthraquinone and phenanthlenequinone, aldehydes such as 4-nitrobenzaldehyde, ketones such as 9-benzoylanthracene, indandione, 3,5-dinitrobenzophenone and 3,3',5,5'-tetranitrobenzophenone, acid anhydrides such as phthalic acid anhydride and 4-chloronapthalic acid anhydride, cyano compounds such as terephthalmalononitrile, 9-anthrylmethylidenemalononitrile, 4-nitrobenzalmalononitrile and 4-(p-nitrobenzoyloxy)benzalmalononitrile, and phthalides such as 3-benzalphthalide, 3-($\alpha$-cyano-p-nitrobenzal)phthalide and 3-($\alpha$-cyano-p-nitrobenzal)-4,5,6,7-tetrachlorophthalide.

When these charge-transporting materials are used to form the charge-transporting layer, it is preferred to use a resin in combination. The resin can be selected from a polystyrene resin, a polyvinyl acetal resin, a polysulfone resin, a polycarbonate resin, a polyester resin, a polyphenylene oxide resin, a polyallylate resin, an acrylic resin, a methacrylic resin or a phenoxy resin. Of these, a polystyrene resin, a polyvinyl acetal resin, a polycarbonate resin, a polyester resin or a polyallylate resin is preferred. Further, these resins may be used solely or in the form of a copolymer formed from at least two compounds of these.

Some resins of these are poor in mechanical strength such as tensile, flexing and compression strengths. For improving the resin in these properties, there can be added a substance that imparts plasticity. Specifically, the above substance includes phthalic acid ester (e.g., DOP, DBP, phosphoric acid ester (e.g., TCP, TOP), sebacic acid ester, adipic acid ester, nitrile rubber and chlorinated hydrocarbons. These substances cause adversary effect on the properties when added in an amount more than necessary, so that the amount thereof based on the binder resin is preferably 20% or less. In addition, an anti-oxidant, a curling preventer, etc., may be added as required.

The amount of the resin per part by mass of the charge-transporting material is preferably 0.001 to 20 parts by mass, more preferably 0.01 to 5 parts by mass. When the content of the resin is too high, the sensitivity decreases. When the content of the resin is too low, repetition properties may be caused to be poor or a coating may be caused to be defective.

The method of forming the charge-transporting layer includes two methods when classified largely. One method is a method in which a counter electrode is first attached to a layer containing semiconductor fine particles carrying a sensitizer dye, and the charge-transporting layer in the form of a liquid is inserted into a gap between them. The other method is a method in which the charge-transporting layer is provided directly on the layer containing semiconductor fine particles. In the latter method, the counter electrode is provided thereafter.

In the former method, the method of inserting the charge-transporting layer includes an atmospheric pressure process utilizing a capillary action based on immersion, or the like and a vacuum process utilizing a pressure lower than atmospheric pressure to replace a gas phase with a liquid phase. In the latter case, it is required to provide a counter electrode to a wet charge-transporting layer while it is not dried, so that the liquid leak of an edge portion can be prevented. For a gel electrolytic solution, there can be employed a method in which the electrolytic solution is applied by a wet method and solidified by a polymerization method or the like. In this case, the counter electrode can be provided after the electrolytic solution is dried and fixed. The method of providing an organic charge-transporting material solution or a gel electrolyte in addition to the electrolytic solution includes an immersion method, a roller method, a dipping method, an air knife method, an extrusion method, a slide hopper method, a wire bar method, a spinning method, a spray method, a casting method and various printing methods like the method of providing the layer containing semiconductor fine particles or dyes.

As the counter electrode, generally, a substrate having an electrically conductive layer can be used like the above electrically conductive substrate. In a constitution that can fully maintain strength and sealing performance, the substrate is not necessarily required. Specific examples of the material for the counter electrode include metals such as platinum, gold, silver, copper, aluminum, rhodium and indium, carbon and electrically conductive metal oxides such as ITO and FTO. The thickness of the counter electrode is not specially limited.

Light is required to arrive at the photosensitive layer. For this purpose, at least one of the above electrically conductive substrate and the counter electrode is required to be substantially transparent. The photoelectric conversion device of the present invention preferably has a constitution in which the electrically conductive substrate is transparent and sunlight enters from the substrate side. In this case, preferably, the counter electrode is formed of a material that reflects light, and the material is preferably a glass or plastic on which a metal or an electrically conductive oxide is vapor-deposited or a metal thin film.

As described already, the method of providing the counter electrode includes two methods, in which the counter electrode is provided on the charge-transporting layer or provided on the layer containing semiconductor fine particles. In each case, a material for the counter electrode is applied to, laminated on, vapor-deposited on, or attached to, the charge-transporting layer or the layer containing semiconductor fine particles, depending upon types of materials of the counter electrode and types of the charge-transporting layer, whereby the counter electrode can be formed. Further, when the charge-transporting layer is a solid, the above electrically conductive material can be directly applied thereto, vapor-deposited thereon, or deposited thereon by CVD, whereby the counter electrode can be formed.

The present invention will be explained more in detail with reference to Examples hereinafter, while the present invention shall not be limited to these Examples.

Synthesis Example V-1 Synthesis of Compound (F-2)

N,N-Dimethylformamide (21.4 g) was placed in a flask and stirred with cooling on an ice bath, and phosphorus oxychloride (13.3 g) was dropwise added over 15 minutes. The mixture was stirred at the same temperature for 1 hour, and a solution of julolidine (5.1 g) represented by the following (F-1) in N,N-dimethylformamide (10 ml) was dropwise added over 10 minutes. After 1 hour, a reaction mixture was poured into a diluted sodium hydroxide aqueous solution (200 ml), and an organic component was extracted with toluene. The solvent was distilled off, and a residue was purified by silica gel column chromatography, to give the following compound (F-2). 5.3 g. Yield 91%.

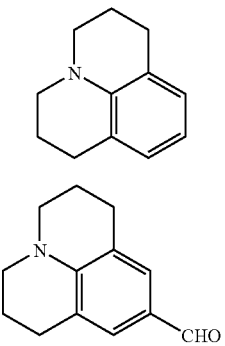

(F-1)

(F-2)

Example V-1 Synthesis of Compound (A-5) Shown as an Example

Compound (F-2) (1.0 g), rhodanine-3-acetic acid (0.96 g) and ammonium acetate (0.4 g) were dissolved in 2.0 g of acetic acid, and the mixture was stirred under heat at 120° C. After 30 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker and washed with water (200 ml). The crude crystal was re-crystallized from methyl cellosolve, to give Compound (A-5) shown as an example. 1.3 g. Yield 70%.

Example V-2 Synthesis of Compound (A-8) Shown as an Example

The following Compound (F-3) (10.1 g), rhodanine-3-acetic acid (7.4 g) and ammonium acetate (2.56 g) were dissolved in 15.9 g of acetic acid, and the mixture was stirred under heat at 120° C. After 30 minutes, when the heating was stopped, the reaction product immediately solidified. The reaction product was cooled to room temperature, and then, water (100 ml) was added. The mixture was stirred, and a crystal was recovered by filtration. The crystal was transferred into a beaker and washed with water (500 ml) twice and then washed with 2-propanol (100 ml) twice. The crude crystal was re-crystallized from methyl cellosolve (about 50 ml), to give Compound (A-8) shown as an example. 11.0 g. Yield 66%.

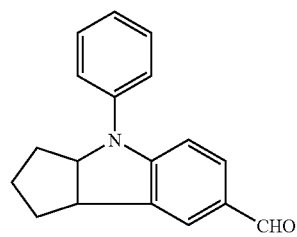

(F-3)

Example V-3 Synthesis of Compound (A-9) Shown as an Example

The following Compound (F-4) (2.6 g), rhodanine-3-acetic acid (1.7 g) and ammonium acetate (0.5 g) were dissolved in 2.2 g of acetic acid, and the mixture was stirred under heat at 120° C. After 30 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker and washed with water (100 ml) twice and then washed with 2-propanol (50 ml) twice, to give Compound (A-9) shown as an example. 2.9 g. Yield 69%.

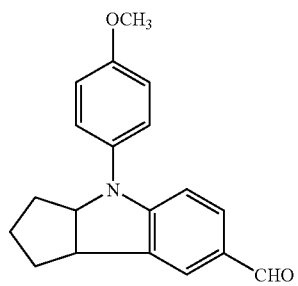

(F-4)

Example V-4 Synthesis of Compound (A-10) Shown as an Example

The following Compound (F-5) (1.6 g), rhodanine-3-acetic acid (1.4 g) and ammonium acetate (1.0 g) were dissolved in 4.4 g of acetic acid, and the mixture was stirred under heat at 120° C. After 30 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker and washed with water (100 ml) twice and then washed with 2-propanol (50 ml) twice, to give Compound (A-9) shown as an example. 2.8 g. Yield 95%.

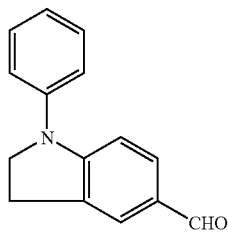

(F-5)

Example V-5 Preparation of Photoelectric Conversion Device

3 Grams of titanium oxide (P-25, supplied by Nippon Aerosil Co., Ltd.), 0.2 g of acetyl acetone and 0.3 g of a surfactant (Triton X-100, supplied by Aldrich Co., Ltd.) were dispersed with a paint conditioner together with 6.5 g of water for 6 hours. The thus-prepared dispersion was applied onto an FTO glass substrate with a wire bar to form a coating having a thickness of 10 µm. Then, the coating was dried at 100° C. for 1 hour and then heated in air at 450° C. for 30 minutes.

0.01 Gram of a dye shown by Compound (A-5) shown as an example was dissolved in 10 ml of ethanol. The above-prepared semiconductor electrode was immersed in the solution at room temperature for 15 hours to carry out adsorption treatment.

A solution of 0.03 M of iodine and 0.5 M of tetra-n-propylammonium iodide in a mixture solution of propylene carbonate/acetonitrile=6/4 was used as an electrolytic solution. An electrode prepared by sputtering platinum on FTO was used as a counter electrode.

The electrolytic solution was infiltrated into between the two electrodes to prepare a photoelectric conversion device. The above photoelectric conversion device was exposed to a xenon lamp having an intensity of 100 mW/cm² so that the device was irradiated, from the work electrode side, with light from which light having a wavelength of 400 nm or less was cut with a cut filter UV-39 supplied by Toshiba Corporation. As a result, the device showed excellent values; an open circuit voltage of 0.60 V, a short-circuit current density of 5.5 mA/cm², a fill factor of 0.65 and a conversion efficiency of 2.15%.

Examples V-6-V-12

Devices were prepared in the same manner as in Example V-5 except that Compound (A-5) shown as an example was replaced with dyes shown in Table 1, and the devices were evaluated in the same manner as in Example V-5. Table 1 shows the results.

TABLE 1

| | Compound | Open-circuit voltage (V) | Short-circuit current density (mA/cm²) | Fill factor | Conversion efficiency (%) |
|---|---|---|---|---|---|
| Ex. V-6 | A-2 | 0.58 | 5.5 | 0.59 | 1.88 |
| Ex. V-7 | A-3 | 0.60 | 6.4 | 0.64 | 2.46 |
| Ex. V-8 | A-8 | 0.62 | 7.0 | 0.66 | 2.86 |
| Ex. V-9 | A-9 | 0.64 | 8.0 | 0.64 | 3.23 |
| Ex. V-10 | A-10 | 0.63 | 5.9 | 0.68 | 2.53 |
| Ex. V-11 | A-13 | 0.63 | 7.3 | 0.64 | 2.94 |
| Ex. V-12 | A-14 | 0.65 | 7.1 | 0.65 | 3.00 |

Ex. = Example

As is clear from the results in Table 1, it is seen that the dyes of the present invention exhibit excellent conversion efficiency.

Comparative Example V-1

A device was prepared in the same manner as in Example V-5 except that Compound (A-5) shown as an example was replaced with a compound (G-1) shown below, and the device was evaluated in the same manner as in Example V-5. As a result, the device showed low values; an open-circuit voltage of 0.55 V, a short-circuit current density of 2.5 mA/cm², a fill factor of 0.51 and a conversion efficiency of 0.70%.

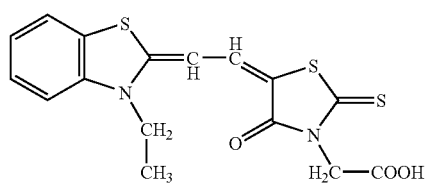

(G-1)

Comparative Example V-2

A device was prepared in the same manner as in Example V-5 except that Compound (A-5) shown as an example was replaced with a compound (G-2) shown below, and the device was evaluated in the same manner as in Example V-5. As a result, the device showed low values; an open-circuit voltage of 0.65 V, a short-circuit current density of 2.8 mA/cm², a fill factor of 0.45 and a conversion efficiency of 0.82%.

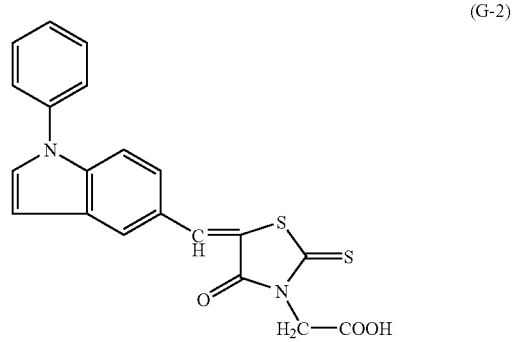

(G-2)

Example W-1 Synthesis of Compound (B-3) Shown as an Example

The following Compound (H-1) (1.18 g), cyanoacetic acid (0.46 g) and ammonium acetate (0.77 g) were dissolved in 2.5 g of acetic acid, and the mixture was stirred under heat at 120° C. After 30 minutes, the heating was stopped, and the mixture was cooled to room temperature. Water (100 ml) and ethyl acetate (100 ml) were added, and the mixture was transferred into a separating funnel. An organic layer was separated and dried over anhydrous sodium sulfate, and then the solvent was distilled off. A crude crystal was washed with ethyl acetate to give Compound (B-3) shown as an example. 0.54 g. Yield 34.8%. Melting point=208.1-210.1° C. FIG. 1 shows UV absorption spectrum of Compound (B-3) in ethanol. A maximum absorption wavelength (λmax)=399.6 nm. A maximum molecular coefficient (εmax)=23,100 l/mol·cm.

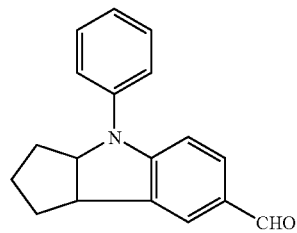

(H-1)

Example W-2 Synthesis of Compound (B-6) Shown as an Example

Figure 2:
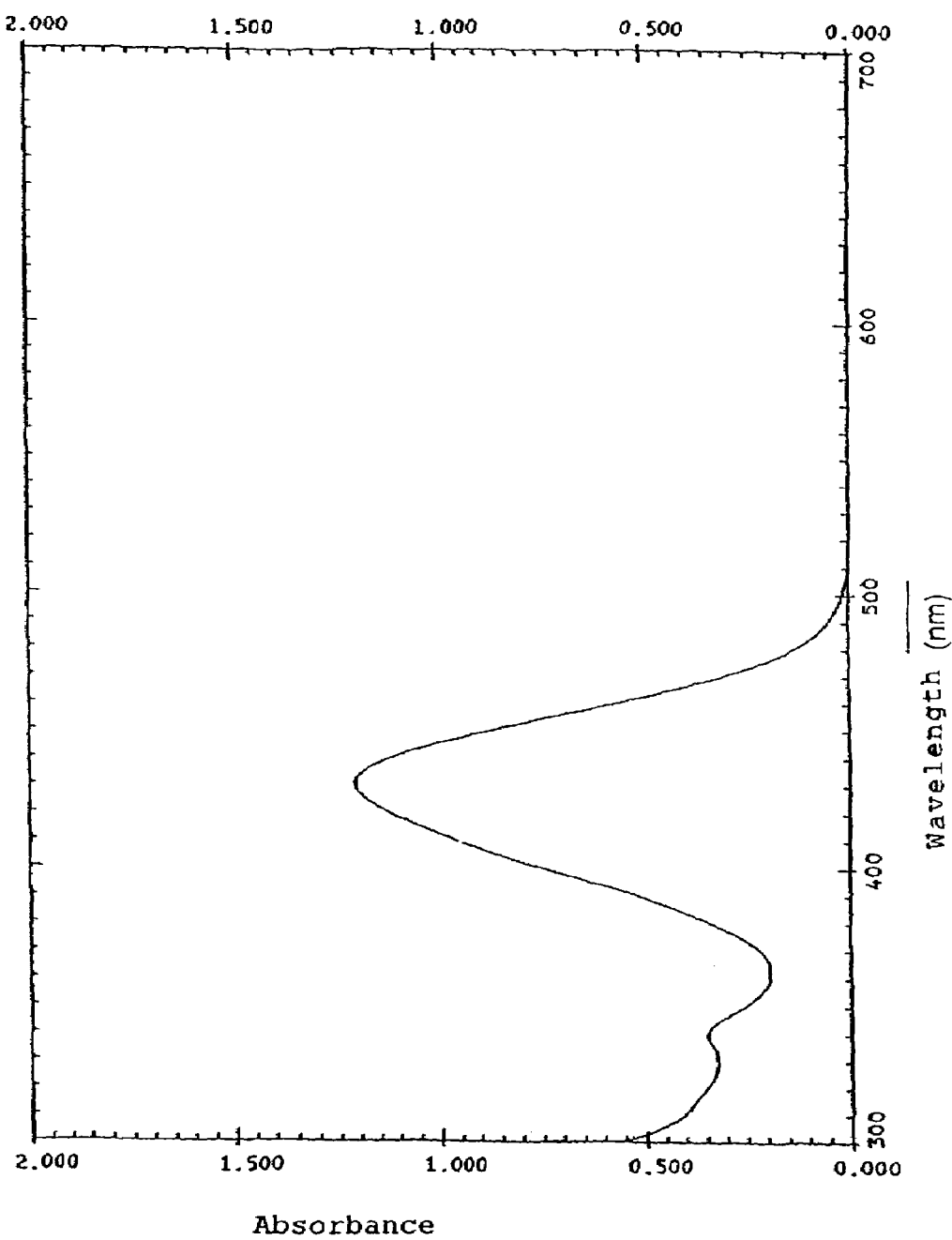

The following Compound (H-2) (1.82 g), rhodanine-3-acetic acid (1.59 g) and ammonium acetate (1.27 g) were dissolved in 3.9 g of acetic acid, and the mixture was stirred under heat at 120° C. After 30 minutes, when the heating was stopped, the reaction product immediately solidified. The reaction product was cooled to room temperature, and then, water (100 ml) was added. The mixture was stirred, and a crystal was recovered by filtration. The crystal was transferred into a beaker, and the crystal was washed with water (100 ml) twice and then washed with isopropyl alcohol with stirring to give Compound (B-6) shown as an example. 3.2 g. Yield 99%. Melting point=271.9-274.0° C. FIG. 2 shows UV absorption spectrum of Compound (B-6) in ethanol. A maximum absorption wavelength (λmax)=430.8 nm. A maximum molecular coefficient (εmax)=32,700 l/mol·cm.

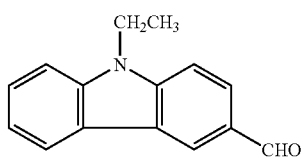

(H-2)

Example W-3 Synthesis of Compound (B-8) Shown as an Example

Figure 3:
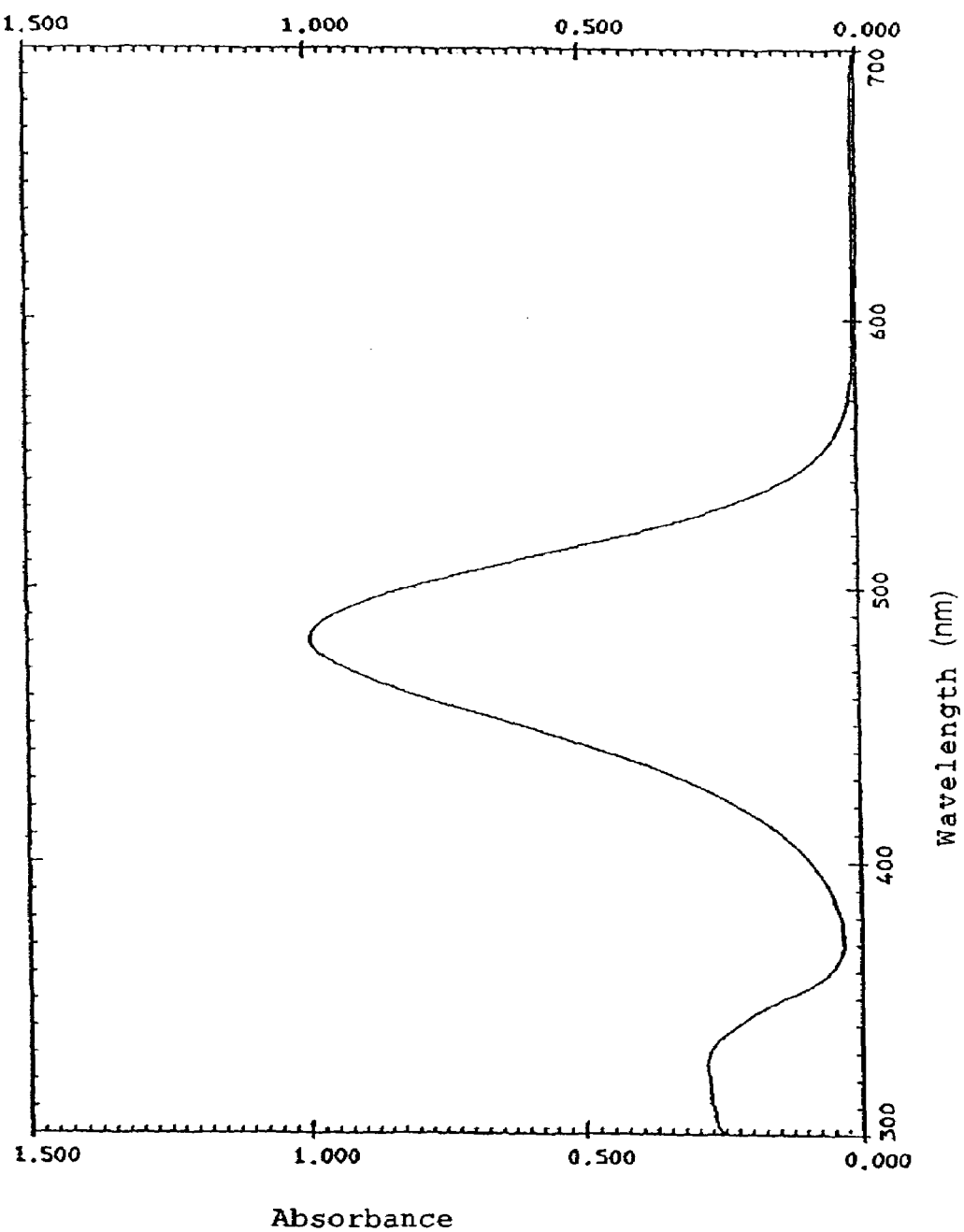

The Compound (H-1) (10.1 g), rhodanine-3-acetic acid (7.4 g) and ammonium acetate (2.56 g) were dissolved in 15.9 g of acetic acid, and the mixture was stirred under heat at 120° C. After 30 minutes, when the heating was stopped, the reaction product immediately solidified. The reaction product was cooled to room temperature, and then, water (100 ml) was added. The mixture was stirred, and a crystal was recovered by filtration. The crystal was transferred into a beaker, and the crystal was washed with water (500 ml) twice and then washed with 2-propanol twice. The crude crystal was re-crystallized from methyl cellosolve (about 50 ml), to give Compound (B-8) shown as an example. 11.0 g. Yield 66%. Melting point=249.2-253.7° C. (decomposed). FIG. 3 shows UV absorption spectrum of Compound (B-8) in ethanol. A maximum absorption wavelength (λmax)=481.0 nm. A maximum molecular coefficient (εmax)=31,000 l/mol·cm.

Example W-4 Synthesis of Compound (B-9) Shown as an Example

Figure 4:
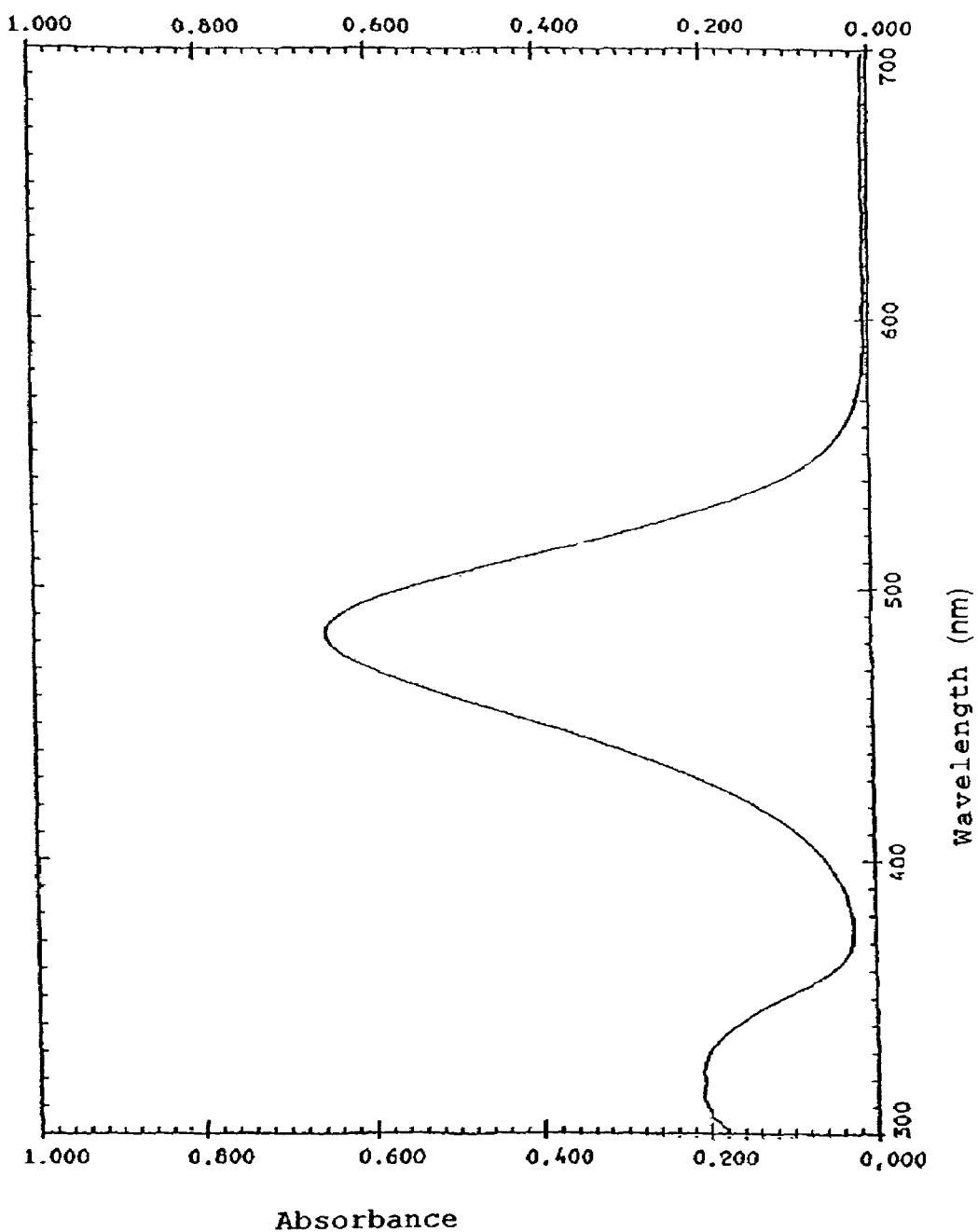

The following Compound (H-3) (2.6 g), rhodanine-3-acetic acid (1.7 g) and ammonium acetate (0.5 g) were dissolved in 2.2 g of acetic acid, and the mixture was stirred under heat at 120° C. After 30 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker, and the crystal was washed with water (100 ml) twice and then washed with 2-propanol (50 ml) twice to give Compound (B-9) shown as an example. 2.9 g. Yield 69%. Melting point=235.8-238.1° C. FIG. 4 shows UV absorption spectrum of Compound (B-9) in ethanol. A maximum absorption wavelength (λmax)=482.6 nm. A maximum molecular coefficient (εmax)=43,300 l/mol·cm.

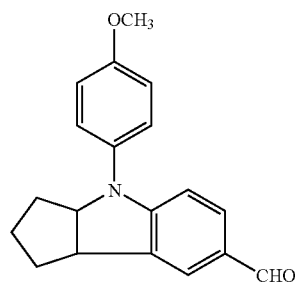

(H-3)

Example W-5 Synthesis of Compound (B-10) Shown as an Example

Figure 5:
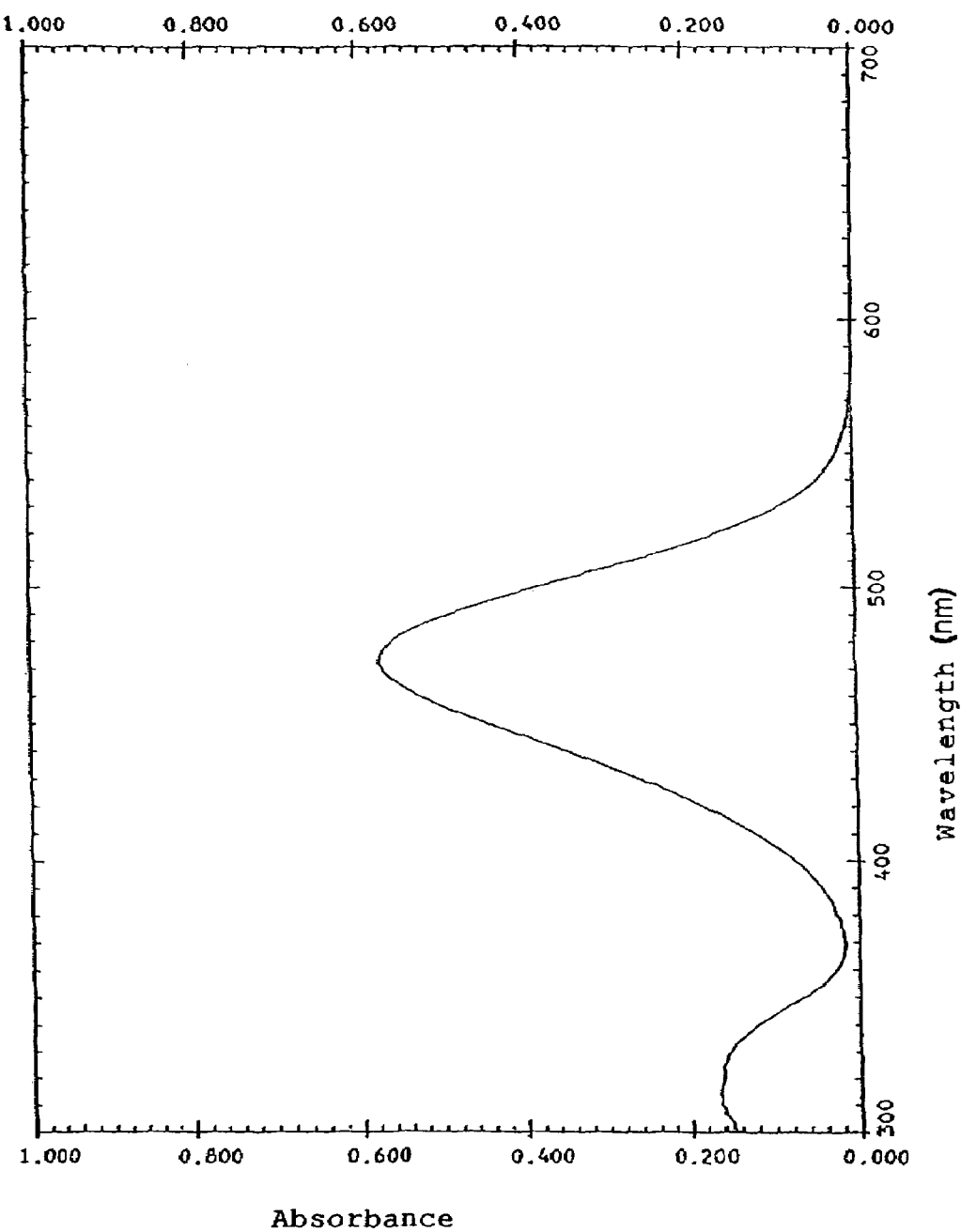

The following Compound (H-4) (1.64 g), rhodanine-3-acetic acid (1.40 g) and ammonium acetate (0.96 g) were dissolved in 4.4 g of acetic acid, and the mixture was stirred under heat at 120° C. After 15 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker, and the crystal was washed with water (100 ml) twice and then washed with 2-propanol (50 ml) twice to give Compound (B-10) shown as an example. 2.78 g. Yield 94.6%. Melting point=251.9-255.9° C. FIG. 5 shows UV absorption spectrum of Compound (B-10) in ethanol. A maximum absorption wavelength (λmax)=472.8 nm. A maximum molecular coefficient (εmax)=25,600 l/mol·cm.

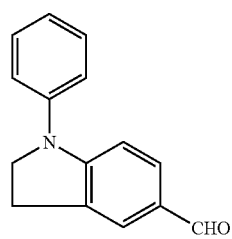

(H-4)

Example W-6 Synthesis of Compound (B-14) Shown as an Example

Figure 6:
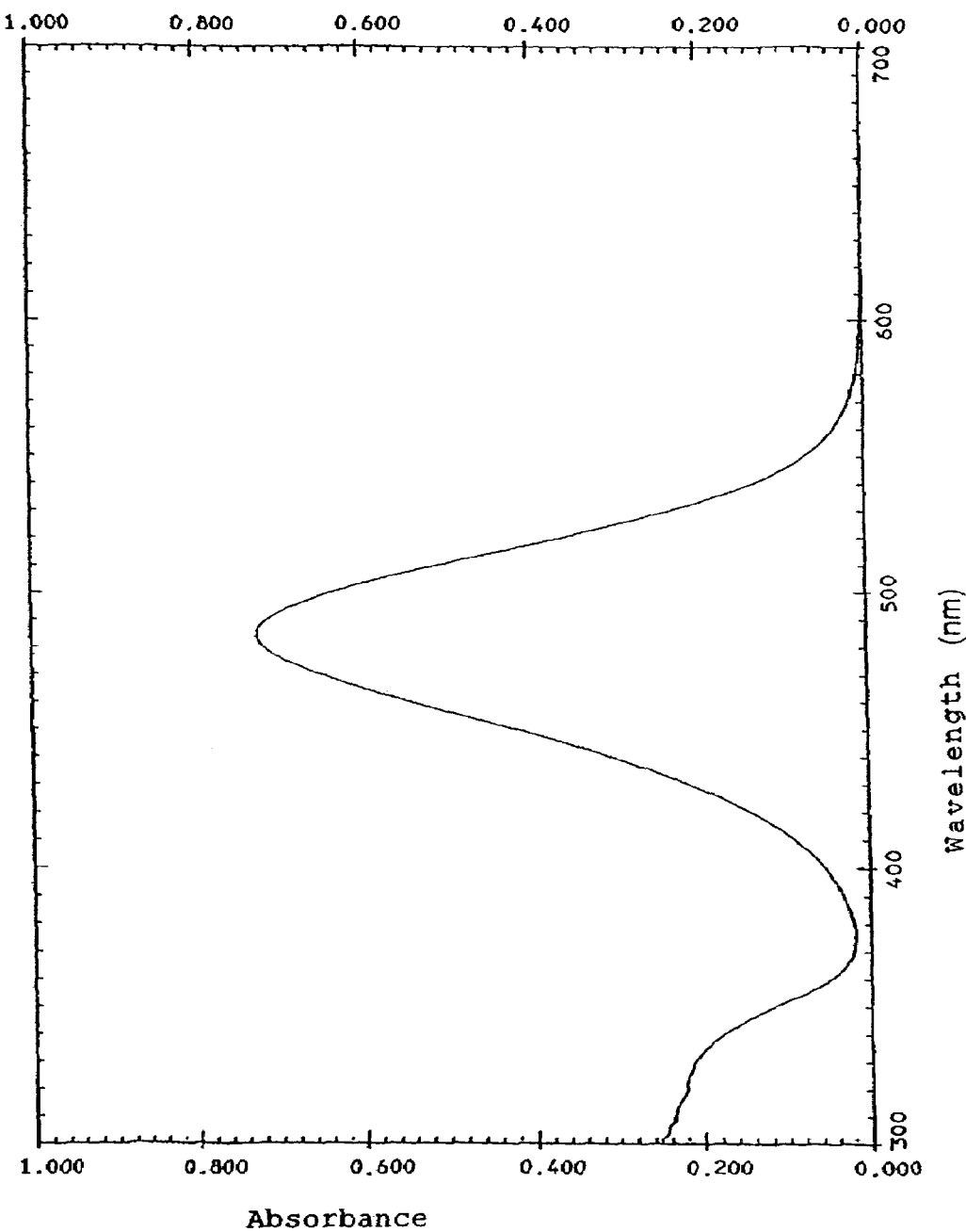

The following Compound (H-5) (0.58 g), rhodanine-3-acetic acid (0.26 g) and ammonium acetate (0.46 g) were dissolved in 2.0 g of acetic acid, and the mixture was stirred under heat at 120° C. After 30 minutes, the heating was stopped, and the mixture was cooled to room temperature. Then, water (100 ml) and ethyl acetate (100 ml) were added, and the mixture was transferred into a separating funnel. An organic layer was separated and dried over anhydrous sodium sulfate, and then the solvent was distilled off. The thus-obtained crude crystal was washed with 2-propanol to give Compound (B-14) shown as an example. 0.66 g. Yield 80.7%. Melting point=175.3-176.9° C. FIG. 6 shows UV absorption spectrum of Compound (B-14) in ethanol. A maximum absorption wavelength (λmax)=485.6 nm. A maximum molecular coefficient (εmax)=43,000 l/mol·cm.

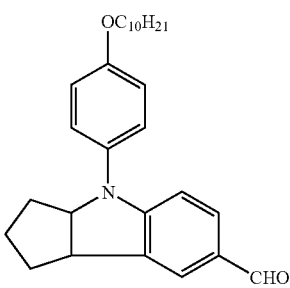

(H-5)

Example W-7 Synthesis of Compound (B-19) Shown as an Example

Figure 7:
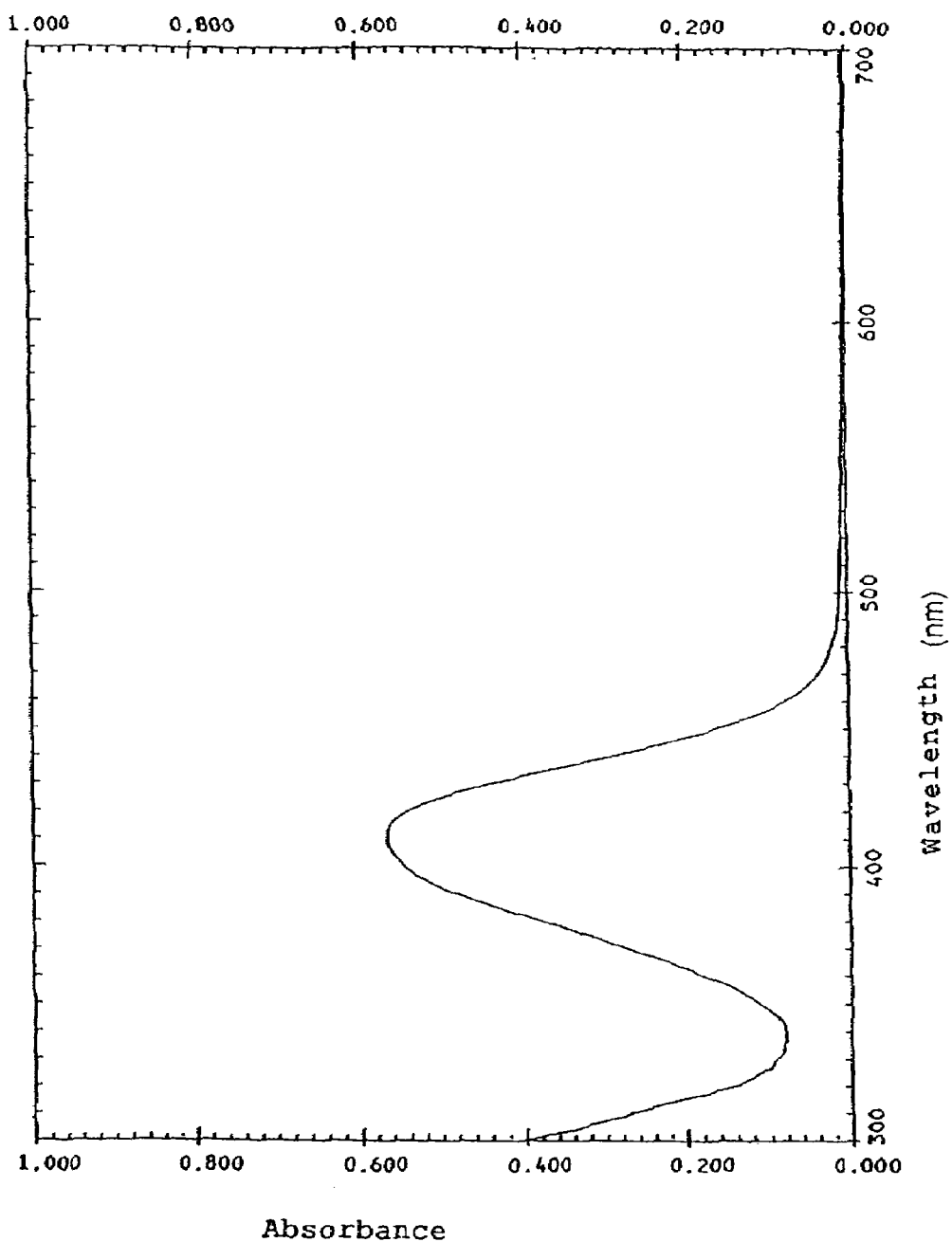

The following Compound (H-6) (0.77 g), rhodanine-3-acetic acid (0.56 g) and ammonium acetate (0.76 g) were dissolved in 2.5 g of acetic acid, and the mixture was stirred under heat at 120° C. After 15 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker, and the crystal was washed with water (100 ml) twice and then washed with 2-propnanol (50 ml) to give Compound (B-19) shown as an example. 1.08 g. Yield 84.3%. Melting point=244.0-246.4° C. FIG. 7 shows UV absorption spectrum of Compound (B-19) in ethanol. A maximum absorption wavelength (λmax)=412.8 nm. A maximum molecular coefficient (ϵmax)=12,300 l/mol·cm.

(H-6)

Example W-8 Synthesis of Compound (B-28) Shown as an Example

Figure 8:
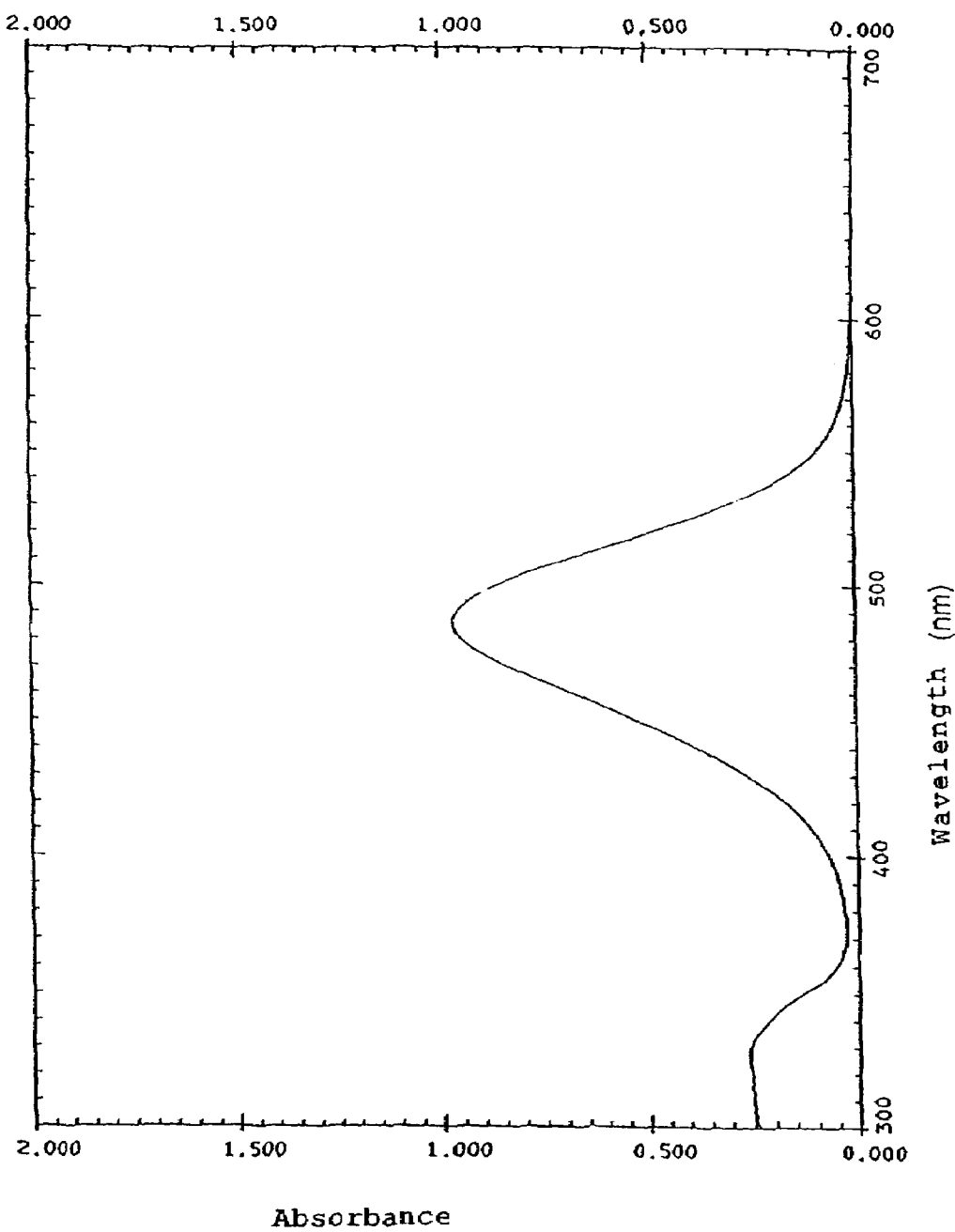

The Compound (H-1) (2.63 g), rhodanine-3-propionic acid (2.05 g) and ammonium acetate (0.52 g) were dissolved in 2.2 g of acetic acid, and the mixture was stirred under heat at 120° C. After 15 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker, and the crystal was washed with water (100 ml) twice and then washed with 2-propnanol (100 ml) to give Compound (B-28) shown as an example. 4.08 g. Yield 90.6%. Melting point=215.6-220.2° C. FIG. 8 shows UV absorption spectrum of Compound (B-28) in ethanol. A maximum absorption wavelength (λmax)=486.0 nm. A maximum molecular coefficient (ϵmax)=43,700 l/mol·cm.

Example W-9 Synthesis of Compound (B-29) Shown as an Example

Figure 9:
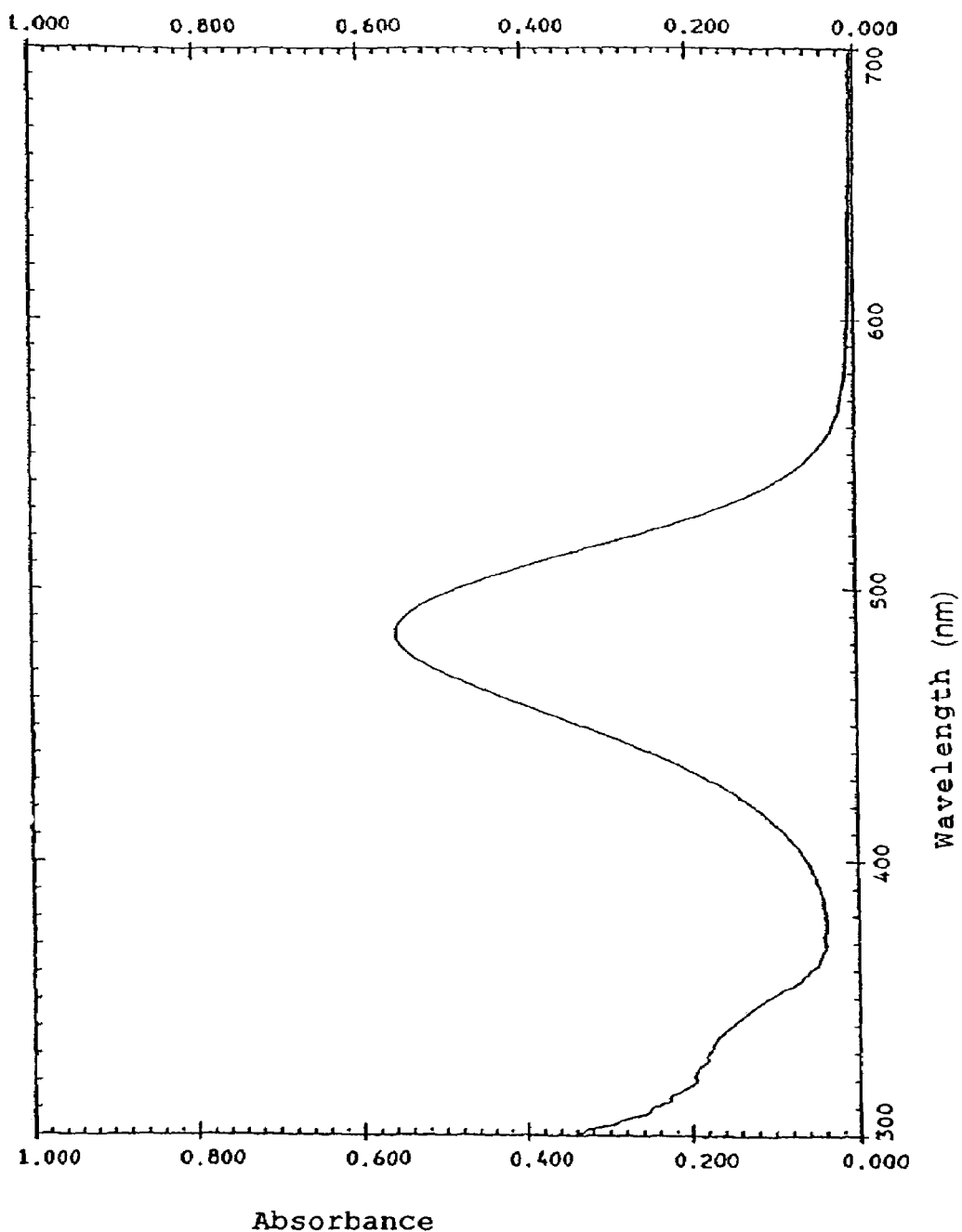

The following Compound (H-7) (1.55 g), rhodanine-3-acetic acid (1.38 g) and ammonium acetate (0.52 g) were dissolved in 2.2 g of acetic acid, and the mixture was stirred under heat at 120° C. After 2 hours, when the heating was stopped, the reaction product immediately solidified. The reaction product was cooled to room temperature, and then, water (50 ml) was added. The mixture was stirred, and a crystal was recovered by filtration. The crystal was transferred into a beaker, and the crystal was washed with water (100 ml) twice and then washed with 2-propnanol (50 ml) to give Compound (B-29) shown as an example. 1.81 g. Yield 58.9%. Melting point=152.4-154.4° C. FIG. 9 shows UV absorption spectrum of Compound (B-29) in ethanol. A maximum absorption wavelength (λmax)=482.4 nm. A maximum molecular coefficient (ϵmax)=25,000 l/mol·cm.

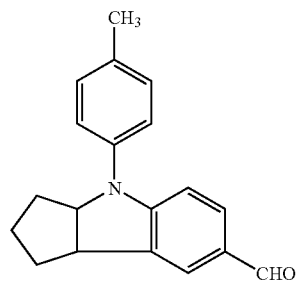

(H-7)

Example W-10 Synthesis of Compound (B-30) Shown as an Example

Figure 10:
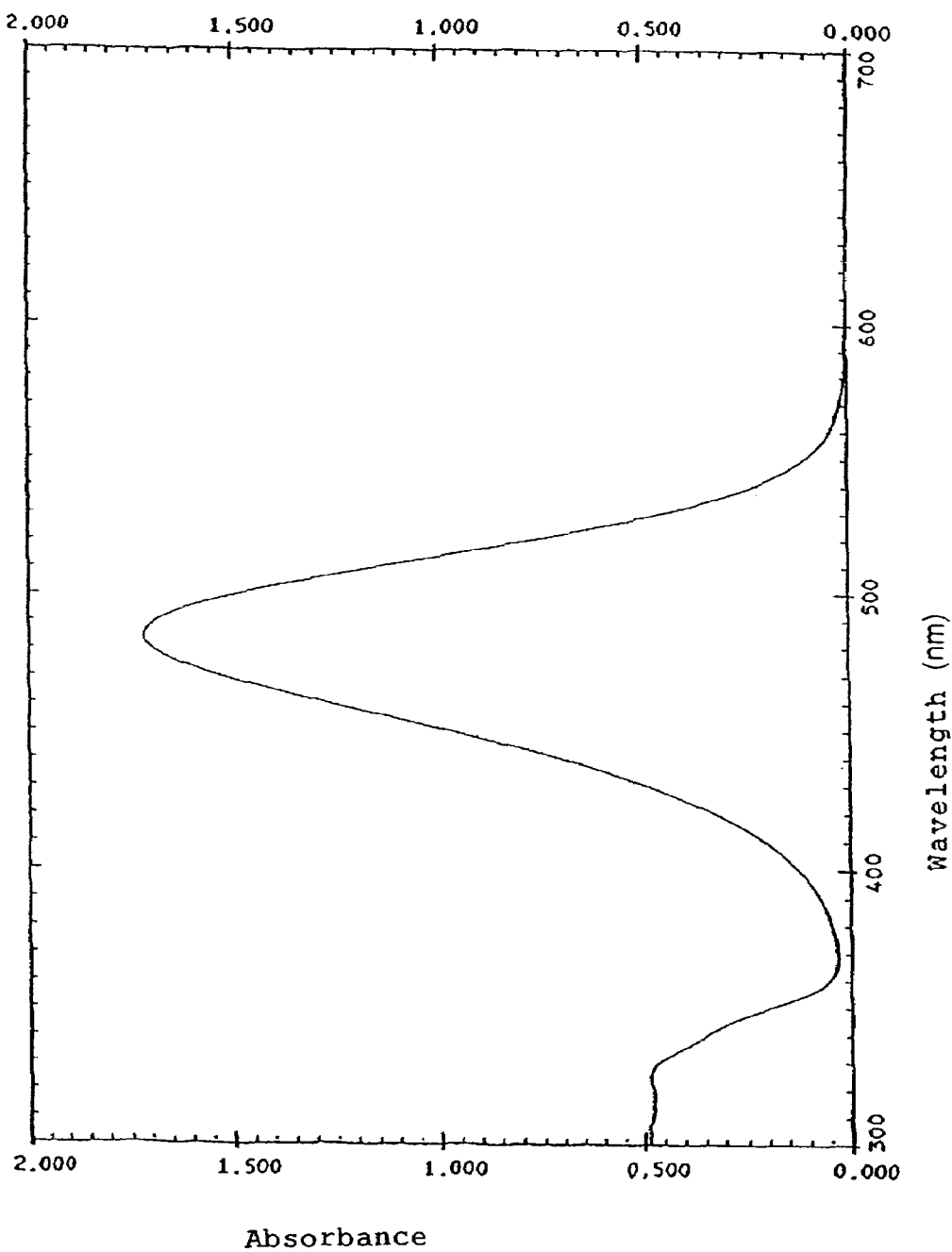

The following Compound (H-8) (1.07 g), rhodanine-3-acetic acid (0.84 g) and ammonium acetate (1.33 g) were dissolved in 4.1 g of acetic acid, and the mixture was stirred under heat at 120° C. After 30 minutes, the heating was stopped, and the mixture was cooled to room temperature. Then, water (100 ml) and ethyl acetate (100 ml) were added, and the mixture was transferred into a separating funnel. An organic layer was separated and dried over anhydrous sodium sulfate, and then the solvent was distilled off. The thus-obtained crude crystal was stirred and washed with isopropyl ether to give Compound (B-30) shown as an example. 1.49 g. Yield 81.3%. Melting point=223.5-224.4° C. FIG. 10 shows UV absorption spectrum of Compound (B-30) in ethanol. A maximum absorption wavelength (λmax)=484.4 nm. A maximum molecular coefficient (ϵmax)=35,700 l/mol·cm.

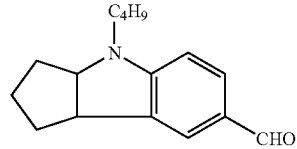

(H-8)

Example W-11 Synthesis of Compound (B-31) Shown as an Example

Figure 11:
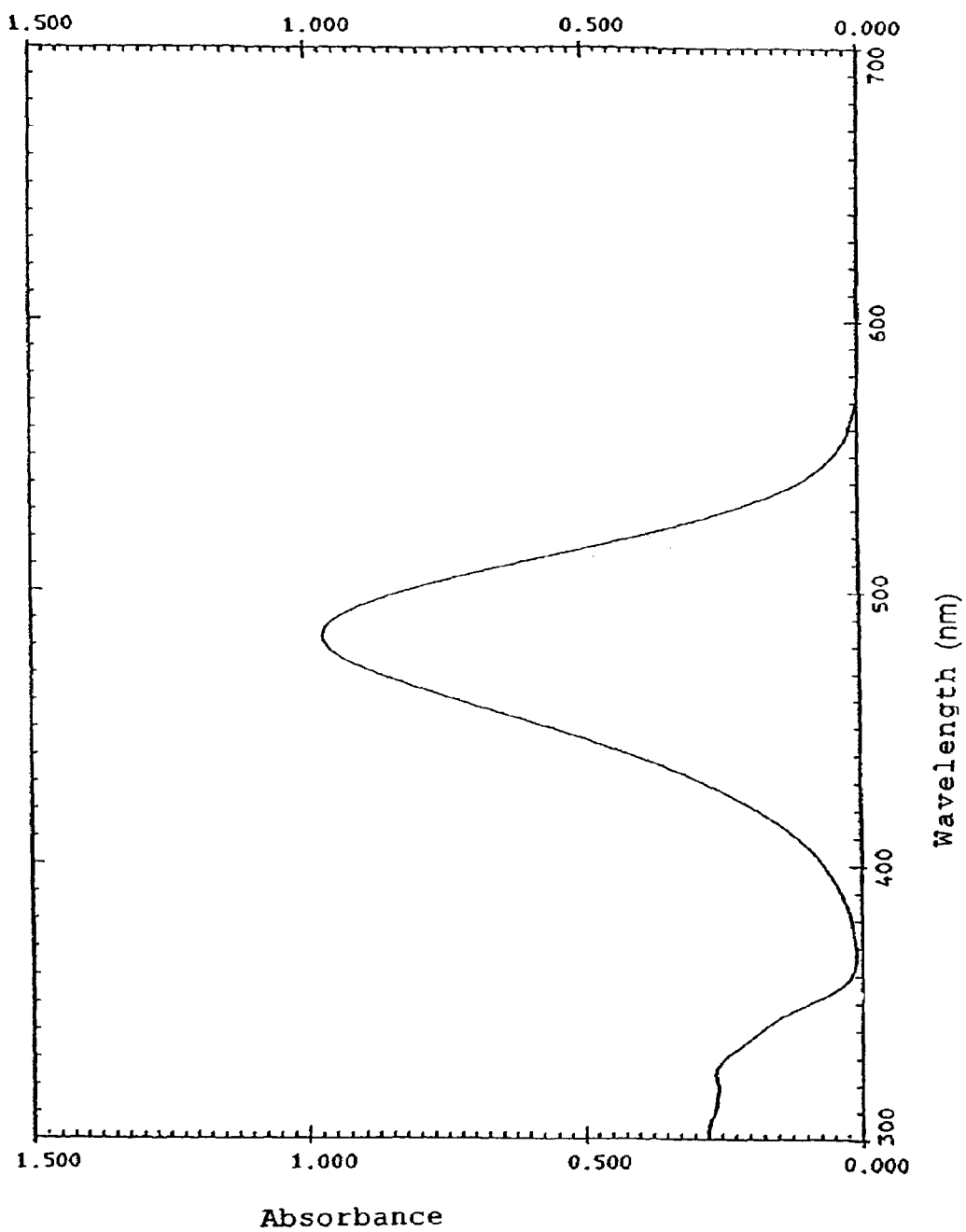

Compound (H-9) (2.26 g), rhodanine-3-acetic acid (1.33 g) and ammonium acetate (1.27 g) were dissolved in 4.3 g of acetic acid, and the mixture was stirred under heat at 120° C. After 30 minutes, the heating was stopped, and the mixture was cooled to room temperature. Then, water (100 ml) and ethyl acetate (100 ml) were added, and the mixture was transferred into a separating funnel. An organic layer was separated and dried over anhydrous sodium sulfate, and then the solvent was distilled off. The thus-obtained crude crystal was stirred and washed with isopropyl ether to give Compound (B-31) shown as an example. 3.02 g. Yield 87.4%. Melting point=160.5-163.5° C. FIG. 11 shows UV absorption spectrum of Compound (B-31) in ethanol. A maximum absorption wavelength (λmax)=484.0 nm. A maximum molecular coefficient (εmax)=48,500 l/mol·cm.

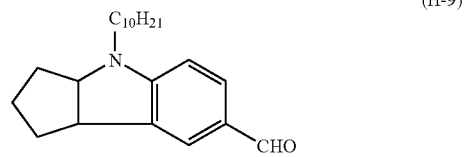
(H-9)

Example W-12 Synthesis of Compound (B-32) Shown as an Example

Figure 12:
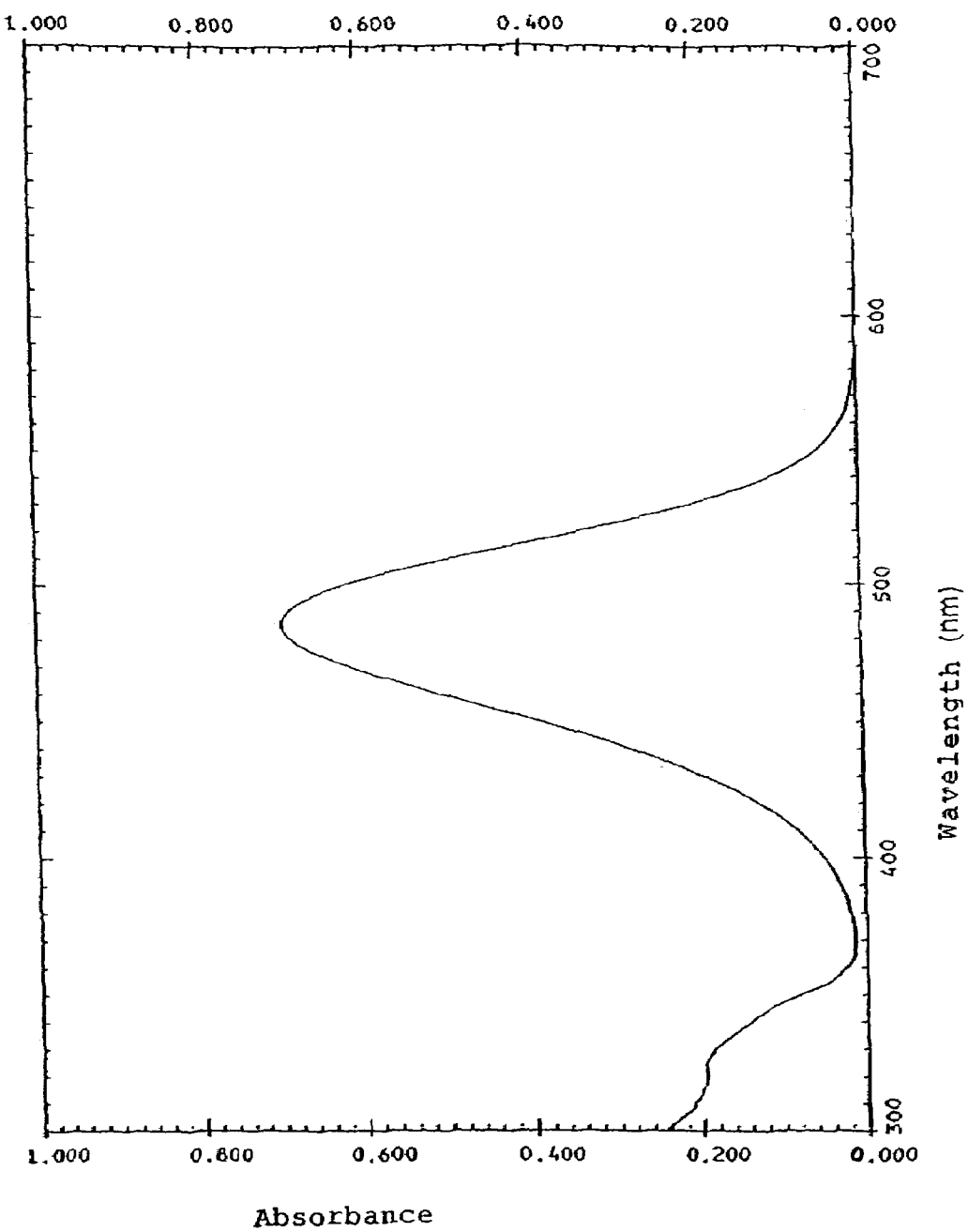

The following Compound (H-10) (1.07 g), rhodanine-3-acetic acid (0.47 g) and ammonium acetate (0.73 g) were dissolved in 3.6 g of acetic acid, and the mixture was stirred under heat at 120° C. After 30 minutes, the heating was stopped, and the mixture was cooled to room temperature. Then, water (100 ml) and ethyl acetate (100 ml) were added, and the mixture was transferred into a separating funnel. An organic layer was separated and dried over anhydrous sodium sulfate, and then the solvent was distilled off. The thus-obtained crude crystal was washed with isopropyl ether to give Compound (B-32) shown as an example. 1.25 g. Yield 83.9%. Melting point=131.1-133.4° C. FIG. 12 shows UV absorption spectrum of Compound (B-32) in ethanol. A maximum absorption wavelength (λmax)=485.8 nm. A maximum molecular coefficient (εmax)=38,800 l/mol·cm.

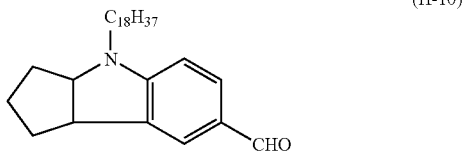
(H-10)

Example W-13 Synthesis of Compound (B-33) Shown as an Example

Figure 13:
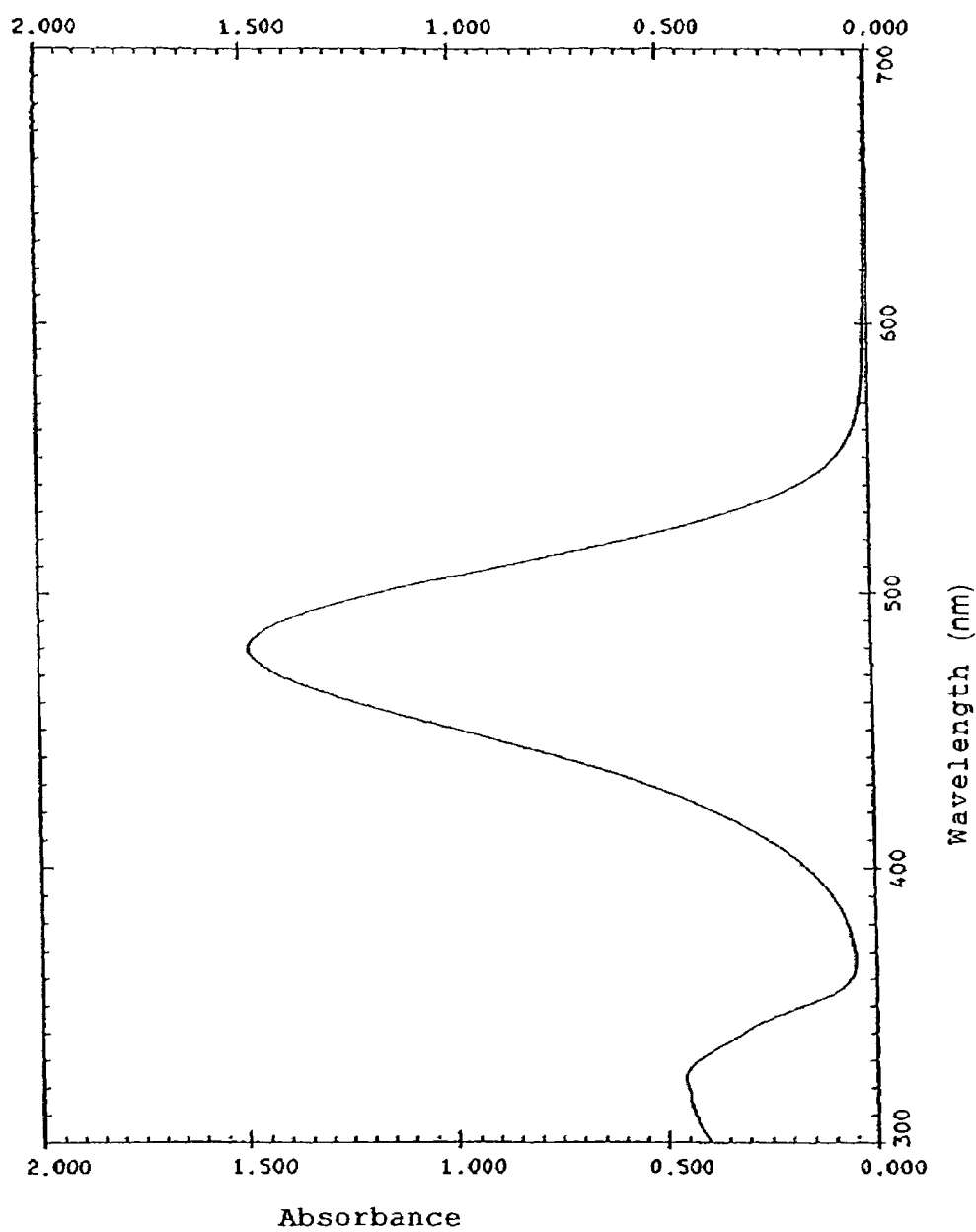

The following Compound (H-11) (2.01 g), rhodanine-3-acetic acid (1.91 g) and ammonium acetate (0.95 g) were dissolved in 2.8 g of acetic acid, and the mixture was stirred under heat at 120° C. After 15 minutes, when the heating was stopped, the reaction product immediately solidified. The reaction product was cooled to room temperature, and then, water (50 ml) was added. The mixture was stirred, and a crystal was recovered by filtration. The crystal was transferred into a beaker, and the crystal was washed with water (100 ml) twice and then washed with 2-propnanol (50 ml) to give Compound (B-33) shown as an example. 2.95 g. Yield 78.9%. Melting point=248.5-249.9° C. FIG. 13 shows UV absorption spectrum of Compound (B-33) in ethanol. A maximum absorption wavelength (λmax)=480.4 nm. A maximum molecular coefficient (εmax)=34,800 l/mol·cm.

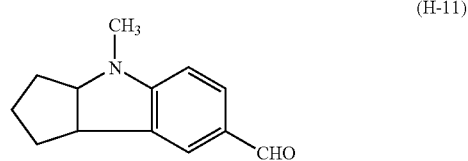
(H-11)

Text Example W-1 Durability Test

The durability of a dye can be measured by stable redox cycle on the basis of cyclic voltammetry. With the exception of some materials, no stable redox cycle is observable with regard to a photographic cyanine and a merocyanine dye. The Compound (B-9) of Example W-4 was measured for a cyclic voltammetry property. The measurement conditions were as follows.

Measurement Conditions

Sweep rate: 200 mV/second

Solvent: Acetonitrile

Electrolytic solution: Tetra-n-butylammonium perchloride

Work electrode: Platinum stationary electrode

Reference electrode: Saturated calomel electrode

Figure 14:
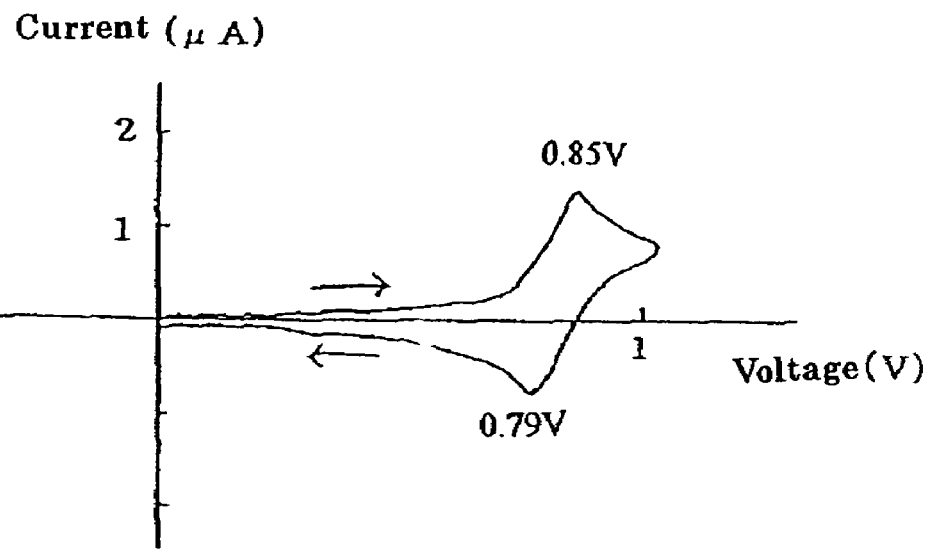
FIGS. 14 and 15 are drawings of cyclic voltammetry characteristics of dyes used in Test Example W-1 and Comparative Text Example W-1.

FIG. 14 shows the results. In FIG. 14, Compound (B-9) exhibited a peak of oxidation potential at 0.85 V, and when the potential was scanned in the reverse direction, a peak was observed at 0.79 V, so that it is seen that the oxidized dye was again reduced to return to a pre-oxidation state. That is, it is shown that this dye is free of decomposition caused by oxidation→reduction and has high durability.

Comparative Test

Example W-1

Figure 15:
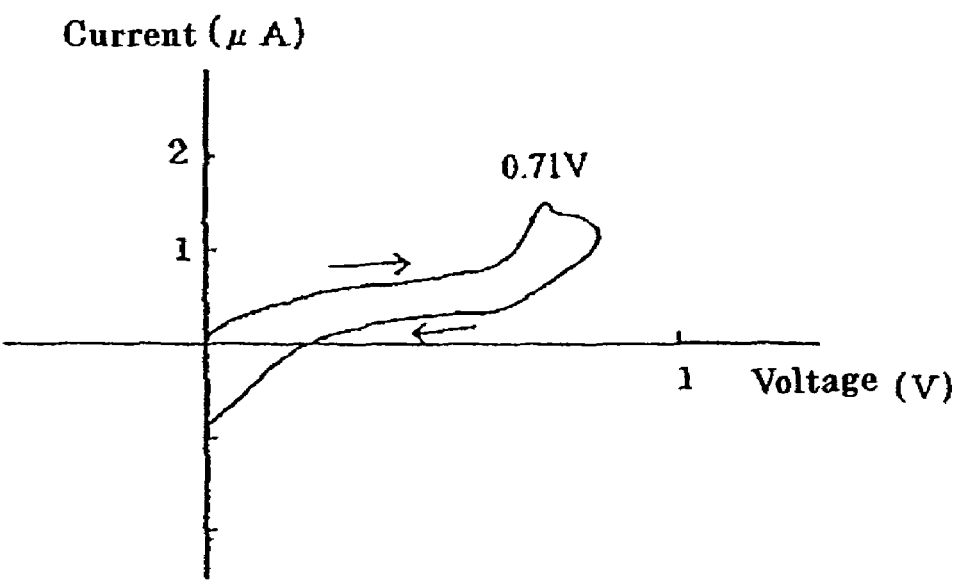

A cyclic voltammetry property was measured in the same manner as in Test Example W-1 except that a merocyanine dye represented by the following Compound (I-1). FIG. 15 shows the results. In FIG. 15, Compound (I-1) exhibited a peak of oxidation potential at 0.71 V, and when the potential was scanned in the reverse direction, no peak was observed. That is, it is shown that the dye was completely decomposed by oxidation.

Example X-1

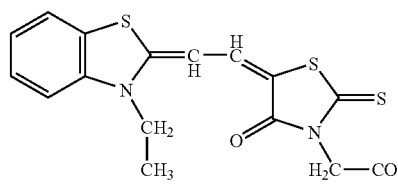
(I-1)

3 Grams of titanium oxide (P-25, supplied by Nippon Aerosil Co., Ltd.), 0.2 g of acetyl acetone and 0.3 g of a surfactant (Triton X-100, supplied by Aldrich Co., Ltd.) were dispersed with a paint conditioner together with 6.5 g of water for 6 hours. The thus-prepared dispersion was applied onto an FTO glass substrate with a wire bar to form a coating having a thickness of 10 µm. Then, the coating was dried at 100° C. for 1 hour and then heated in air at 450° C. for 30 minutes.

0.014 Gram of a dye shown by Compound (B-9) shown as an example and 0.15 g of a steroid compound shown by Compound (E-1) shown as an example were dissolved in 10 ml of ethanol. The above-prepared semiconductor electrode was immersed in the solution at room temperature for 15 hours to carry out adsorption treatment.

A solution of 0.03 M of iodine and 0.5 M of tetra-n-propylammonium iodide in a mixture solution of propylene carbonate/3-methoxy propionitrile=6/4 was used as an electrolytic solution. An electrode prepared by sputtering platinum on FTO was used as a counter electrode.

The electrolytic solution was infiltrated into between the two electrodes to prepare a photoelectric conversion device. The above photoelectric conversion device was exposed to artificial sunlight generated by a solar simulator (AM 1.5, 100 mW/cm² intensity) as a light source so that the device was irradiated from the work electrode side. As a result, the device showed excellent values; an open-circuit voltage of 0.68 V, a short-circuit current density of 9.8 mA/cm², a fill factor of 0.70 and a conversion efficiency of 4.66%.

Example X-2-X-13

Devices were prepared in the same manner as in Example X-1 except that Compound (B-9) shown as an example was replaced with dyes shown in Table 2 and that Compound (E-1) shown as an example was replaced with steroid compounds shown in Table 2, and the devices were evaluated in the same manner as in Example X-1. Table 2 shows the results.

TABLE 2

| | Compound | Steroid compound | Open-circuit voltage (V) | Short-circuit current density (mA/cm²) | Fill factor | Conversion efficiency (%) |
|---|---|---|---|---|---|---|
| Ex. X-2 | B-3 | E-1 | 0.632 | 9.6 | 0.66 | 4.00 |
| Ex. X-3 | B-6 | E-1 | 0.644 | 8.4 | 0.70 | 3.79 |
| Ex. X-4 | B-10 | E-1 | 0.655 | 9.8 | 0.67 | 4.30 |
| Ex. X-5 | B-11 | E-1 | 0.628 | 9.5 | 0.69 | 4.12 |
| Ex. X-6 | B-14 | E-1 | 0.663 | 8.4 | 0.70 | 3.90 |
| Ex. X-7 | B-19 | E-1 | 0.619 | 8.8 | 0.72 | 3.92 |
| Ex. X-8 | B-9 | E-2 | 0.672 | 8.9 | 0.71 | 3.96 |
| Ex. X-9 | B-9 | E-3 | 0.644 | 9.1 | 0.70 | 4.10 |
| Ex. X-10 | B-9 | E-4 | 0.685 | 8.9 | 0.68 | 4.15 |
| Ex. X-11 | B-9 | E-5 | 0.674 | 9.3 | 0.71 | 4.45 |
| Ex. X-12 | B-9 | E-8 | 0.681 | 9.0 | 0.70 | 4.29 |
| Ex. X-13 | B-9 | E-9 | 0.629 | 9.1 | 0.70 | 4.01 |

Ex. = Example

As is clear from the results in Table 2, it is seen that combinations of the dye and the steroid compound in the present invention exhibit excellent conversion efficiency.

Comparative Example X-1

A device was prepared in the same manner as in Example X-1 except that 0.014 g of Compound (B-9) shown as an example was replaced with 0.014 g of a compound (J-1) shown below, and the device was evaluated in the same manner as in Example X-1. As a result, the device showed low values; an open-circuit voltage of 0.58 V, a short-circuit current density of 4.8 mA/cm², a fill factor of 0.53 and a conversion efficiency of 1.48%.

Comparative Example X-2

A device was prepared in the same manner as in Example X-1 except that 0.15 g of the steroid compound (E-1) was replaced with 0.15 g of a compound (J-2) shown below, and the device was evaluated in the same manner as in Example X-1. As a result, the device showed low values; an open-circuit voltage of 0.65 V, a short-circuit current density of 2.7 mA/cm², a fill factor of 0.44 and a conversion efficiency of 0.77%.

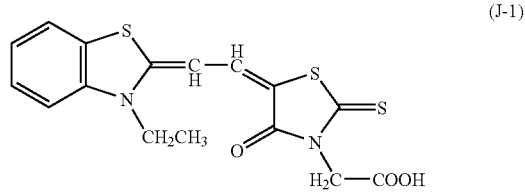
(J-1)

-continued

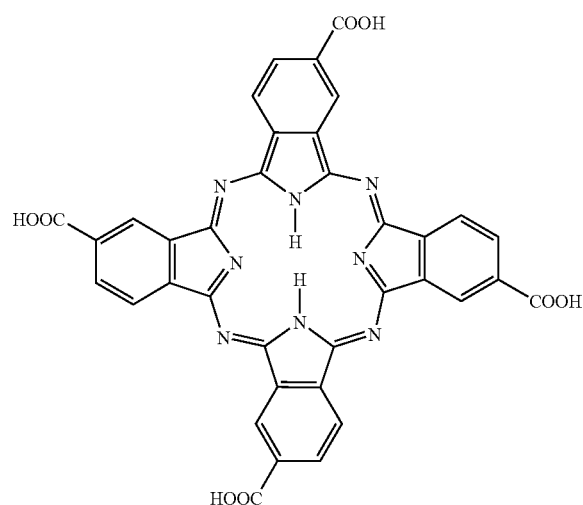

(J-2)

Example Y-1

Synthesis of Compound (C-4)

The following Compound (K-1) (0.92 g), rhodanine-3-acetic acid (0.50 g) and ammonium acetate (0.25 g) were dissolved in 4.8 g of acetic acid, and the mixture was stirred under heat at 120° C. After 30 minutes, the heating was stopped, and the mixture was cooled to room temperature. Then, water (50 ml) was added, and a precipitated crystal was recovered by filtration. The thus-obtained crystal was consecutively washed with water (100 ml) and with a mixture of 2-propanol (10 ml) and water (50 ml) to give Compound (C-4) shown as an example. 1.23 g. Yield 96%.

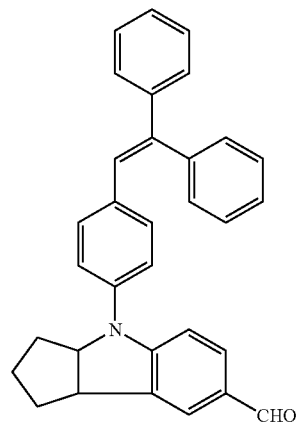

(K-1)

Example Y-2

Preparation of Photoelectric Conversion Device

3 Grams of titanium oxide (P-25, supplied by Nippon Aerosil Co., Ltd.), 0.2 g of acetyl acetone and 0.3 g of a surfactant (Triton X-100, supplied by Aldrich Co., Ltd.) were dispersed with a paint conditioner together with 6.5 g of water for 6 hours. Further, 1.2 g of polyethylene glycol (#20,000) was added to the dispersion, to prepare a paste. The thus-prepared paste was applied onto an FTO glass substrate to form a coating having a thickness of 10 μm. Then, the coating was dried at room temperature and then heated in air at 500° C. for 1 hour.

The above-prepared semiconductor electrode was immersed in a solution of a dye shown by Compound (C-4) shown as an example in 0.3 mM of ethanol at room temperature for 15 hours to carry out adsorption treatment.

A solution of 0.03 M of iodine and 0.5 M of tetra-n-propylammonium iodide in a mixture solution of propylene carbonate/acetonitrile=6/4 was used as an electrolytic solution. An electrode prepared by sputtering platinum on FTO was used as a counter electrode.

The electrolytic solution was infiltrated into between the two electrodes to prepare a photoelectric conversion device. The above photoelectric conversion device was exposed to artificial sunlight generated by a solar simulator (AM 1.5G, irradiation intensity 100 mW/cm$^2$) as a light source so that the device was irradiated from the work electrode side. As a result, the device showed excellent values; an open-circuit voltage of 0.65 V, a short-circuit current density of 10.5 mA/cm$^2$, a fill factor of 0.68 and a conversion efficiency of 4.64%.

Example Y-3-Y-6

Devices were prepared in the same manner as in Example Y-2 except that Compound (C-4) shown as an example was replaced with dyes shown in Table 3 and evaluated in the same manner as in Example Y-2. Table 3 shows the results.

TABLE 3

| | Compound | Open-circuit voltage (V) | Short-circuit current density (mA/cm$^2$) | Fill factor | Conversion efficiency (%) |
|---|---|---|---|---|---|
| Ex. Y-3 | C-3 | 0.68 | 9.3 | 0.64 | 4.05 |
| Ex. Y-4 | C-5 | 0.66 | 10.2 | 0.64 | 4.31 |
| Ex. Y-5 | C-8 | 0.66 | 7.8 | 0.65 | 3.35 |
| Ex. Y-6 | C-11 | 0.65 | 8.3 | 0.65 | 3.51 |

Ex. = Example

As is clear from the results in Table 3, it is seen that the dyes of the present invention exhibit excellent conversion efficiency.

Comparative Example Y-1

A device was prepared in the same manner as in Example Y-2 except that Compound (C-4) shown as an example was replaced with a compound (L-1) shown below, and the device was evaluated in the same manner as in Example Y-2. As a result, the device showed low values; an open-circuit voltage of 0.58 V, a short-circuit current density of 5.3 mA/cm$^2$, a fill factor of 0.55 and a conversion efficiency of 1.69%.

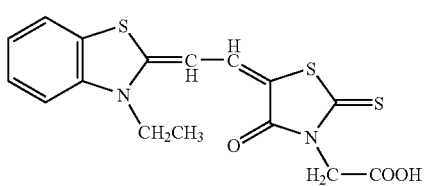

(L-1)

Example Z-1

Synthesis of Compound (D-9)

The following compound (M-1) (0.10 g), tetra-n-butylammonium hydroxide (2.5 ml) and water (7.5 ml) were placed in a flask and stirred on an ice bath. After 30 minutes, a 0.1 N nitric acid aqueous solution was dropwise added to adjust the mixture to a pH of 4. A precipitated crystal was recovered by filtration and washed with water to give 0.10 g of a crystal.

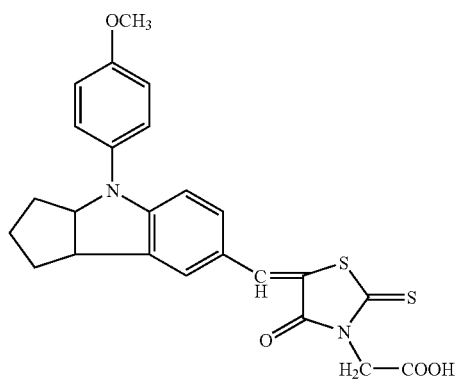

(M-1)

Example Z-2

Preparation of Photoelectric Conversion Device

3 Grams of titanium oxide (P-25, supplied by Nippon Aerosil Co., Ltd.), 0.2 g of acetyl acetone and 0.3 g of a surfactant (Triton X-100, supplied by Aldrich Co., Ltd.) were dispersed with a paint conditioner together with 6.5 g of water for 6 hours. Further, 1.2 g of polyethylene glycol (#20,000) was added to the dispersion, to prepare a paste. The thus-prepared paste was applied onto an FTO glass substrate to form a coating having a thickness of 10 µm. Then, the coating was dried at room temperature and then heated in air at 500° C. for 1 hour.

The above-prepared semiconductor electrode was immersed in a solution of a dye shown by Compound (D-9) shown as an example in 0.3 mM of ethanol at room temperature for 15 hours to carry out adsorption treatment.

A solution of 0.1 M of lithium iodide, 0.05 M of iodine and 0.5 M of 1,2-dimethyl-3-n-propylammonium iodide in 3-methoxyacetonitrile was used as an electrolytic solution. An electrode prepared by sputtering platinum on FTO was used as a counter electrode.

The electrolytic solution was infiltrated into between the two electrodes to prepare a photoelectric conversion device.

The above device was exposed to artificial sunlight generated by a solar simulator (AM 1.5G, irradiation intensity 100 mW/cm$^2$) as a light source so that the device was irradiated from the work electrode side. As a result, the device showed excellent values; an open-circuit voltage of 0.65 V, a short-circuit current density of 10.5 mA/cm$^2$, a fill factor of 0.63 and a conversion efficiency of 4.30%.

Example Z-3-Z-5

Devices were prepared in the same manner as in Example Z-2 except that Compound (D-9) shown as an example was replaced with dyes shown in Table 4 and evaluated in the same manner as in Example Z-2. Table 4 shows the results.

TABLE 4

| | Compound | Open-circuit voltage (V) | Short-circuit current density (mA/cm$^2$) | Fill factor | Conversion efficiency (%) |
|---|---|---|---|---|---|
| Ex. Z-3 | D-3 | 0.67 | 9.8 | 0.62 | 4.07 |
| Ex. Z-4 | D-10 | 0.64 | 9.9 | 0.63 | 3.99 |
| Ex. Z-5 | D-14 | 0.64 | 10.1 | 0.63 | 4.07 |

Ex. = Example

As is clear from the results in Table 4, it is seen that the dyes of the present invention exhibit excellent conversion efficiency.

Referential Example Z-1

A device was prepared in the same manner as in Example Z-2 except that Compound (D-9) shown as an example was replaced with the above compound (M-1), and the device was evaluated in the same manner as in Example Z-2. As a result, the device showed low values as compared with the counterpart in Example Z-2; an open-circuit voltage of 0.56 V, a short-circuit current density of 10.3 mA/cm$^2$, a fill factor of 0.63 and a conversion efficiency of 3.63%.

INDUSTRIAL UTILITY

The dye of the present invention has excellent photoelectric conversion properties and is suitable for use in a semiconductor electrode in a solar cell, and the like. Further, the photoelectric conversion device which has a semiconductor electrode containing the above dye is excellent in photoelectric conversion efficiency.

The invention claimed is:

1. A merocyanine dye having a structure represented by the general formula (IV), (IV)

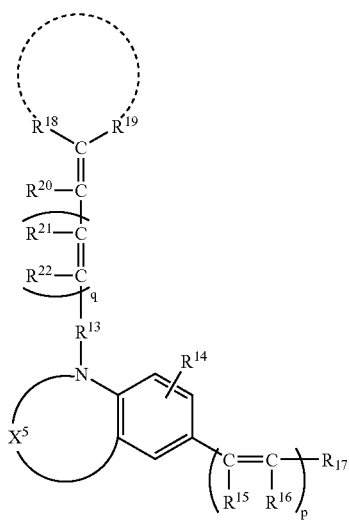

wherein $R^{13}$ is an arylene group or a heterocyclic moiety and may have a substituent; $R^{14}$ is a hydrogen atom, an alkyl group, an alkoxy group or a halogen atom; each of $R^{15}$ and $R^{16}$ is a hydrogen atom, an alkyl group, an alkoxy group, an alkylthio group, a mono-substituted amino group, a di-substituted amino group, an aralkyl group, an alkenyl group, an aryl group or a heterocyclic moiety and may have a substituent; $R^{17}$ is a substituent having an acidic group; each of $R^{18}$ and $R^{19}$ is a hydrogen atom, an alkyl group, an aryl group or a heterocyclic moiety and may have a substituent, and $R^{18}$ and $R^{19}$ may bond directly or through a binding group; each of $R^{20}$, $R^{21}$ and $R^{22}$ is a hydrogen atom, an alkyl group, an alkoxy group, an aryl group or a heterocyclic moiety; $X^5$ is a binding group that forms a cyclic structure together with an amino group; p is an integer of 0 to 2; q is an integer of 0 to 2; and a carbon-carbon double bond may be any one of E form and Z form.

2. The merocyanine dye of claim 1, wherein $R^{17}$ in the general formula (IV) is a substituent having an acidic group, represented by one of the following formulae (113) to (123), (125), (131) to (133) and (137) to (140),

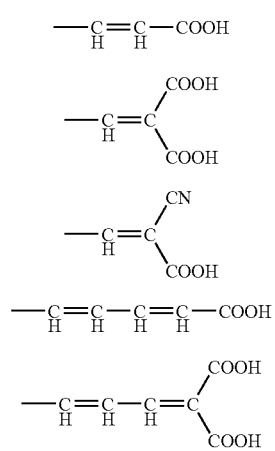

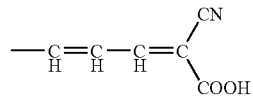

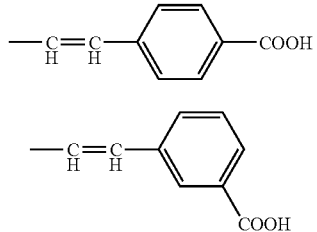

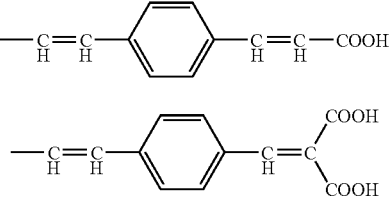

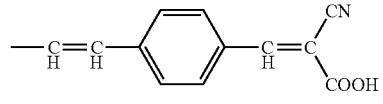

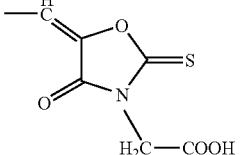

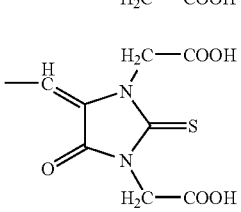

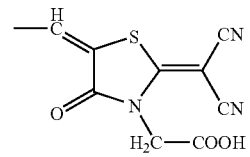

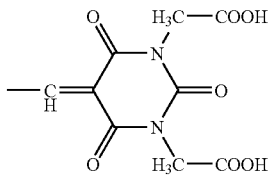

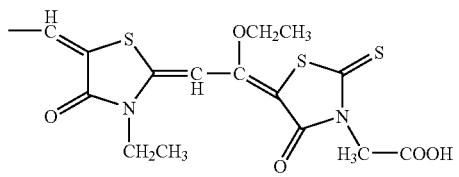

-continued

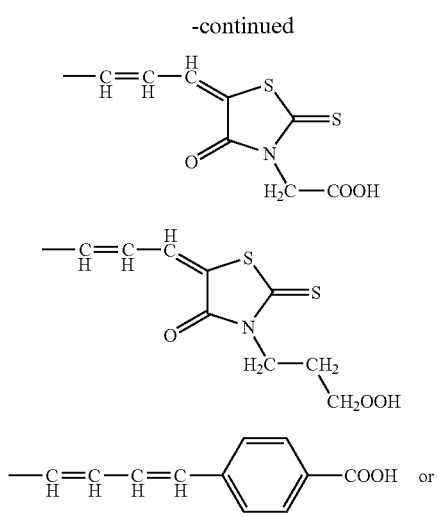

a substituent having an acidic group, represented by the general formula (203),

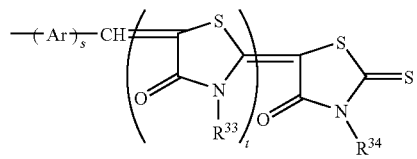

in which Ar is an arylene group, s is 0 or 1, t is 0 to 2, each of $R^{33}$ and $R^{34}$ is an alkyl group or an alkyl or aryl group having an acidic group, provided that at least one of $R^{33}$ and $R^{34}$ is an alkyl or aryl group having an acid group.

3. A photoelectric conversion material containing the merocyanine dye recited in claim 1.

4. A semiconductor electrode formed of a substrate having an electrically conductive surface, a semiconductor layer coated on the electrically conductive surface and a dye adsorbed on the surface of the semiconductor layer, wherein said dye contains the merocyanine dye recited in claim 1.

5. A photoelectric conversion device to which the merocyanine dye recited in claim 1 is applied.

6. A photoelectric conversion device, which has a semiconductor electrode formed of a substrate having an electrically conductive surface, a semiconductor layer coated on the electrically conductive surface and a dye adsorbed on the surface of the semiconductor layer, wherein said dye contains the merocyanine dye recited in claim 1.

7. The semiconductor electrode of claim 4, wherein a semiconductor constituting the semiconductor layer contains at least one chalcogenide compound of a metal selected from titanium, tin, zinc, iron, copper, tungsten, zirconium, hafnium, strontium, indium, cerium, yttrium, lanthanum, vanadium, niobium, tantalum, cadmium, lead, silver, antimony, bismuth, molybdenum, aluminum, gallium, chromium, cobalt or nickel.

* * * * *